(12) United States Patent
Yu et al.

(10) Patent No.: US 10,646,494 B2
(45) Date of Patent: May 12, 2020

(54) HETEROCYCLE-SUBSTITUTED TETRACYCLIC COMPOUNDS AND METHODS OF USE THEREOF FOR THE TREATMENT OF VIRAL DISEASES

(71) Applicant: Merck Sharp & Dohme Corp., Rahway, NJ (US)

(72) Inventors: Wensheng Yu, Edison, NJ (US); Ling Tong, Warren, NJ (US); Joseph A. Kozlowski, Princeton, NJ (US); Craig A. Coburn, Seattle, WA (US); De-Yi Yang, Morris Plains, NJ (US); Deyou Sha, Yardley, PA (US); Jae-Hun Kim, Scotch Plains, NJ (US); Michael Dwyer, Scotch Plains, NJ (US); Kartik M Keertikar, East Windsor, NJ (US); Bin Hu, Shanghai (CN); Bin Zhong, Shanghai (CN); Jinglai Hao, Shanghai (CN); Dahai Wang, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/326,039

(22) PCT Filed: Aug. 14, 2017

(86) PCT No.: PCT/US2017/046676
§ 371 (c)(1),
(2) Date: Feb. 15, 2019

(87) PCT Pub. No.: WO2018/035005
PCT Pub. Date: Feb. 22, 2018

(65) Prior Publication Data
US 2019/0175602 A1 Jun. 13, 2019

(30) Foreign Application Priority Data

Aug. 18, 2016 (WO) ................ PCT/CN2016/095882

(51) Int. Cl.
| | |
|---|---|
| *C07D 498/04* | (2006.01) |
| *A61K 31/5365* | (2006.01) |
| *C07D 519/00* | (2006.01) |
| *C07D 513/04* | (2006.01) |
| *A61K 45/06* | (2006.01) |
| *A61P 31/12* | (2006.01) |
| *A61P 31/22* | (2006.01) |
| *A61P 31/14* | (2006.01) |
| *A61K 31/4995* | (2006.01) |

(52) U.S. Cl.
CPC ...... *A61K 31/5365* (2013.01); *A61K 31/4995* (2013.01); *A61K 45/06* (2013.01); *A61P 31/12* (2018.01); *A61P 31/14* (2018.01); *A61P 31/22* (2018.01); *C07D 498/04* (2013.01); *C07D 513/04* (2013.01); *C07D 519/00* (2013.01)

(58) Field of Classification Search
CPC ............ C07D 498/04; A61K 31/5365; A61K 31/4995
See application file for complete search history.

(56) References Cited

U.S. PATENT DOCUMENTS

| | | | |
|---|---|---|---|
| 9,242,988 B2 | 1/2016 | Girijavallabhan et al. | |
| 9,555,038 B2 * | 1/2017 | Yu ........................ | C07D 498/04 |
| 2012/0083483 A1 | 4/2012 | Coburn et al. | |
| 2015/0335648 A1* | 11/2015 | Yu ........................ | C07D 498/04 |
| | | | 514/51 |
| 2016/0045526 A1 | 2/2016 | Girijavallabhan et al. | |

FOREIGN PATENT DOCUMENTS

| | | | |
|---|---|---|---|
| WO | 2012041014 | * | 4/2012 |
| WO | WO2012/041014 A1 | | 4/2012 |
| WO | 2014/110706 A1 | | 7/2014 |
| WO | WO2014110705 A1 | | 7/2014 |

OTHER PUBLICATIONS

International Search Report and Written Opinion for PCT/CN2016/095882 dated May 19, 2017, 16 pages.
International Search Report and Written Opinion for PCT/US2017/046676, dated Nov. 6, 2017, 23 pages.

* cited by examiner

*Primary Examiner* — D Margaret M Seaman
(74) *Attorney, Agent, or Firm* — Jeffrey P. Bergman; Catherine D. Fitch

(57) ABSTRACT

The present invention relates to novel Heterocycle-Substituted Tetracyclic Compounds of Formula (I): (I) and pharmaceutically acceptable salts thereof, wherein A, A', $R^2$ $R^3$ and $R^5$ are as defined herein. The present invention also relates to compositions comprising at least one Heterocycle-Substituted Tetracyclic Compound, and methods of using the Heterocycle-Substituted Tetracyclic Compounds for treating or preventing HCV infection in a patient.

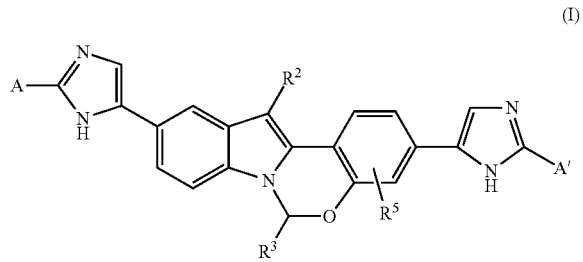

(I)

16 Claims, No Drawings
Specification includes a Sequence Listing.

SEQUENCE LISTING

```
<160> NUMBER OF SEQ ID NOS: 12

<210> SEQ ID NO 1
<211> LENGTH: 18
<212> TYPE: DNA
<213> ORGANISM: Artificial Sequence
<220> FEATURE:
<223> OTHER INFORMATION: PCR PRIMER

<400> SEQUENCE: 1
ccggctacct gcccattc                                                18

<210> SEQ ID NO 2
<211> LENGTH: 22
<212> TYPE: DNA
<213> ORGANISM: Artificial Sequence
<220> FEATURE:
<223> OTHER INFORMATION: PCR PRIMERS

<400> SEQUENCE: 2
ccagatcatc ctgatcgaca ag                                           22

<210> SEQ ID NO 3
<211> LENGTH: 24
<212> TYPE: DNA
<213> ORGANISM: Artificial Sequence
<220> FEATURE:
<223> OTHER INFORMATION: PCR PRIMERS

<400> SEQUENCE: 3
acatcgcatc gagcgagcac gtac                                         24

<210> SEQ ID NO 4
<211> LENGTH: 24
<212> TYPE: DNA
<213> ORGANISM: Artificial Sequence
<220> FEATURE:
<223> OTHER INFORMATION: PCR PRIMERS

<400> SEQUENCE: 4
cgcgtctcct ttgagctgtt tgca                                         24

<210> SEQ ID NO 5
<211> LENGTH: 15
<212> TYPE: DNA
<213> ORGANISM: Artificial Sequence
```

-continued

<220> FEATURE:
<223> OTHER INFORMATION: PCR PRIMERS

<400> SEQUENCE: 5
acggcgagcc cttgg                                                    15

<210> SEQ ID NO 6
<211> LENGTH: 21
<212> TYPE: DNA
<213> ORGANISM: Artificial Sequence
<220> FEATURE:
<223> OTHER INFORMATION: PCR PRIMERS

<400> SEQUENCE: 6
tttctgctgt ctttgggacc t                                             21

<210> SEQ ID NO 7
<211> LENGTH: 17
<212> TYPE: DNA
<213> ORGANISM: Artificial Sequence
<220> FEATURE:
<223> OTHER INFORMATION: PCT PRIMERS

<400> SEQUENCE: 7
atggacaggc gccctga                                                  17

<210> SEQ ID NO 8
<211> LENGTH: 20
<212> TYPE: DNA
<213> ORGANISM: Artificial Sequence
<220> FEATURE:
<223> OTHER INFORMATION: PCT PRIMERS

<400> SEQUENCE: 8
ttgatgggca gcttggtttc                                               20

<210> SEQ ID NO 9
<211> LENGTH: 17
<212> TYPE: DNA
<213> ORGANISM: Artificial Sequence
<220> FEATURE:
<223> OTHER INFORMATION: PCR PRIMERS

<400> SEQUENCE: 9
cacgccatgc gctgcgg                                                  17

<210> SEQ ID NO 10
<211> LENGTH: 19
<212> TYPE: DNA
<213> ORGANISM: Artificial Sequence
<220> FEATURE:
<223> OTHER INFORMATION: PCR PRIMERS

<400> SEQUENCE: 10
tgcggaaccg gtgagtaca                                                19

<210> SEQ ID NO 11
<211> LENGTH: 21
<212> TYPE: DNA
<213> ORGANISM: Artificial Sequence
<220> FEATURE:
<223> OTHER INFORMATION: PCR PRIMERS

<400> SEQUENCE: 11
gcgggtttat ccaagaaagg a                                             21

```
<210> SEQ ID NO 12
<211> LENGTH: 21
<212> TYPE: DNA
<213> ORGANISM: Artificial Sequence
<220> FEATURE:
<223> OTHER INFORMATION: PCR PRIMERS

<400> SEQUENCE: 12
cggaattgcc aggacgaccg g                                              21
```

HETEROCYCLE-SUBSTITUTED TETRACYCLIC COMPOUNDS AND METHODS OF USE THEREOF FOR THE TREATMENT OF VIRAL DISEASES

CROSS-REFERENCE TO RELATED APPLICATIONS

This application is the national stage application under 35 U.S.C. 371 of International Patent Application No. PCT/US17/046676, filed Aug. 14, 2017, which claims priority to International Patent Application No. PCT/CN2016/095882, filed Aug. 18, 2016. Each of the aforementioned applications is incorporated by reference in its entirety.

FIELD OF THE INVENTION

The present invention relates to novel Heterocycle-Substituted Tetracyclic Compounds, compositions comprising at least one Heterocycle-Substituted Tetracyclic Compound, and methods of using the Heterocycle-Substituted Tetracyclic Compounds for treating or preventing HCV infection in a patient.

BACKGROUND OF THE INVENTION

Hepatitis C virus (HCV) is a major human pathogen. A substantial fraction of these HCV-infected individuals develop serious progressive liver disease, including cirrhosis and hepatocellular carcinoma, which are often fatal.

Recent attention has been focused toward the identification of inhibitors of HCV NS5A. HCV NS5A is a 447 amino acid phosphoprotein which lacks a defined enzymatic function. It runs as 56 kd and 58 kd bands on gels depending on phosphorylation state (Tanji, et al. *J. Virol.* 69:3980-3986 (1995)). HCV NS5A resides in replication complex and may be responsible for the switch from replication of RNA to production of infectious virus (Huang, Y, et al., *Virology* 364:1-9 (2007)).

Multicyclic HCV NS5A inhibitors have been reported. See U.S. Patent Publication Nos. US20080311075, US20080044379, US20080050336, US20080044380, US20090202483 and US2009020478. HCV NS5A inhibitors having fused tricyclic moieties are disclosed in International Patent Publication Nos. WO 10/065681, WO 10/065668, and WO 10/065674.

Other HCV NS5A inhibitors and their use for reducing viral load in HCV infected humans have been described in U.S. Patent Publication No. US20060276511.

SUMMARY OF THE INVENTION

In one aspect, the present invention provides Compounds of Formula

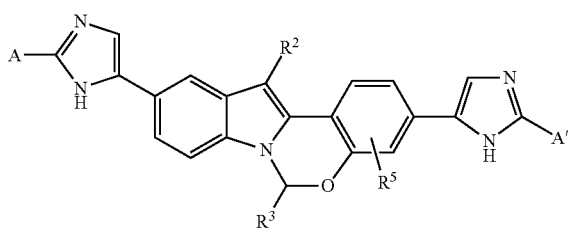

(I)

or a pharmaceutically acceptable salt thereof, wherein:

A is:

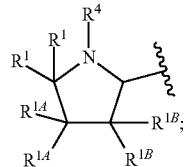

A' is:

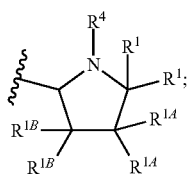

each occurrence of $R^1$ is independently selected from H, $C_1$-$C_6$ alkyl, $C_3$-$C_7$ cycloalkyl, $C_1$-$C_6$ haloalkyl, —O—$C_1$-$C_6$ alkyl, —N($R^9$)$_2$, —O—($C_1$-$C_6$ haloalkyl), and halo;

each occurrence of $R^{1A}$ is independently selected from H, $C_1$-$C_6$ alkyl, $C_3$-$C_7$ cycloalkyl, $C_1$-$C_6$ haloalkyl, —O—$C_1$-$C_6$ alkyl, —N($R^9$)$_2$, —O—($C_1$-$C_6$ haloalkyl), and halo, or one $R^{1A}$ group and an $R^1$ group that are attached to same ring, together with the ring carbon atoms to which they are attached, can combine to form a fused $C_3$-$C_7$ cycloalkyl group, or two $R^{1A}$ groups that are attached to the same carbon atom, and the common carbon atom to which they are attached, can combine to form a spirocyclic $C_3$-$C_7$ cycloalkyl group;

each occurrence of $R^{1B}$ is independently H, $C_1$-$C_6$ alkyl, $C_3$-$C_7$ cycloalkyl, $C_1$-$C_6$ haloalkyl, —O—$C_1$-$C_6$ alkyl, —N($R^9$)$_2$, —O—($C_1$-$C_6$ haloalkyl), or halo, or an $R^{1B}$ group and an $R^{1A}$ group that are attached to the same ring, together with the carbon atoms to which they are attached, can combine to form a fused $C_3$-$C_7$ cycloalkyl group, or an $R^{1B}$ group and an $R^1$ group that are attached to the same ring, can combine to form a bridging group having the formula —CH$_2$— or —CH$_2$CH$_2$—;

$R^2$ is H, $C_1$-$C_6$ alkyl, $C_3$-$C_7$ cycloalkyl, phenyl or halo, wherein said phenyl group and said $C_3$-$C_7$ cycloalkyl can be optionally substituted with up to 4 groups, which can be the same or different and are selected from $C_1$-$C_6$ alkyl, halo, —O—$C_1$-$C_6$ alkyl and —N($R^9$)$_2$;

$R^3$ is selected from furanyl, oxazolyl, oxadiazolyl, isoxazolyl, imidazolyl, benzoxazolyl, benzisoxazolyl, benzimidazolyl, pyrazolo[1,5-a]pyridinyl, imidazo[1,2-a]pyridinyl, 6,7-dihydro-5H-pyrrolo[1,2-a]imidazolyl, 1,3,4-thiadiazolyl and 1,2,3-thiadiazolyl, wherein said furanyl, oxazolyl, oxadiazolyl, isoxazolyl, imidazolyl, benzoxazolyl, benzisoxazolyl, benzimidazolyl, pyrazolo[1,5-a]pyridinyl, imidazo[1,2-a]pyridinyl, 6,7-dihydro-5H-pyrrolo[1,2-a]imidazolyl, 1,3,4-thiadiazolyl and 1,2,3-thiadiazolyl groups can be optionally substituted on one or more ring carbon atoms with $R^6$, and optionally substituted on a ring nitrogen atom with $C_1$-$C_6$ alkyl;

each occurrence of $R^4$ is independently selected from —C(O)—C($R^7$)$_2$NHC(O)—$R^8$;

$R^5$ represents up to 3 optional benzene ring substituents, each independently selected from halo, —CN, $C_1$-$C_6$ alkyl, $C_1$-$C_6$ haloalkyl, $C_3$-$C_7$ cycloalkyl, 4 to 6-membered monocyclic heterocycloalkyl, 5 or 6-membered monocyclic heteroaryl, $C_6$-$C_{10}$ aryl, benzyl and —O—($C_1$-$C_6$ alkyl), wherein said $C_3$-$C_7$ cycloalkyl group, said 4 to 6-membered monocyclic heterocycloalkyl group, said 5 or 6-membered monocyclic heteroaryl group, said $C_6$-$C_{10}$ aryl group, or the phenyl moiety of said benzyl group can be optionally substituted with up to 3 groups, which can be the same or different, and are selected from halo, —CN, $C_1$-$C_6$ alkyl, $C_1$-$C_6$ haloalkyl, —O—$C_1$-$C_6$ alkyl, —($C_1$-$C_6$ alkylene)-O—$C_1$-$C_6$ alkyl and —O—($C_1$-$C_6$ haloalkyl);

$R^6$ represents up to 3 optional substituents, each independently selected from halo, —CN, $C_1$-$C_6$ alkyl, $C_1$-$C_6$ haloalkyl, $C_3$-$C_7$ cycloalkyl, $C_6$-$C_{10}$ aryl, benzyl, —O—($C_1$-$C_6$ alkyl), $C_2$-$C_6$ alkenyl, $C_1$-$C_6$ hydroxyalkyl, —N($R^9$)$_2$, —($C_1$-$C_6$ alkylene)$_m$-($C_6$-$C_{10}$ aryl), —($C_1$-$C_6$ alkylene)$_m$-($C_3$-$C_7$ cycloalkyl), 5 or 6-membered monocyclic heteroaryl, and 9 or 10-membered bicyclic heteroaryl, wherein said 5 or 6-membered monocyclic heteroaryl group can be optionally substituted on a ring carbon atom with $C_1$-$C_6$ alkyl, $C_3$-$C_7$ cycloalkyl or phenyl, and optionally substituted on a ring nitrogen atom with $C_1$-$C_6$ alkyl; said $C_1$-$C_6$ alkyl, $C_3$-$C_7$ cycloalkyl or phenyl can be optionally substituted a ring carbon atom with halo, $C_1$-$C_6$ alkyl or $C_3$-$C_7$ cycloalkyl;

each occurrence of $R^7$ is independently selected from H, $C_1$-$C_6$ alkyl, $C_1$-$C_6$ haloalkyl, phenyl, 4 to 8-membered monocyclic heterocycloalkyl, 6 to 10-membered bicyclic heterocycloalkyl and $C_3$-$C_7$ cycloalkyl, wherein said 4 to 8-membered monocyclic heterocycloalkyl group, said 6 to 10-membered bicyclic heterocycloalkyl group and said $C_3$-$C_7$ cycloalkyl group can be optionally substituted with up to 5 groups, each independently selected from halo, —CN, $C_1$-$C_6$ alkyl, $C_1$-$C_6$ haloalkyl, $C_3$-$C_7$ cycloalkyl, —O—$C_1$-$C_6$ alkyl, —N($R^9$)$_2$ and —O—($C_1$-$C_6$ haloalkyl), and wherein said $C_3$-$C_7$ cycloalkyl group can be optionally fused to a 4 to 6-membered monocyclic heterocycloalkyl group, and wherein said 4 to 8-membered monocyclic heterocycloalkyl group and said $C_3$-$C_7$ cycloalkyl group can be substituted on a ring carbon atom with a spirocyclic $C_3$-$C_6$ cycloalkyl group; and wherein said $C_3$-$C_7$ cycloalkyl group can be substituted on a ring carbon atom with a spirocyclic 3 to 6-membered monocyclic heterocycloalkyl group, and wherein two $R^7$ groups, that are attached to a common carbon atom, together with the common carbon atom to which they are attached, join to form a $C_3$-$C_7$ cycloalkyl group;

each occurrence of $R^8$ is independently $C_1$-$C_6$ alkyl, $C_3$-$C_7$ cycloalkyl and $C_6$-$C_{10}$ aryl;

each occurrence of $R^9$ is independently selected from H, $C_1$-$C_6$ alkyl, $C_3$-$C_7$ cycloalkyl and $C_6$-$C_{10}$ aryl; and each occurrence of m is independently 0 or 1.

The Compounds of Formula (I) (also referred to herein as the "Heterocycle-Substituted Tetracyclic Compounds") and pharmaceutically acceptable salts thereof can be useful, for example, for inhibiting HCV viral replication or replicon activity, and for treating or preventing HCV infection in a patient. Without being bound by any specific theory, it is believed that the Heterocycle-Substituted Tetracyclic Compounds inhibit HCV viral replication by inhibiting HCV NS5A.

Accordingly, the present invention provides methods for treating or preventing HCV infection in a patient, comprising administering to the patient an effective amount of at least one Heterocycle-Substituted Tetracyclic Compound.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention relates to novel Heterocycle-Substituted Tetracyclic Compounds, compositions comprising at least one Heterocycle-Substituted Tetracyclic Compound, and methods of using the Heterocycle-Substituted Tetracyclic Compounds for treating or preventing HCV infection in a patient.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "effective amount" as used herein, refers to an amount of Heterocycle-Substituted Tetracyclic Compound and/or an additional therapeutic agent, or a composition thereof that is effective in producing the desired therapeutic, ameliorative, inhibitory or preventative effect when administered to a patient suffering from a viral infection or virus-related disorder. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HCV viral infection or HCV-virus related disorder, refers to reducing the likelihood of HCV infection.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene- O-alkyl, alkylthio, —NH₂, —NH(alkyl), —N(alkyl)₂, NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH₂, —NH(alkyl), —N(alkyl)₂, —NH(cycloalkyl), —O—C(O)-alkyl, —O—C(O)-aryl, —O—C(O)-cycloalkyl, —C(O)OH and —C(O)O-alkyl. The term "C₂-C₆ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH₂, —NH(alkyl), —N(alkyl)₂, —NH(cycloalkyl), —O—C(O)-alkyl, —O—C(O)-aryl, —O—C(O)-cycloalkyl, —C(O)OH and —C(O)O-alkyl. The term "C₂-C₆ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH₂—, —CH₂CH₂—, —CH₂CH₂CH₂—, —CH₂CH₂CH₂CH₂—, —CH(CH₃)CH₂CH₂—, —CH(CH₃)— and —CH₂CH(CH₃)CH₂—. In one embodiment, an alkylene group has from 1 to about 6 carbon atoms. In another embodiment, an alkylene group is branched. In another embodiment, an alkylene group is linear. In one embodiment, an alkylene group is —CH₂—. The term "C₁-C₆ alkylene" refers to an alkylene group having from 1 to 6 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 6-membered cycloalkyl" refers to a cycloalkyl group having from 3 to 6 ring carbon atoms. A ring carbon atom of a cycloalkyl group may be functionalized as a carbonyl group. Unless otherwise indicated, a cycloalkyl group is unsubstituted. An illustrative example of such a cycloalkyl group (also referred to herein as a "cycloalkanoyl" group) includes, but is not limited to, cyclobutanoyl:

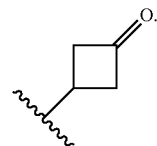 [SMILES: *C1CC(=O)C1]

The term "cycloalkenyl," as used herein, refers to a non-aromatic mono- or multicyclic ring system comprising from about 4 to about 10 ring carbon atoms and containing at least one endocyclic double bond. In one embodiment, a cycloalkenyl contains from about 4 to about 7 ring carbon atoms. In another embodiment, a cycloalkenyl contains 5 or 6 ring atoms. Non-limiting examples of monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. A ring carbon atom of a cycloalkyl group may be functionalized as a carbonyl group. In one embodiment, a cycloalkenyl group is cyclopentenyl. In another embodiment, a cycloalkenyl group is cyclohexenyl. The term "4 to 6-membered cycloalkenyl" refers to a cycloalkenyl group having from 4 to 6 ring carbon atoms. Unless otherwise indicated, an cycloalkenyl group is unsubstituted.

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH₂F, —CHF₂, —CF₃, —CH$_2$Cl and —CCl$_3$. The term "C$_1$-C$_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic and had 9 or 10 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heteroarylene," as used herein, refers to a bivalent group derived from an heteroaryl group, as defined above, by removal of a hydrogen atom from a ring carbon or ring heteroatom of a heteroaryl group. A heteroarylene group can be derived from a monocyclic or multicyclic ring system comprising about 5 to about 14 ring atoms, wherein from 1 to 4 of the ring atoms are each independently O, N or S and the remaining ring atoms are carbon atoms. A heteroarylene group can be optionally substituted by one or more "ring system substituents" which may be the same or different, and are as defined herein below. A heteroarylene group is joined via a ring carbon atom or by a nitrogen atom with an open valence, and any nitrogen atom of a heteroarylene can be optionally oxidized to the corresponding N-oxide. The term "heteroarylene" also encompasses a heteroarylene group, as defined above, which is fused to a benzene ring. Non-limiting examples of heteroarylenes include pyridylene, pyrazinylene, furanylene, thienylene, pyrimidinylene, pyridonylene (including those derived from N-substituted pyridonyls), isoxazolylene, isothiazolylene, oxazolylene, oxadiazolylene, thiazolylene, pyrazolylene, thiophenylene, furazanylene, pyrrolylene, triazolylene, 1,2,4-thiadiazolylene, pyrazinylene, pyridazinylene, quinoxalinylene, phthalazinylene, oxindolylene, imidazo[1,2-a]pyridinylene, imidazo[2,1-b]thiazolylene, benzofurazanylene, indolylene, azaindolylene, benzimidazolylene, benzothienylene, quinolinylene, imidazolylene, benzimidazolylene, thienopyridylene, quinazolinylene, thienopyrimidylene, pyrrolopyridylene, imidazopyridylene, isoquinolinylene, benzoazaindolylene, 1,2,4-triazinylene, benzothiazolylene and the like, and all isomeric forms thereof. The term "heteroarylene" also refers to partially saturated heteroarylene moieties such as, for example, tetrahydroisoquinolylene, tetrahydroquinolylene, and the like. A heteroarylene group is divalent and unless specified otherwise, either available bond on a heteroarylene ring can connect to either group flanking the heteroarylene group. For example, the group "A-heteroarylene-B," wherein the heteroarylene group is:

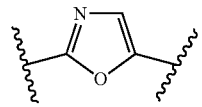 [SMILES: *c1cnc(*)o1]

is understood to represent both:

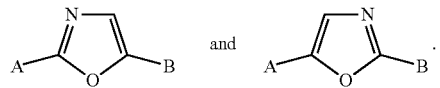

In one embodiment, a heteroarylene group is a monocyclic heteroarylene group or a bicyclic heteroarylene group. In another embodiment, a heteroarylene group is a monocyclic heteroarylene group. In another embodiment, a heteroarylene group is a bicyclic heteroarylene group. In still another embodiment, a heteroarylene group has from about 5 to about 10 ring atoms. In another embodiment, a heteroarylene group is monocyclic and has 5 or 6 ring atoms. In another embodiment, a heteroarylene group is bicyclic and has 9 or 10 ring atoms. In another embodiment, a heteroarylene group is a 5-membered monocyclic heteroarylene. In another embodiment, a heteroarylene group is a 6-membered monocyclic heteroarylene. In another embodiment, a bicyclic heteroarylene group comprises a 5 or 6-membered monocyclic heteroarylene group fused to a benzene ring. Unless otherwise indicated, a heteroarylene group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. Unless otherwise indicated, a heterocycloalkyl group is unsubstituted. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, silacyclopentane, silapyrrolidine and the like, and all isomers thereof. Non-limiting illustrative examples of a silyl-containing heterocycloalkyl group include:

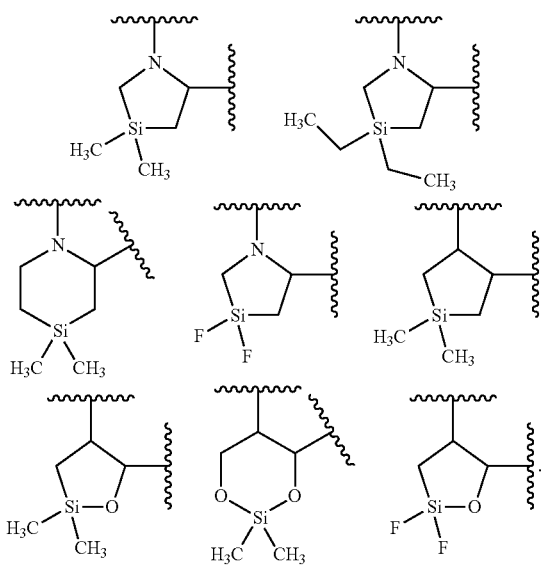

A ring carbon atom of a heterocycloalkyl group may be functionalized as a carbonyl group. An illustrative example of such a heterocycloalkyl group is:

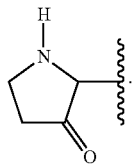

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic cycloalkyl" refers to a monocyclic heterocycloalkyl group having from 3 to 6 ring atoms. The term "4 to 6-membered monocyclic cycloalkyl" refers to a monocyclic heterocycloalkyl group having from 4 to 6 ring atoms. The term "7 to 11-membered bicyclic heterocycloalkyl" refers to a bicyclic heterocycloalkyl group having from 7 to 11 ring atoms. The term "heterocycloalkenyl," as used herein, refers to a heterocycloalkyl group, as defined above, wherein the heterocycloalkyl group contains from 4 to 10 ring atoms, and at least one endocyclic carbon-carbon or carbon-nitrogen double bond. A heterocycloalkenyl group can be joined via a ring carbon or ring nitrogen atom. In one embodiment, a heterocycloalkenyl group has from 4 to 6 ring atoms. In another embodiment, a heterocycloalkenyl group is monocyclic and has 5 or 6 ring atoms. In another embodiment, a heterocycloalkenyl group is bicyclic. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. A ring carbon atom of a heterocycloalkenyl group may be functionalized as a carbonyl group. Non-limiting examples of heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like and the like. In one embodiment, a heterocycloalkenyl group is a 5-membered heterocycloalkenyl. In another embodiment, a heterocycloalkenyl group is a 6-membered heterocycloalkenyl. The term "4 to 6-membered heterocycloalkenyl" refers to a heterocycloalkenyl group having from 4 to 6 ring atoms. Unless otherwise indicated, a heterocycloalkenyl group is unsubstituted.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, N.Y.

When any substituent or variable (e.g., $R^1$, m, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Heterocycle-Substituted Tetracyclic Compound or a pharmaceutically acceptable salt or solvate of the compound. The transformation may occur by various mechanisms (e.g., by metabolic or chemical processes), such as, for example, through hydrolysis in blood.

For example, if a Heterocycle-Substituted Tetracyclic Compound or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 6 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$ alkylcarbamoyl-$(C_1-C_2)$alkyl and piperidino-, pyrrolidino- or morpholino$(C_2-C_3)$alkyl, and the like.

Similarly, if a Heterocycle-Substituted Tetracyclic Compound contains an alcohol functional group, a prodrug can be formed by the replacement of the hydrogen atom of the alcohol group with a group such as, for example, $(C_1-C_6)$ alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkyl, α-amino $(C_1-C_4)$alkylene-aryl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1-C_6$)alkyl)$_2$ or glycosyl (the radical resulting from the removal of a hydroxyl group of the hemiacetal form of a carbohydrate), and the like.

If a Heterocycle-Substituted Tetracyclic Compound incorporates an amine functional group, a prodrug can be formed by the replacement of a hydrogen atom in the amine group with a group such as, for example, R-carbonyl-, RO-carbonyl-, NRR'-carbonyl- wherein R and R' are each independently $(C_1-C_{10})$alkyl, $(C_3-C_7)$ cycloalkyl, benzyl, a natural α-aminoacyl, —C(OH)C(O)OY$^1$ wherein Y$^1$ is H, $(C_1-C_6)$ alkyl or benzyl, —C(OY$^2$)Y$^3$ wherein Y$^2$ is $(C_1-C_4)$ alkyl and Y$^3$ is $(C_1-C_6)$alkyl; carboxy $(C_1-C_6)$alkyl; amino$(C_1-C_4)$alkyl or mono-N- or di-N,N—$(C_1-C_6)$alkylaminoalkyl; —C(Y$^4$)Y$^5$ wherein Y$^4$ is H or methyl and Y$^5$ is mono-N- or di-N,N—$(C_1-C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di $(C_{6-24})$acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Techours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Heterocycle-Substituted Tetracyclic Compounds can form salts which are also within the scope of this invention. The term "salt(s)", as employed herein, denotes acidic salts formed with inorganic and/or organic acids, as well as basic salts formed with inorganic and/or organic bases. In addition, when a Heterocycle-Substituted Tetracyclic Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Heterocycle- Substituted Tetracyclic Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Heterocycle-Substituted Tetracyclic Compounds may be atropisomers (e.g., substituted biaryls) and are considered as part of this invention. Enantiomers can also be directly separated using chiral chromatographic techniques.

It is also possible that the Heterocycle-Substituted Tetracyclic Compounds may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Heterocycle-Substituted Tetracyclic Compound incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Heterocycle-Substituted Tetracyclic Compounds, and of the salts, solvates, hydrates, esters and prodrugs of the Heterocycle-Substituted Tetracyclic Compounds, are intended to be included in the present invention.

The following abbreviations are used below and have the following meanings: Ac is acyl; Aq is aqueous; BOC or Boc is tert-butyloxycarbonyl; Boc$_2$O is Boc anhydride; n-Bu-PACl$_2$ is admantyl n-butylphosphine dichloride; t-Bu is tertiary butyl; t-BuOK is potassium tert-butoxide; Celite is diatomaceous earth; DCM is dichloromethane; DDQ is 2,3-dichloro-5,6-dicyano-1,4-benzoquinone; Dess-Martin reagent is 1,1-Triacetoxy-1,1-dihydro-1,2-benziodoxol-3 (1H)-one; DIBAL is diisobutylaluminum hydride; DIPEA is diisopropylethylamine; DME is dimethoxyethane; DMF is N,N-dimethylformamide; dppf is diphenylphosphinoferrocene; DMSO is dimethylsulfoxide; ESI is electrospray ionization; EtOAc is ethyl acetate; HATU is O—(7-azabenzotriazol-1-yl)-N,N,N',N'-tetramethyluronium hexafluorophosphate; HPLC is high performance liquid chromatographyKOAc is potassium acetate; LCMS is liquid chromatography/mass spectrometry; LiHMDS is lithium hexamethyldisilazide; MeCN is acetonitrile; Me is methyl;

MeOH is methanol; MS is mass spectrometry; NBS is N-bromosuccinimide; NCS is N-chlorosuccinimide; PCR is polymerase chain reaction; Pd/C is palladium on carbon; Pd(PPh$_3$)$_4$ is tetrakis (triphenylphosphine)palladium(O); Pd(dppf)$_2$Cl$_2$ is [1,1'-Bis(diphenylphosphino)ferrocene] dichloro palladium(II); RT-PCR is reverse transcription polymerase chain reaction; SFC is supercritical flow chromatography; TFA is trifluoroacetic acid; THF is tetrahydrofuran; TLC is thin-layer chromatography; and XPhos is 2-dicyclohexylphosphino-2', 4',6'-triisopropylbiphenyl.

The Compounds of Formula (I)

The present invention provides Heterocycle-Substituted Tetracyclic Compounds of

Formula (I):

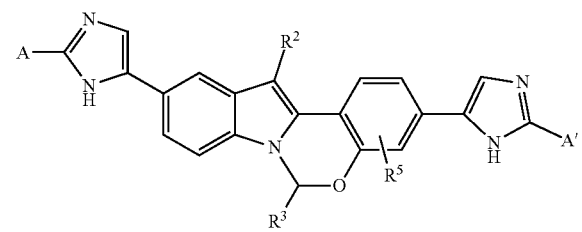

(I)

and pharmaceutically acceptable salts thereof, wherein A, A', R$^2$, R$^3$, R$^4$ and R$^5$ are defined above for the Compounds of Formula (I).

In one embodiment, R$^2$ is H

In another embodiment, R$^2$ is halo.

In another embodiment, R$^2$ is C$_1$-C$_6$ alkyl.

In one embodiment, R$^5$ is present and represents one F substituent.

In another embodiment, R$^5$ is absent.

In one embodiment, A and A' are each a 5-membered heterocycloalkyl group.

In another embodiment, A and A' are each a 6-membered heterocycloalkyl group.

In another embodiment, A and A' are each independently selected from:

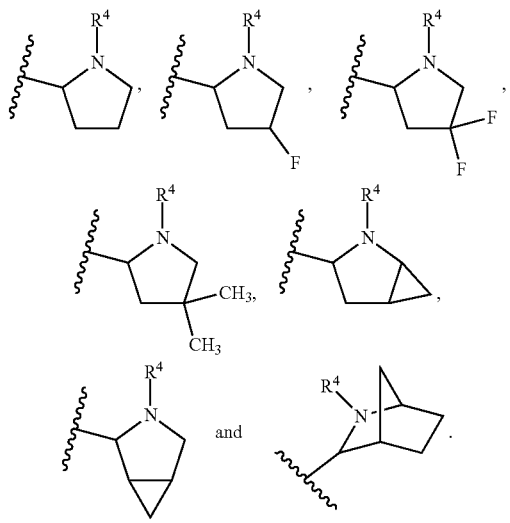

In still another embodiment, A and A' are each independently selected from:

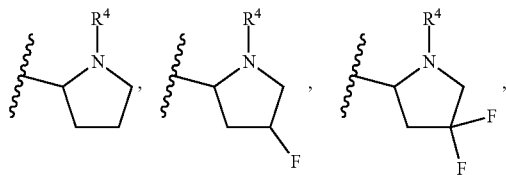

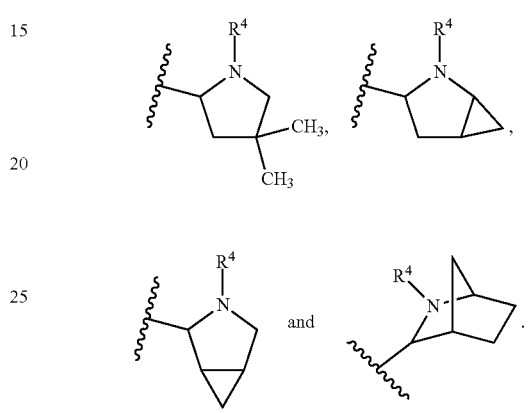

In another embodiment, A and A' are each independently selected from:

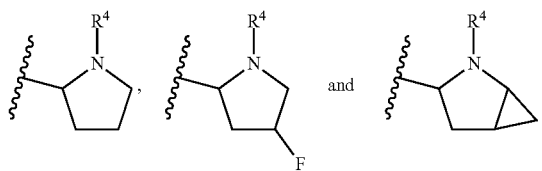

In another embodiment, A and A' are each independently:

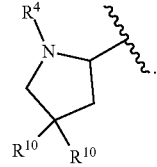

In another embodiment, A and A' are each independently:

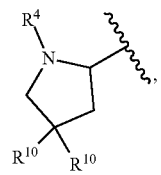

wherein each occurrence of R$^{10}$ is independently H, CH$_3$, or F.

In one embodiment, each occurrence of R⁴ is independently:

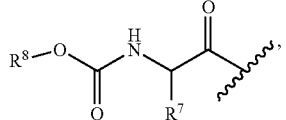

wherein R⁷ is selected from $C_1$-$C_6$ alkyl, $C_1$-$C_6$ haloalkyl and 4 to 6-membered monocyclic heterocycloalkyl, wherein said 4 to 6-membered monocyclic heterocycloalkyl group can be optionally substituted with up to five groups, each independently selected from halo, $C_1$-$C_6$ alkyl and $C_3$-$C_7$ cycloalkyl, and wherein said 4 to 6-membered monocyclic heterocycloalkyl group can be optionally substituted on a ring carbon atom with a spirocyclic $C_3$-$C_6$ cycloalkyl group; and R⁸ is $C_1$-$C_6$ alkyl.

In one embodiment, each occurrence of R⁴ is independently:

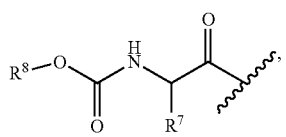

wherein R⁷ is selected from isopropyl,

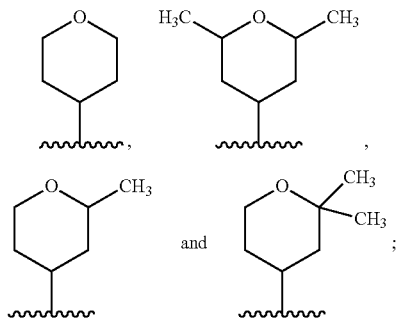

and R⁸ is $C_1$-$C_6$ alkyl.

In another embodiment, each occurrence of R⁴ is independently:

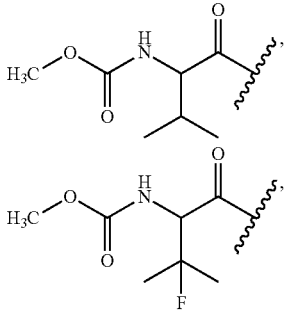

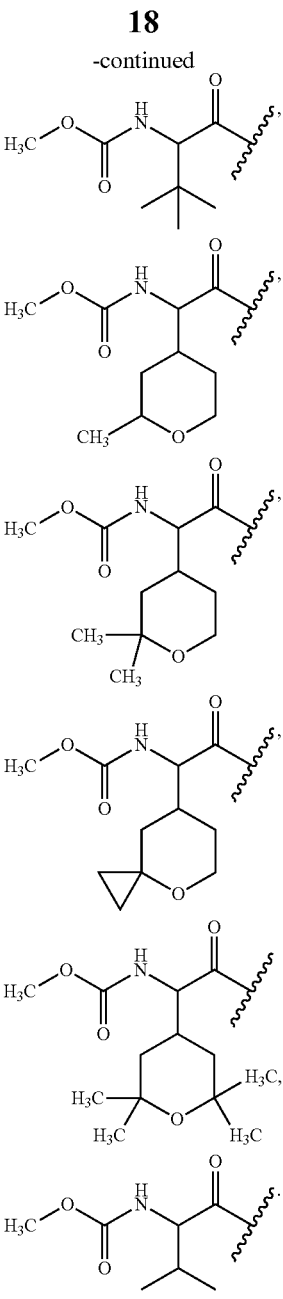

In one embodiment, A and A' are each independently selected from:

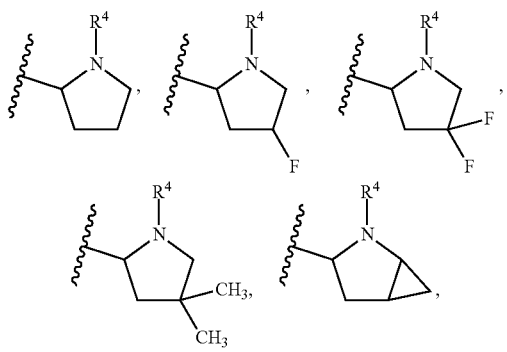

-continued

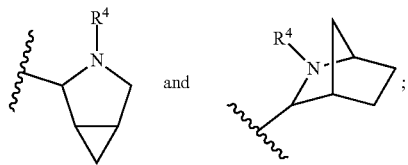
and and each occurrence of $R^4$ is independently:

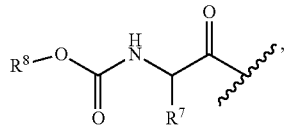

wherein $R^7$ is selected from isopropyl,

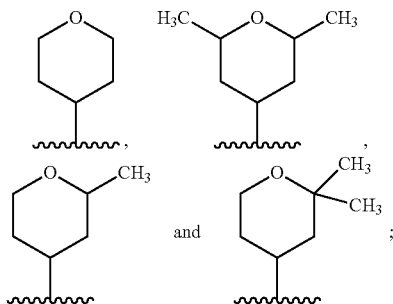
and and $R^8$ is $C_1$-$C_6$ alkyl.

In another embodiment, A and A' are each independently selected from:

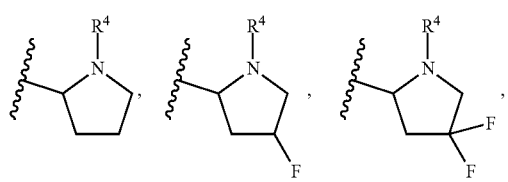

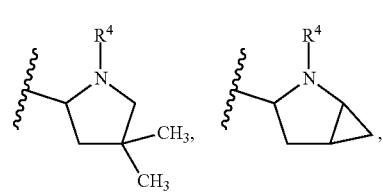

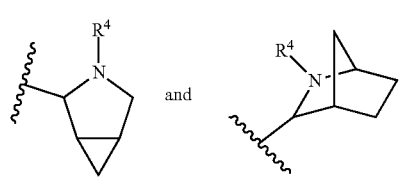
and and $R^4$ is:

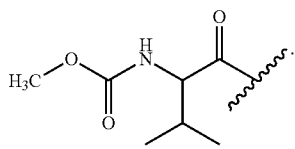 [SMILES: *C(=O)C(NC(=O)OC)C(C)C]

In yet another embodiment, A and A' are each:

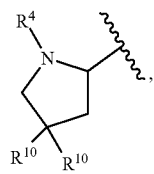

wherein each occurrence of $R^{10}$ is independently H, $CH_3$, or F; each occurrence of $R^4$ is independently:

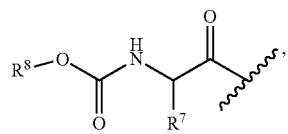

wherein $R^7$ is selected from isopropyl,

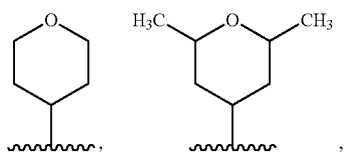

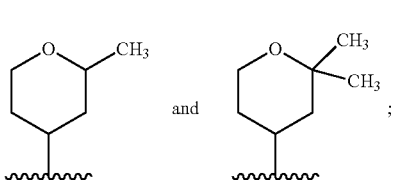
and and $R^8$ is $C_1$-$C_6$ alkyl.

In another embodiment, A and A' are each independently selected from:

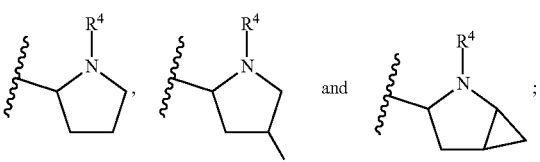

each occurrence of R[4] is independently:

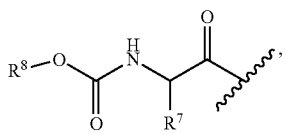

wherein R[7] is selected from isopropyl,

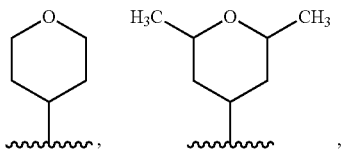

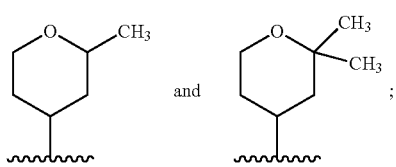

and R[8] is methyl.

In another embodiment, A and A' are each independently selected from:

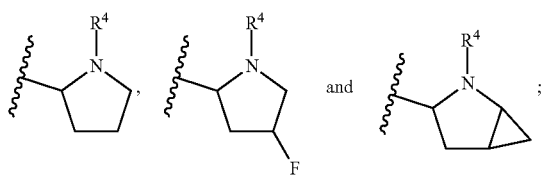

each occurrence of R[4] is independently:

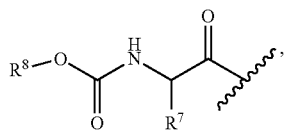

wherein R[7] is selected from isopropyl and

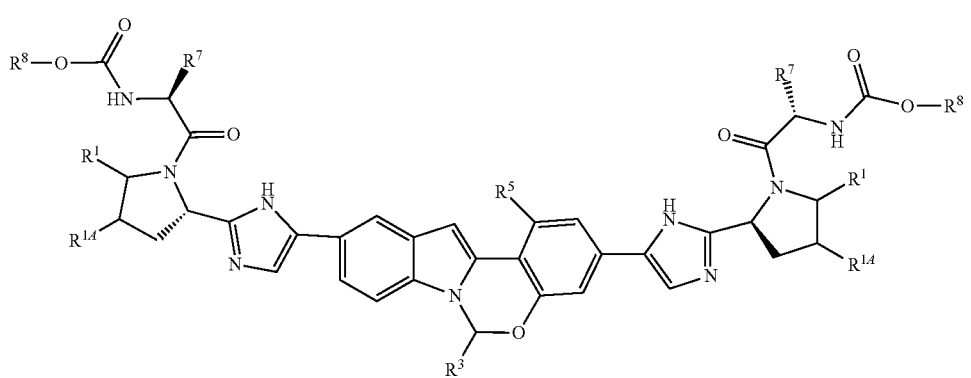

and R[8] is methyl.

In one embodiment, variables A, A', R[2], R[3], R[4] and R[5] for the Compounds of Formula (I) are selected independently of each other.

In another embodiment, the Compounds of Formula (I) are in substantially purified form.

In one embodiment, the Compounds of Formula (I) have the formula (Ia):

(Ia)

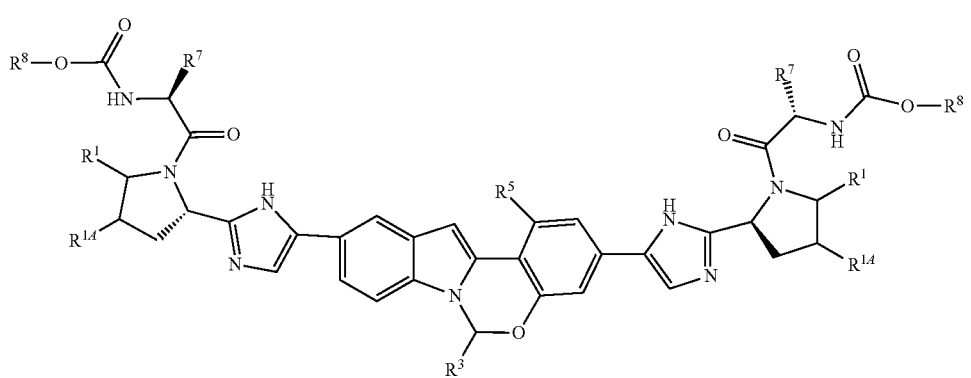

or a pharmaceutically acceptable salt thereof,
wherein:

each $R^1$ is H;

each $R^{1A}$ is independently H or F, or an $R^{1A}$ group and an $R^1$ group that are attached to same ring, together with the ring carbon atoms to which they are attached, can combine to form a fused cyclopropyl group;

$R^3$ is selected from furanyl, oxazolyl, oxadiazolyl, isoxazolyl, imidazolyl, benzoxazolyl, benzisoxazolyl, benzimidazolyl, pyrazolo[1,5-a]pyridinyl, imidazo[1,2-a]pyridinyl, 6,7-dihydro-5H-pyrrolo[1,2-a]imidazolyl, 1,3,4-thiadiazolyl and 1,2,3-thiadiazolyl, wherein said furanyl, oxazolyl, oxadiazolyl, isoxazolyl, imidazolyl, benzoxazolyl, benzisoxazolyl, benzimidazolyl, pyrazolo[1,5-a]pyridinyl, imidazo[1,2-a]pyridinyl, 6,7-dihydro-5H-pyrrolo[1,2-a]imidazolyl, 1,3,4-thiadiazolyl and 1,2,3-thiadiazolyl groups can be optionally substituted a ring carbon atom with $C_1$-$C_6$ alkyl, $C_3$-$C_7$ cycloalkyl or phenyl, and optionally substituted on a ring nitrogen atom with $C_1$-$C_6$ alkyl; said $C_1$-$C_6$ alkyl, $C_3$-$C_7$ cycloalkyl or phenyl can be optionally substituted a ring carbon atom with halo, $C_1$-$C_6$ alkyl or $C_3$-$C_7$ cycloalkyl;

$R^5$ is H or F; and each occurrence of $R^7$ is independently selected from $C_1$-$C_6$ alkyl, $C_1$-$C_6$ haloalkyl, and 4 to 6-membered monocyclic heterocycloalkyl, wherein said 4 to 6-membered monocyclic heterocycloalkyl group can be optionally substituted with up to 5 groups, each independently selected from halo, $C_1$-$C_6$ alkyland $C_3$-$C_7$ cycloalkyl.

In one embodiment, variables $R^1$, $R^{1A}$, $R^3$, $R^5$, $R^7$ and $R^8$ for the Compounds of Formula (Ia) are selected independently of each other.

In another embodiment, the Compounds of Formula (Ia) are in substantially purified form.

In one embodiment, for the compounds of formula (I) or (Ia), $R^3$ is selected from:

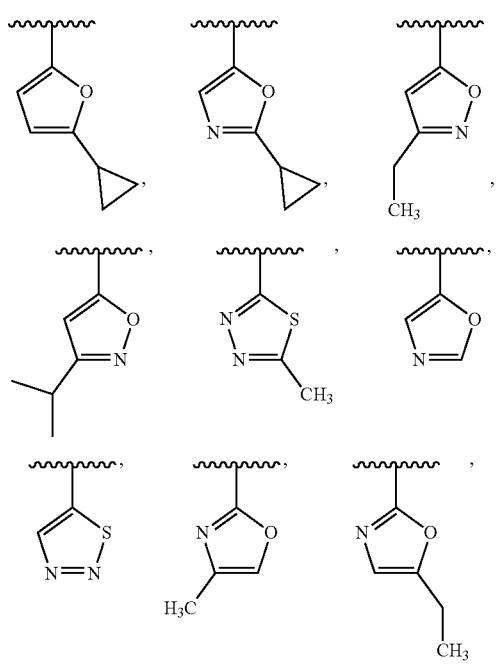

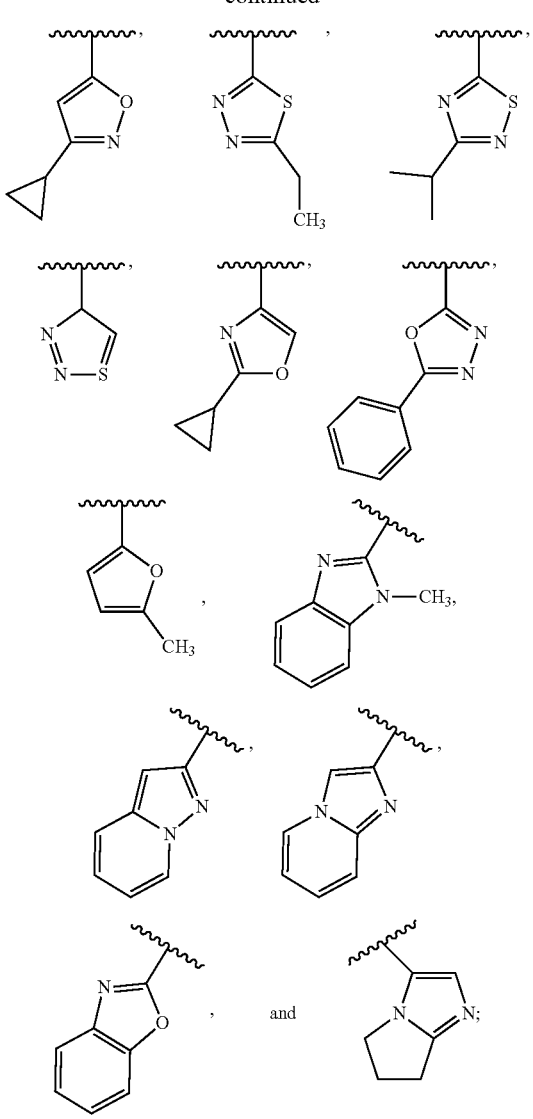

In one embodiment, for the compounds of formula (I) or (Ia), each occurrence of $R^7$ is isopropyl,

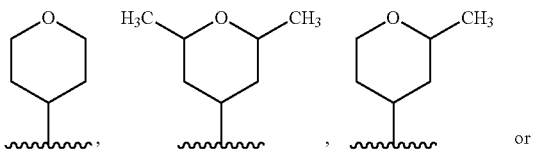

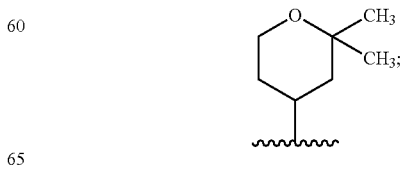

and each occurrence of $R^8$ is $C_1$-$C_6$ alkyl.

In another embodiment, for the compounds of formula (I) or (Ia), each occurrence of $R^7$ is isopropyl or

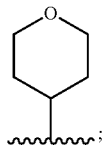

and each occurrence of $R^8$ is methyl.

In another embodiment, for the compounds of formula (I) or (Ia), $R^3$ is selected from:

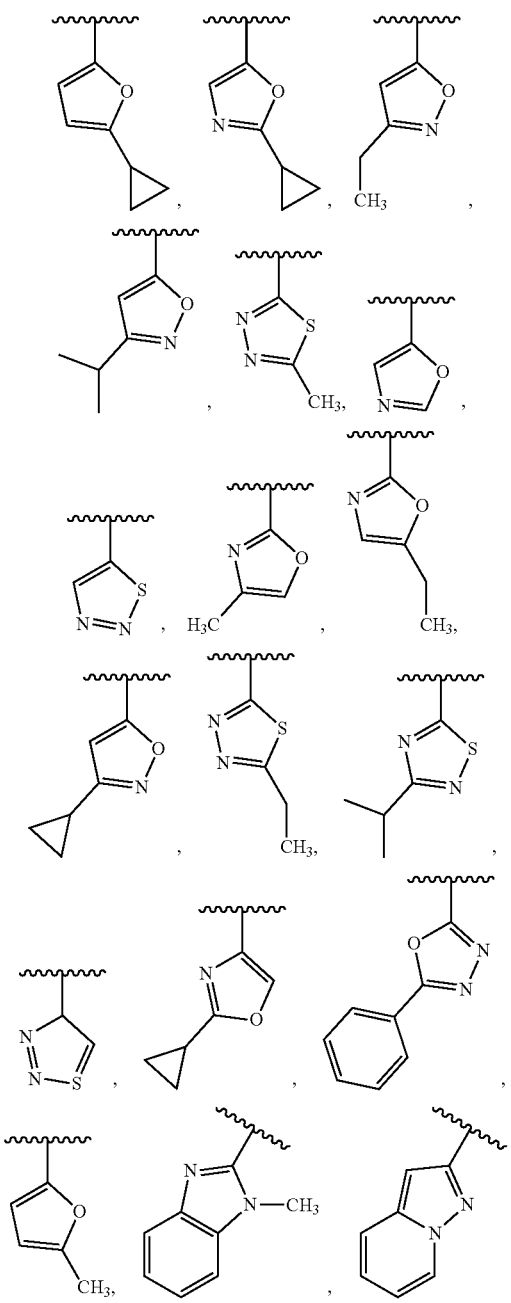

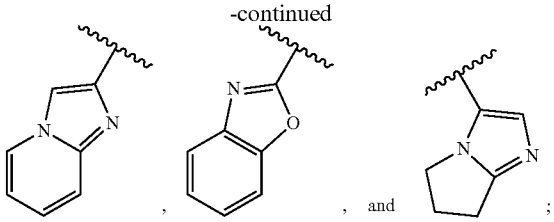

$R^5$ is absent;

each occurrence of $R^7$ is isopropyl or

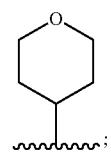 [SMILES: *C1CCOCC1]

and each occurrence of $R^8$ is methyl.

In another embodiment, for the compounds of formula (I) or (Ia), $R^3$ is selected from:

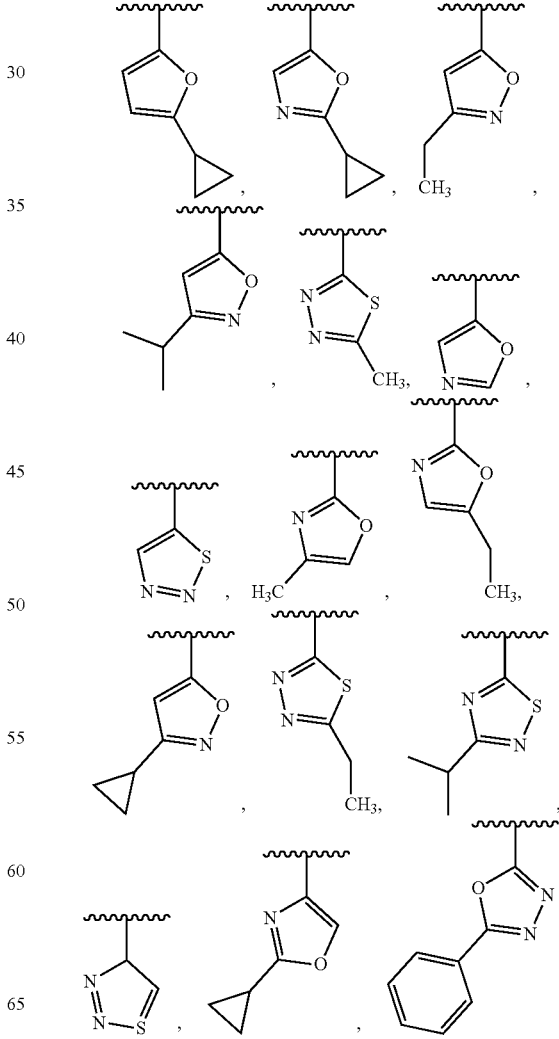

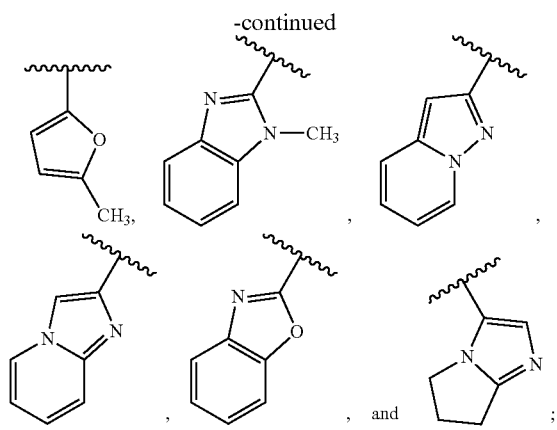

R[5] is F;
each occurrence of R[7] is isopropyl or

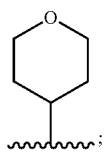 [SMILES: *C1CCOCC1]

and each occurrence of R[8] is methyl.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors and HCV NS5B polymerase inhibitors.

(d) A pharmaceutical combination that is (i) a Compound of Formula (I) and (ii) a second therapeutic agent selected from the group consisting of HCV antiviral agents, immunomodulators, and anti-infective agents; wherein the Compound of Formula (I) and the second therapeutic agent are each employed in an amount that renders the combination effective for inhibiting HCV replication, or for treating HCV infection and/or reducing the likelihood or severity of symptoms of HCV infection.

(e) The combination of (d), wherein the HCV antiviral agent is an antiviral selected from the group consisting of HCV protease inhibitors and HCV NS5B polymerase inhibitors.

(f) A method of inhibiting HCV replication in a subject in need thereof which comprises administering to the subject an effective amount of a Compound of Formula (I).

(g) A method of treating HCV infection and/or reducing the likelihood or severity of symptoms of HCV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors and HCV NS5B polymerase inhibitors.

(j) A method of inhibiting HCV replication in a subject in need thereof which comprises administering to the subject the pharmaceutical composition of (a), (b) or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine; (b) inhibiting HCV replication or (c) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

It is further to be understood that the embodiments of compositions and methods provided as (a) through (k) above are understood to include all embodiments of the compounds, including such embodiments as result from combinations of embodiments.

Non-limiting examples of the Compounds of Formula (I) include compounds 1-45, as set forth in the Examples below, and pharmaceutically acceptable salts thereof Methods For Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes 1-4 below. Alternative synthetic pathways and analogous structures will be apparent to those skilled in the art of organic synthesis.

Scheme 1 shows methods useful for making the compounds of formula G3, which are useful interemediates for making the Compounds of Formula (I).

Scheme 1

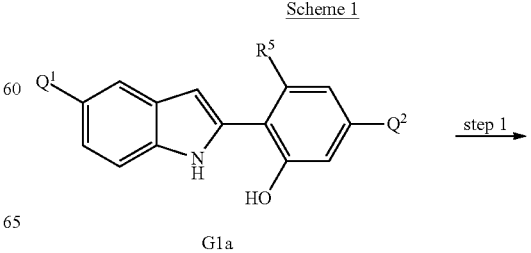

G1a

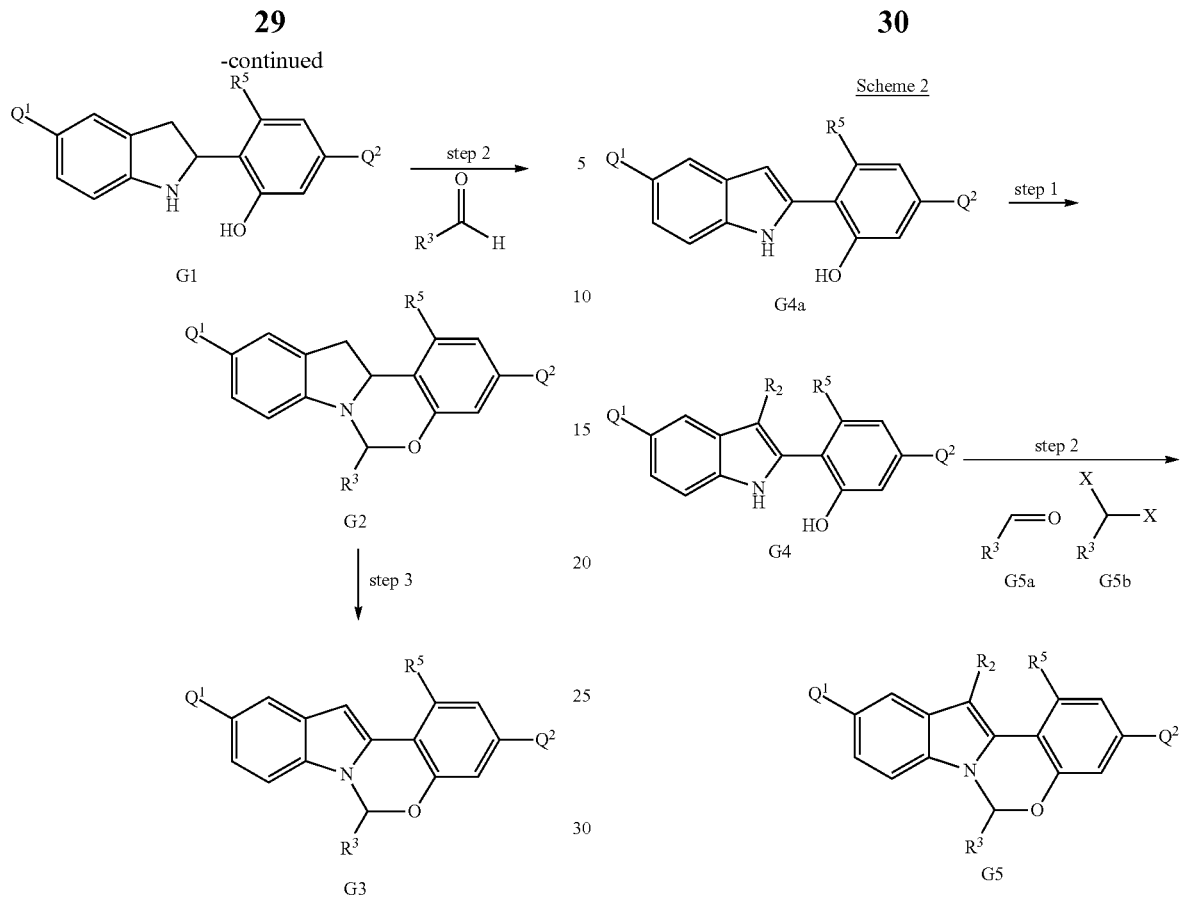

Wherein $R^3$ and $R^5$ are defined above for the Compounds of Formula (I) and $Q^1$ and $Q^2$ are each independently halo, hydroxyl, or a protected hydroxyl group, such as a methoxy or benzyloxy group.

An indole compound of formula G1a (which can be prepared as described in International Publication No. WO 2012/040923) can be treated with tin in concentrated HCl/EtOH solution to provide compounds of formula G1. A compound of formula G1 can be reacted with an aldehyde of formula $R^3$CHO in the presence of an acid to provide tetracyclic compounds of formula G2. Compounds of formula G2 can then be oxidized to provide the tetracyclic compounds of formula G3.

Scheme 2 shows methods useful for making the compounds of formula G5, which are useful interemediates for making the Compounds of Formula (I).

Wherein $R^2$ is halo, $R^3$ and $R^5$ are defined above for the Compounds of Formula (I), X is halo, and $Q^1$ and $Q^2$ are each independently halo, hydroxyl, or a protected hydroxyl group, such as a methoxy or benzyloxy group.

A compound of formula G4a (which can be prepared as described in International Publication No. WO 2012/040923) can be halogenated to provide the compounds of formula G4, wherein $R^2$ is halo. A compound of formula G4 can then be converted to the compounds of formula G5 via reaction with an aldehyde of formula G5a in the presence of an acid, or alternatively, by reaction with a dihalo compound of formula G5b in the presence of a base. The $R^2$ group of the compounds of formula G5 can be further elaborated using methods well-known in the art of organic synthesis to make the entire scope of variable $R^2$.

Scheme 3 shows methods useful for making the compounds of formula G12, which are useful interemediates for making the Compounds of Formula (I).

Scheme 3

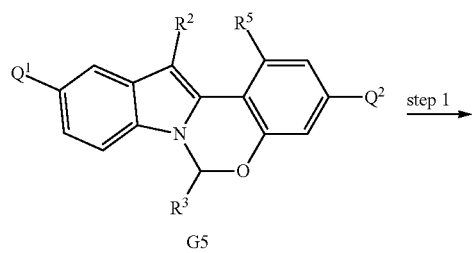

-continued
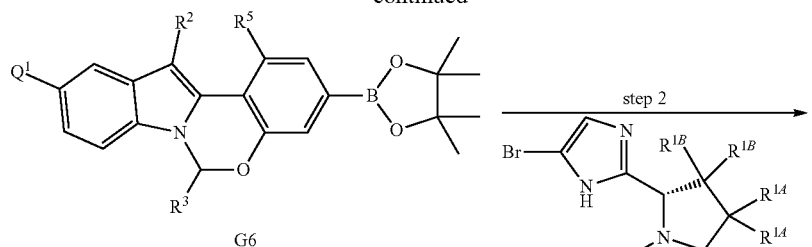
G6
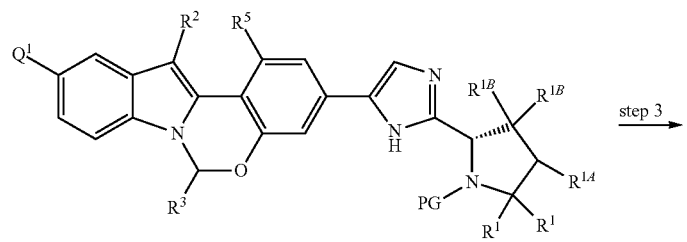
G8
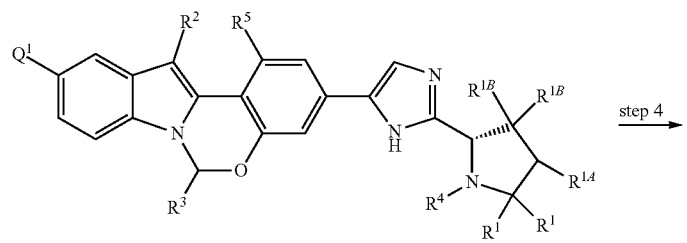
G9
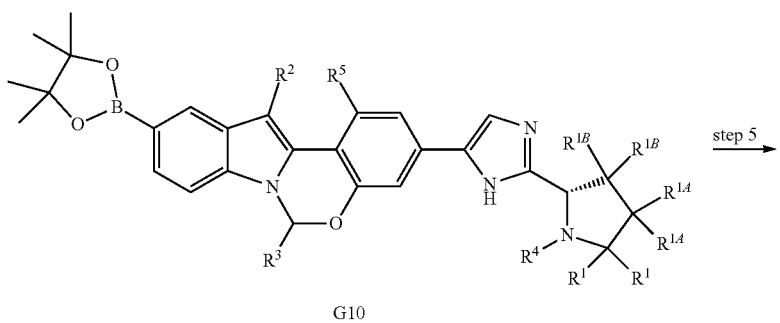
G10
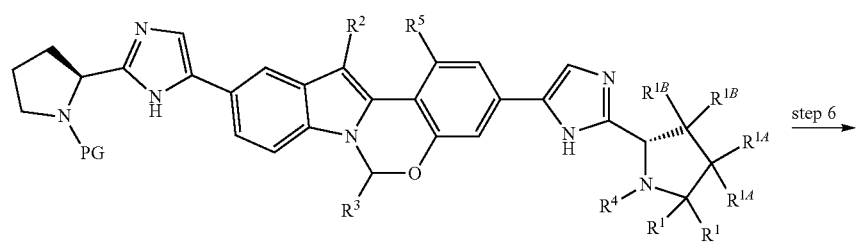
G11

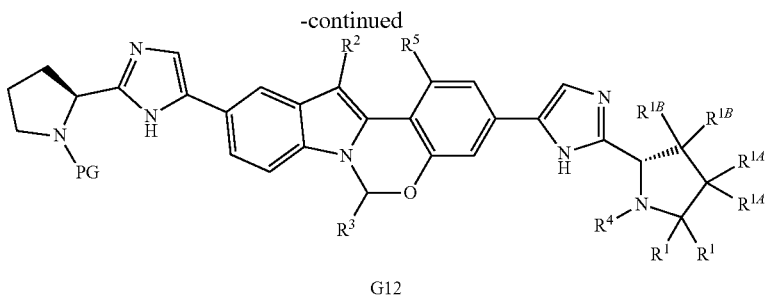

G12

Wherein R², R³, R⁴ and R⁵ are defined above for the Compounds of Formula (I), PG is a secondary amino protecting group, and Q¹ and Q² are each independently halo, hydroxyl, or a protected hydroxyl group, such as a methoxy or benzyloxy group.

A compound of formula G5 can be reacted with bis(pinacolato)diboron to provide the compounds of formula G6. A compound of formula G6 can then undergo a Pd-mediated coupling with a bromo compound of formula G7 (prepared as described in International Publication No. WO 2012/040923) to provide the compounds of formula G8. Compounds of formula G8 can then be deprotected and subjected to an amide coupling with a desired cap compound to provide a compound of formula G9. A compound of formula G9 is then subjected to a Pd-mediated coupling with bis(pinacolato)diboron to provide the boronic ester compounds of formula G10. A compound of formula G10 can then undergo a Pd-mediated coupling with a bromo compound of formula G7 (prepared as described in International Publication No. WO 2012/040923) to provide the compounds of formula G11. Compounds of formula G11 can then be deprotected and subjected to an amide coupling with a desired cap compound to provide a compound of formula G12.

Distereoisomers of the synthetic intermediates and final products can be separated using SFC or HPLC with chiral columns.

Scheme 4 shows methods useful for making the compounds of formula G18, which correspond to the Compounds of Formula (I).

Scheme 4

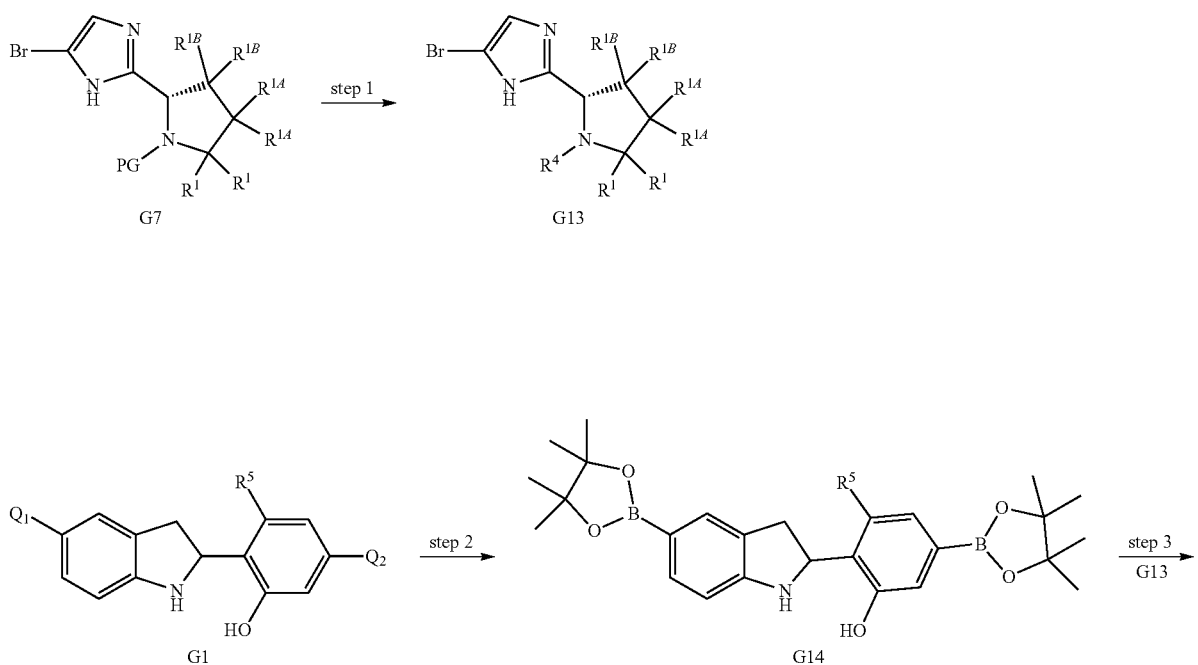

-continued

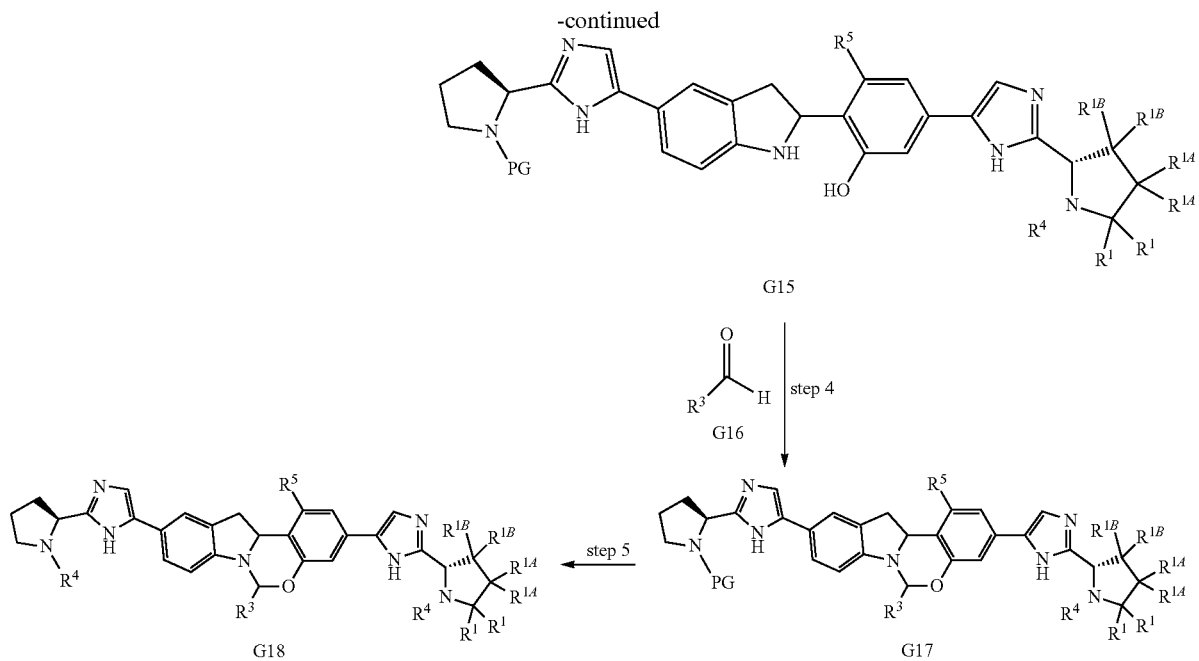

Wherein $R^3$, $R^4$ and $R^5$ are defined above for the Compounds of Formula (I), PG is a secondary amino protecting group, and $Q^1$ and $Q^2$ are each independently halo, hydroxyl, or a protected hydroxyl group, such as a methoxy or benzyloxy group.

A compound of formula G7 can be deprotected and subjected to an amide coupling with a desired cap compound to provide an intermediate bromoimidazole compound of formula G13. A compound of formula G1 can be converted to compound of formula G14 via a Pd-mediated coupling reaction with bis(pinacolato)diboron. The compound of formula G14 can then be subjected to a Pd-mediated coupling with a comound of formula G13 to provide a compound of formula G15. The compound of formula G15 can then be converted a compound of formula G17 via reaction with an aldehyde of formula G16 in the presence of an acid. The compound of formula G17 can then be subjected to an oxidative cyclization to provide the tetracyclic compounds of formula G18. The distereoisomers of G18 can be separated using, for example, SFC and employing chiral columns.

One skilled in the art of organic synthesis will recognize that the synthesis of fused tetracyclic cores contained in Compounds of Formula (I) may require protection of certain functional groups (i.e., derivatization for the purpose of chemical compatibility with a particular reaction condition). Suitable protecting groups for the various functional groups of these Compounds and methods for their installation and removal are well known in the art of organic chemistry. A summary of many of these methods can be found in Greene et al., *Protective Groups in Organic Synthesis*, Wiley-Interscience, New York, (1999).

One skilled in the art of organic synthesis will also recognize that one route for the synthesis of the fused tetracyclic cores of the Compounds of Formula (I) may be more desirable depending on the choice of appendage substituents. Additionally, one skilled in the art will recognize that in some cases the order of reactions may differ from that presented herein to avoid functional group incompatibilities and thus adjust the synthetic route accordingly.

One skilled in the art of organic synthesis will recognize that the synthesis of certain fused tetracyclic cores of the Compounds of Formula (I) require the construction of an amide bond. Methods useful for making such amide bonds, include but are not limited to, the use of a reactive carboxy derivative (e.g., an acid halide, or ester at elevated temperatures) or the use of an acid with a coupling reagent (e.g., HOBt, EDCI, DCC, HATU, PyBrop) with an amine.

The preparation of multicyclic intermediates useful for making the fused tetracyclic ring systems of the Compounds of Formula (I) have been described in the literature and in compendia such as "Comprehensive Heterocyclic Chemistry" editions I, II and III, published by Elsevier and edited by A. R. Katritzky & R. J K Taylor. Manipulation of the required substitution patterns have also been described in the available chemical literature as summarized in compendia such as "Comprehensive Organic Chemistry" published by Elsevier and edited by D H R. Barton and W. D. Ollis; "Comprehensive Organic Functional Group Transformations" edited by edited by A. R. Katritzky & R. J K Taylor and "Comprehensive Organic Transformation" published by Wily-CVH and edited by R. C. Larock.

The Compounds Formula (I) may contain one or more silicon atoms. The Compounds contemplated in this invention in general can be prepared using the carba-analog methodology unless otherwise noted. A recent review of the synthesis of silicon containing Compounds can be found in "Silicon Chemistry: from Atom to Extended Systems", Ed P. Jutzi & U. Schubet; ISBN 978-3-527-30647-3. Preparation of silyl containing amino acids has been described. See Bolm et al., *Angew. Chem. Int Ed.*, 39:2289 (2000). Descriptions of improved cellular update (Giralt, J. Am. Chem. Soc., 128:8479 (2006)) and reduced metabolic processing of silyl containing Compounds have been described (Johansson et al., *Drug Metabolism & Disposition*, 38:73 (2009)).

The starting materials used and the intermediates prepared using the methods set forth in Schemes 1-4 may be isolated and purified if desired using conventional techniques, including but not limited to filtration, distillation, crystallization, chromatography and alike. Such materials can be characterized using conventional means, including physical constants and spectral data.

One skilled in the art will be aware of standard formulation techniques as set forth in the open literature as well as in textbooks such as Zheng, "Formulation and Analaytical Development for Low-dose Oral Drug Products", Wiley, 2009, ISBN.

EXAMPLES

General Methods

Solvents, reagents, and intermediates that are commercially available were used as received. Reagents and intermediates that are not commercially available were prepared in the manner as described below. $^1$HNMR spectra were obtained on a Bruker Avance 500 (500 MHz) and are reported as ppm downfield from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 minutes—10% CH$_3$CN, 5 minutes—95% CH$_3$CN, 5-7 minutes—95% CH$_3$CN, 7 minutes—stop. The retention time and observed parent ion are given. Flash column chromatography was performed using pre-packed normal phase silica from Biotage, Inc. or bulk silica from Fisher Scientific. Unless otherwise indicated, column chromatography was performed using a gradient elution of hexanes/ ethyl acetate, from 100% hexanes to 100% ethyl acetate.

The following intermediate compounds were prepared using the methods described in International Publication Nos. WO 14/110705 and WO 14/110706.

core-1

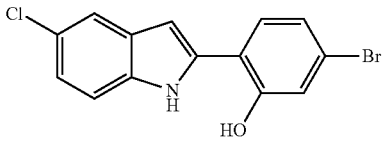

core-2 core-3 core-4

-continued core-5

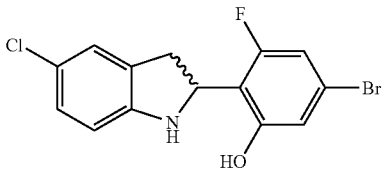

core-6 core-7

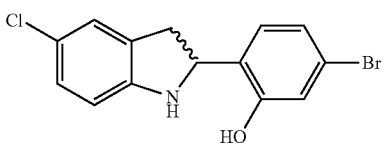

cap-1

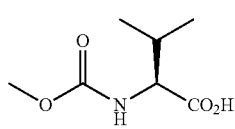

cap-2

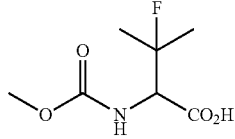

cap-3

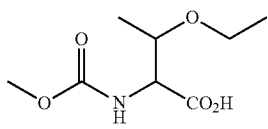

cap-4

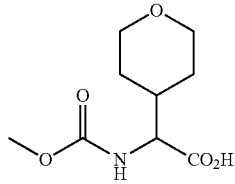

cap-5

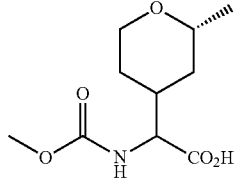

cap-6

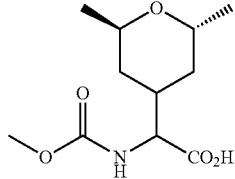

-continued
cap-7
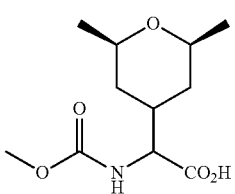
cap-8
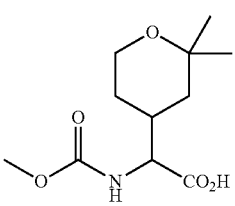
cap-9
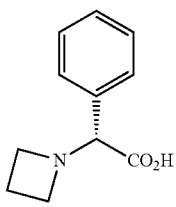
cap-10
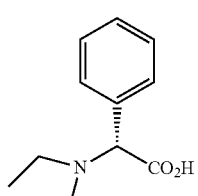
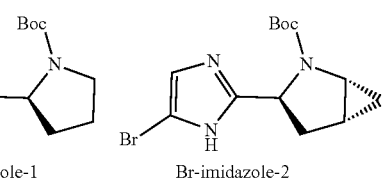
Br-imidazole-1    Br-imidazole-2
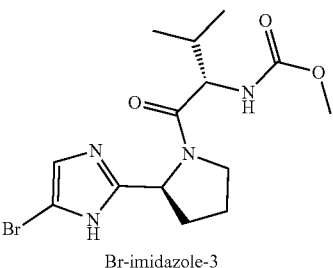
Br-imidazole-3
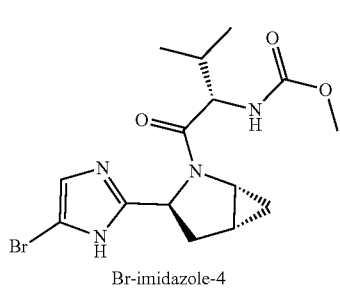
Br-imidazole-4
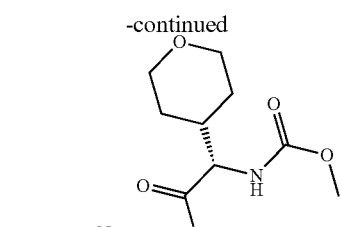
Br-imidazole-5
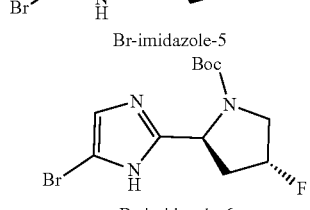
Br-imidazole-6
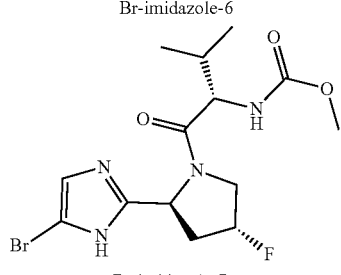
Br-imidazole-7
Example 1
Synthesis of Intermediate Compound 1D
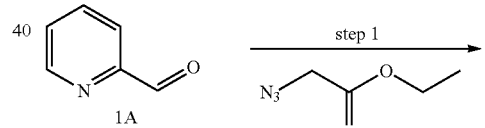
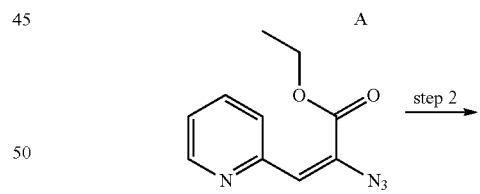
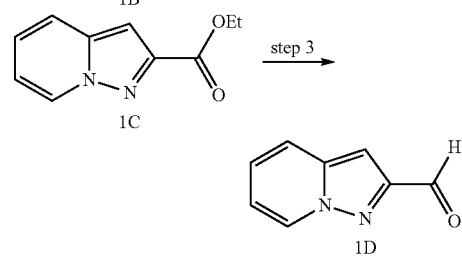
Step 1
To a solution of compound 1A (7.6 g, 70.7 mmol) and compound A (36.5 g, 283 mmol) in EtOH (100 mL) was added a solution of sodium (6.5 g, 283 mmol) in EtOH (150 mL) and the resulting suspension was allowed to stir at room temperature overnight. The reaction mixture was then added to water and extracted with ethyl acetate. The organic layer was dried over sodium sulfate, filtered and concentrated in vacuo, and the residue obtained was purified using flash column chromatography on silica gel to provide intermediate compound 1B. MS (ESI) m/z (M+H)+: 219.

Step 2

A solution of intermediate compound 1B (700 mg, 3.2 mmol) in toluene (20 mL) was allowed to stir for 4 hours at reflux. The reaction was concentrated in vacuo, and the residue obtained was purified using flash column chromatography on silica gel to provide intermediate compound 1C. MS (ESI) m/z (M+H)+: 191.

Step 3

To a solution of intermediate compound 1C (2.9 g, 15.3 mmol) in DCM (50 mL) at 0° C. was added DIBAL (23 mL, 23 mmol). The reaction was allowed to stir at room temperature overnight under $N_2$ atmosphere, then the reaction mixture was concentrated in vacuo. The residue obtained was taken up in DCM (200 mL), washed with brine, dried over anhydrous sodium sulfate, filtered and concentrated in vacuo to provide intermediate compound 1D. MS (ESI) m/z (M+H)+: 147.

Example 2

Synthesis of Intermediate Compound 2B

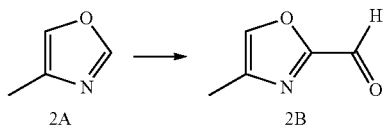

To a solution of compound 2A (4.5 g, 54.2 mmol) in 60 mL of dry THF at −78° C. under a nitrogen atmosphere was added 1.1 equiv. of n-BuLi (2.5 M in THF) in THF and the reaction was allowed to stir for 45 minutes. DMF (3.96 g, 54.2 mmol) was added, and the reaction was allowed to stand overnight and warm to room temperature. The reaction mixture was then neutralized with 2N HCl and extracted with DCM (50 mL). The organic combined phases were combined, dried over $Na_2SO_4$, filtered, and concentrated in vacuo to provide intermediate compound 2B, which was used without further purification.

Example 3

Synthesis of Intermediate Compound 3C

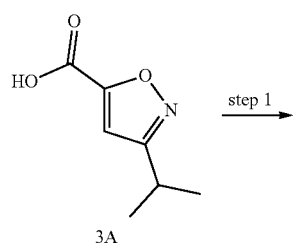

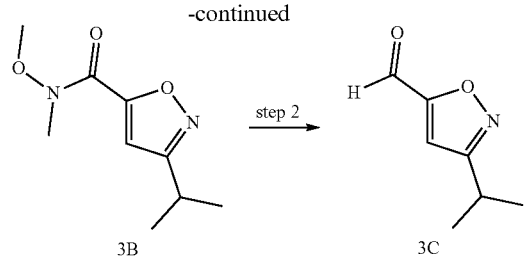

Step 1

To a solution of N,O-dimethylhydroxyl amine hydrochloride (0.93 g, 9.67 mmol) in MeCN (50 mL) was added DIPEA (3.77 g, 29 mmol) dropwise, followed by compound 3A (1.5 g, 9.67 mol), then HATU (3.67 g, 9.67 mmol). The reaction was allowed to stir at room temperature for 30 minutes, then water was added, and the resulting solution was extracted with ethyl acetate. The organic layer was washed with brine, dried over $Na_2SO_4$, filtered and concentrated in vacuo. The residue obtained was purified using flash column chromatography on silica gel to provide compound 3B. $^1$H-NMR: (CDCl$_3$, 400 MHz) δ: 6.72 (s, 1H), 3.79 (s, 3H), 3.33 (s, 3H), 3.12-3.05 (m, 1H), 1.28 (d, J=8 Hz, 6H). MS (ESI) m/z (M+H)+: 199.

Step 2

A solution of compound 3B (1.7 g, 8.63 mmol) in dry THF was degassed and placed under $N_2$ atmosphere, then was cooled to −75° C. DIBAL (1M in toluene, 9.5 mmol) was then added, and the reaction was allowed to stir for for 40 minutes. Water was added to quench the reaction, and the resulting solution was extracted with ethyl acetate. The organic layer was washed with brine, dried over $Na_2SO_4$, filtered and concentrated in vacuo to provide intermediate compound 3C. MS (ESI) m/z (M+H)+: 140.

Example 4

Synthesis of Intermediate Compound 4D

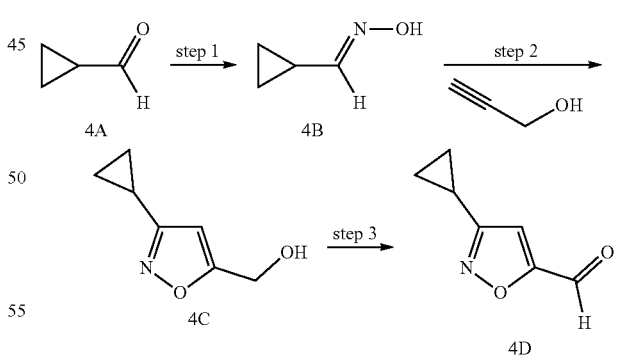

Step 1

To a suspention of hydrazine hydrochloride (26.2 g, 0.38 mol) in THF (350 mL) was added 1NNaOH (350 mL) at room temperature slowly. The mixture was adjusted to pH=6 then compound 4A (24.5 g, 0.35 mol) was added. The reaction was to stir for 4 hours, then the reaction mixture was diluteded with ethyl acetate. The organic phase was washed with brine, dried over $Na_2SO_4$, filtered and concentrated in vacuo to provide compound 4B as a solid. $^1$H-NMR (DMSO, 400 MHz): δ10.51 (s, 1H), 5.95 (d, J=8.6 Hz, 1H), 2.01-2.13 (m, 1H), 0.73-0.81 (m, 2H), 0.46-0.55 (m, 2H).

Step 2

To a solution of compound 4B (4.2 g, 50 mmol) in dry DCM (200 mL) at 40° C. was added NCS (8.0 g, 60 mmol) in portions and the resulting reaction was allowed to stir at this temperature for 30 minutes. Prop-2-yn-1-ol (3.4 g, 60 mmol) was added, followed by dropwise addition of triethylamine and the reaction was allowed to stir at 40° C. for an additional 2 hours. The reaction mixture was washed with brine, dried over $Na_2SO_4$, filtered and concentrated in vacuo to provide a residue that was purified using chromatography on silica gel to provide compound 4C as a liquid. $^1$H-NMR (DMSO, 400 MHz): δ6.07 (s, 1H), 5.54 (t, J=6.1 Hz, 1H), 4.45 (d, J=6.3 Hz, 2H), 1.89-1.99 (m, 1H), 0.91-1.02 (m, 2H), 0.65-0.77 (m, 2H).

Step 3

To a 0° C. suspension of compound 4C (2.0 g, 14 mmol) in DCM (60 mL) was added Dess-Martin periodinane (6.5 g, 15 mmol) in portions and then allowed to stir at 30° C. for 2 hours. The organic phase was washed with saturated $Na_2SO_3$, saturated $NaHCO_3$, brine, dried over $Na_2SO_4$, and concentrated in vacuo to provide intermediate compound 4D as a liquid. $^1$H-NMR (DMSO, 400 MHz): δ 9.82 (s, 1H), 7.16 (s, 1H), 2.03-2.14 (m, 1H), 1.03-1.08 (m, 2H), 0.80-0.85 (m, 2H).

Example 5

Synthesis of Intermediate Compound 5D

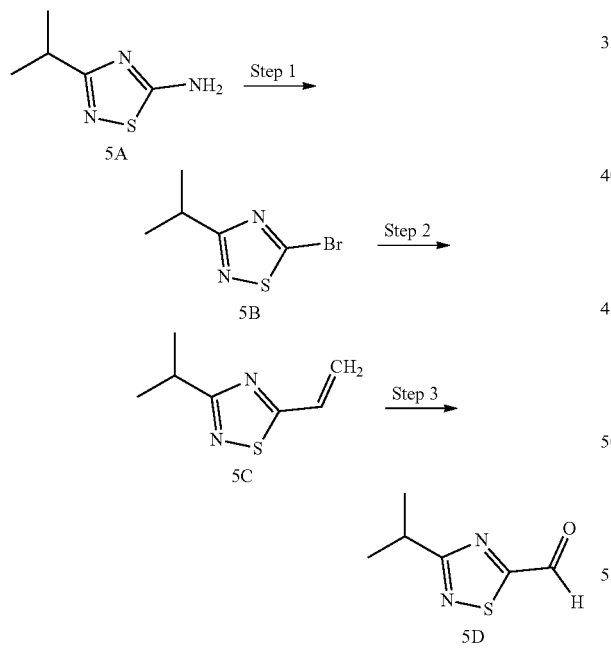

Step 1 t-BuONO (7 g, 78.7 mmol) was added dropwise to an degassed solution of $CuBr_2$ (7.4 g, 78.7 mmol) in acetone (120 mL) at 0° C. under nitrogen. The reaction was allowed to stir at room temperature for 2 hours, then a solution of compound 5A in acetone (30 mL) was added slowly, and the reaction was allowed to stir at room temperature for 1.5 hours. The reaction mixture was cooled to 0° C. and charged with 48% HBr (8.1 mL) dropwise. The mixture was allowed to stir at 0° C. for 30 minutes, and then allowed to stir at room temperature for 10 minutes. The reaction mixture was extracted with DCM, dried over anhydrous sodium sulfate, filtered and concentrated in vacuo. The residue obtained was purified using flash column chromatography on silica gel (petroleum ether/ethyl acetate(100/1)) to provide compound 5B as an oil.

Step 2

To a solution of compound 5B (2.07 g, 10 mmol) in toluene (20 mL) was added tributyl(vinyl)tin (4.75 g, 15 mmol) and $Pd(PPh_3)_4$ (592 mg, 0.5 mmol). The reaction was allowed to stir at reflux for 1 hour, then cooled to room temperature, and filtered through a pad of celite. The filtrate was concentrated in vacuo, and the residue obtained was purified using flash column chromatography on silica gel (petroleum ether/ethyl acetate(100/1-10/1)) to provide compound 5C as an oil (1.2 g).

Step 3

A solution of compound 5C (1.2 g, 9 mmol) in DCM (20 mL) and methanol (4 ml) was ozonized, then the reaction was quenched with an excess of dimethylsulfide and allowed to warm to room temperature. After stirring for 2 hours, the reaction mixture was washed with water, dried over anhydrous sodium sulfate, filtered, and concentrated in vacuo. The residue obtained was purified using flash column chromatography on silica gel to provide intermediate compound 5D as a oil (850 mg).

Example 6

Synthesis of Intermediate Compound 6D

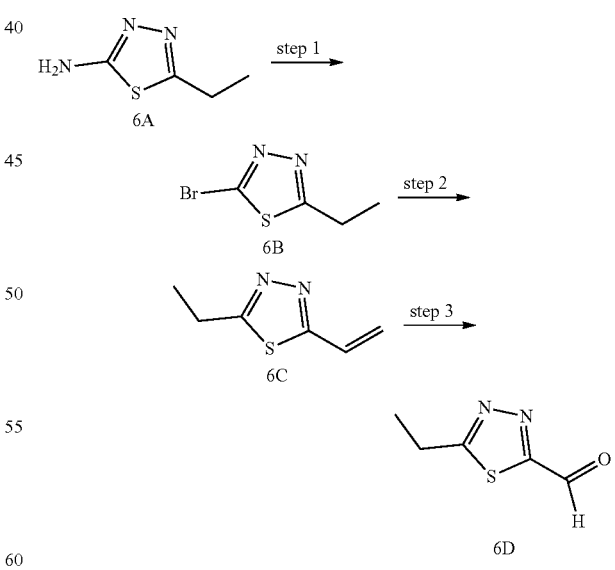

Intermediate compound 6D was made from compound 6A using the methods described in Example 5. MS (ESI) m/z (M+H)$^+$: 143.

Example 7

Synthesis of Intermediate Compound 7E

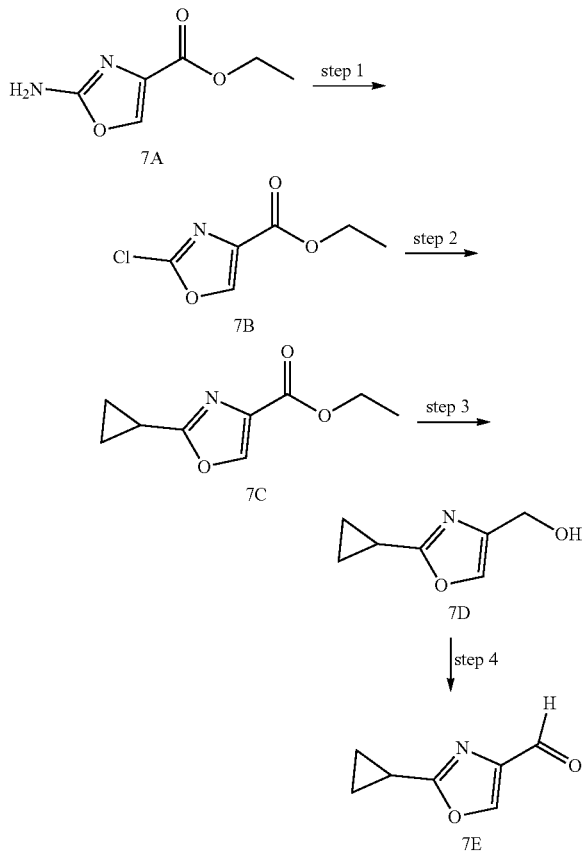

Step 1

Compound 7A was added in portions to a stirred solution of tert-butyl nitrite (6.92 g, 67.12 mmol) and copper (II) chloride (9.02 g, 67.12 mmol) in MeCN(200 mL) at 60° C. The mixture was heated at 80° C. and allowed to stir at this temperature for 2 hours, then the reaction mixture was cooled and patitioned between dichloromethane (250 mL), water (130 mL), and concentrated hydrochloric acid (13 mL). The aqueous layer was further extracted with dichlormethane, and the combined organics were washed with brine, dried over $Na_2SO_4$, filtered, and concentrated in vacuo. The residue obtained was purified using flash column chromatography on silica gel (petroleum ether/ethyl acetate 100:150:1) to provide compound 7B as a solid. MS (ESI) m/z $(M+H)^+$: 176.

Step 2

To a solution of compound 7B (3.5 g, 19.89 mmol) in toluene/$H_2O$ (10:1, 165 mL) was added cyclopropylboronic acid (5.13 g, 59.66 mmol), Pd(OAc)$_2$ (0.45 g, 1.99 mmol), n-BuPACl$_2$ (1.42 g, 3.98 mmol) and Cs$_2$CO$_3$ (19.45 g, 59.66 mmol). The reaction was heated to 100° C. and allowed to stir under $N_2$ at this temperature overnight. The reaction mixture was filtered, the filtrate was washed with water (50 mL) and extracted with ethyl acetate (200 mL). The organics were washed with brine, dried over anhydrous sodium sulfate, filtered, and concentrated in vacuo, and the residue obtained was purified using flash column chromatography on silica gel (petroleum ether/ethyl acetate=100:1→50:1→20:1) to provide compound 7C. MS (ESI) m/z $(M+H)^+$: 182.1.

Step 3

LiAlH$_4$ (1.13 g, 29.6 mmol) was added in portions to a stirred solution of compound 7C (2.68 g, 14.81 mmol) in DCM (50 mL). The reaction mixture was allowed to stir under $N_2$ at room temperature for 5 hours. The reaction was then cooled to 0° C., and the following were added dropwise and sequentially: water (1.5 mL), NaOH (15%, 1.5 mL) and water (3.5 mL). The reaction was allowed to stir for 15 minutes, then solid Na$_2$SO$_4$ was added, and the reaction was allowed to stir for and additional 15 minutes, then filtered. The filtrate was concentrated in vacuo to provide compound 7D. MS (ESI) m/z $(M+H)^+$: 140.2.

Step 4

Dess-Martin periodinane (7.3 g, 16.9 mmol) was added in portions to a solution of compound 7D (1.57 g, 11.28 mmol) in DCM (120 mL) at 0° C. The resulting reaction was allowed to stir at room temperature under $N_2$ overnight. Na$_2$S$_2$O$_3$/NaHCO$_3$ (1:1, 80 mL) was then added, and the reaction mixture as allowed to stir at 0° C. for 15 minutes, and extracted with DCM (150 mL). The organic extract was dried over Na$_2$SO$_4$, filtered, and concentrated in vacuo, and the residue obtained was purified using flash column chromatography on silica gel using a petroleum ether/ethyl acetate gradient as eluent (50:1→20:1→10:1) to provide intermediate compound 7E. MS (ESI) m/z $(M+H)^+$: 138.2.

Example 8

Synthesis of Intermediate Compound 8B

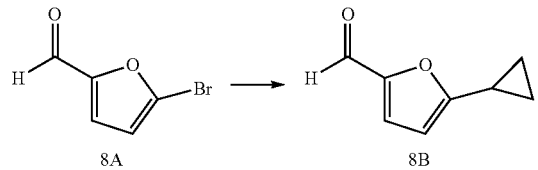 [SMILES: O=Cc1ccc(Br)o1 ; O=Cc1ccc(C2CC2)o1]

A suspension of compound 8A (1.5 g, 8.6 mmol), cyclopropylboronic acid (2.22 g, 25.8 mmol), Pd(OAc)$_2$ (116 mg, 0.516 mmol), n-BuPACl$_2$ (308 mg, 0.86 mmol), Cs$_2$CO$_3$ (8.4 g, 25.8 mmol) in toluene/$H_2O$ (10:1, 33 mL) was heated to 100° C. and allowed to stir at this temperature overnight under $N_2$ atmosphere. The reaction mixture was transferred to a separatory funnel, and the collected organic phase was concentrated in vacuo. The residue obtained was purified using flash column chromatography on silica gel (petroleum ether/ethyl acetate=50:1→20:1) to provide intermediate compound 8B.

Example 9

Synthesis of Intermediate Compound 9F

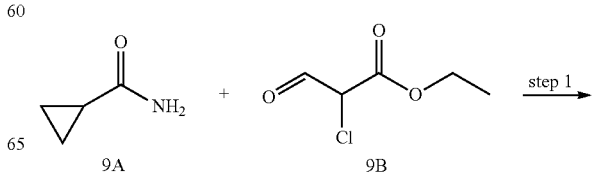

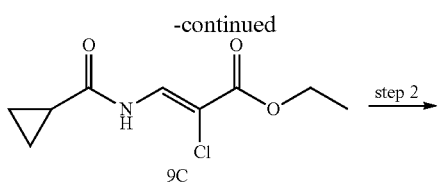

anhydrous sodium sulfate, filtered, and concentrated in vacuo. The residue obtained was purified using flash column chromatography on silica gel (petroleum ether/ethyl acetate=30:1 to 10:1) to provide compound 9C. $^1$H-NMR (CDCl$_3$, 400 MHz): δ ppm 8.19-8.39 (m, 1H), 7.59-7.86 (m, 1H), 4.26 (d, J=7.04 Hz, 2H), 1.53-1.62 (m, 1H), 1.30 (t, J=7.04 Hz, 3H), 1.08-1.18 (m, 2H), 0.88-1.03 (m, 2H). MS (ESI) m/z (M+H)$^+$: 218.

Step 2

A mixture of compound 9C (434 mg, 2 mmol) and t-BuOK (610 mg, 6 mmol) in DMF (20 mL) was allowed to stir at 100° C. for 5 hours. The mixture was then poured into H$_2$O, extracted with ethyl acetate (150 mL) and the extract was washed with brine, dried over anhydrous sodium sulfate, filtered, and concentrated in vacuo. The residue obtained was purified using flash column chromatography on silica gel (petroleum ether/ethyl acetate=30:1 to 10:1) to provide compound 9D. $^1$H-NMR (CDCl$_3$, 400 MHz): δ ppm 7.53 (s, 1H), 4.29 (d, J=7.43 Hz, 2), 2.01-2.15 (m, 1H), 1.30 (s, 3H), 1.01-1.15 (m, 4H). MS (ESI) m/z (M+H)$^+$: 182.

Step 3

To a 0° C. solution of compound 9D (220 mg, 1.2 mmol) in THF (10 mL) was added LiAlH$_4$ (82 mg, 2.4 mmol) in portions and the reaction was allowed to stir at 30° C. for 30 minutes. Na$_2$SO$_4$ was then added, and the resulting reaction was quenched with H$_2$O. The reaction mixture was filtered and the filtrate was dried over anhydrous Na$_2$SO$_4$, filtered, and concentrated in vacuo, to provide compound 9E.

Step 4

To a 0° C. solution of compound 9E (160 mg, 1.2 mmol) in DCM (20 mL) was added Dess-Martin reagent (526 mg, 1.4 mmol) in portions with stirring. The reaction was allowed to stir at 30° C. for 2 hours, then the reaction was quenched with saturated aqueous Na$_2$SO$_3$. The resulting solution was filtered, and the filtrate was washed sequentially with saturated aqueous Na$_2$S$_2$O$_3$, saturated aqueous Na$_2$CO$_3$ and brine, then dried over Na$_2$SO$_4$, filtered and concentrated in vacuo to provide intermediate compound 9F.

Step 1

A suspension of compound 9B (22.8 g, 120 mmol) in DMF (100 mL) was adjusted to pH 2 via dropwise addition of concentrated sulfuric acid. Compound 9A (8.5 g, 100 mmol) was added at 30° C. and was allowed to stir at 100° C. for 10 h. The mixture was poured into H$_2$O, extracted with ethyl acetate (150 mL), washed with brine, dried over Example 10

Preparation of Compounds 1 and 2

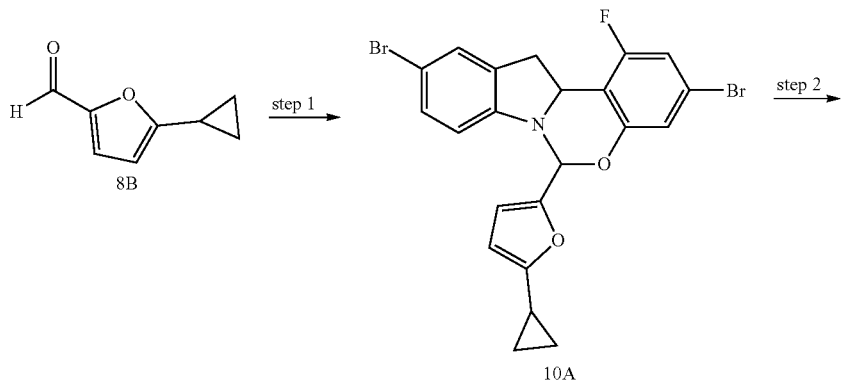

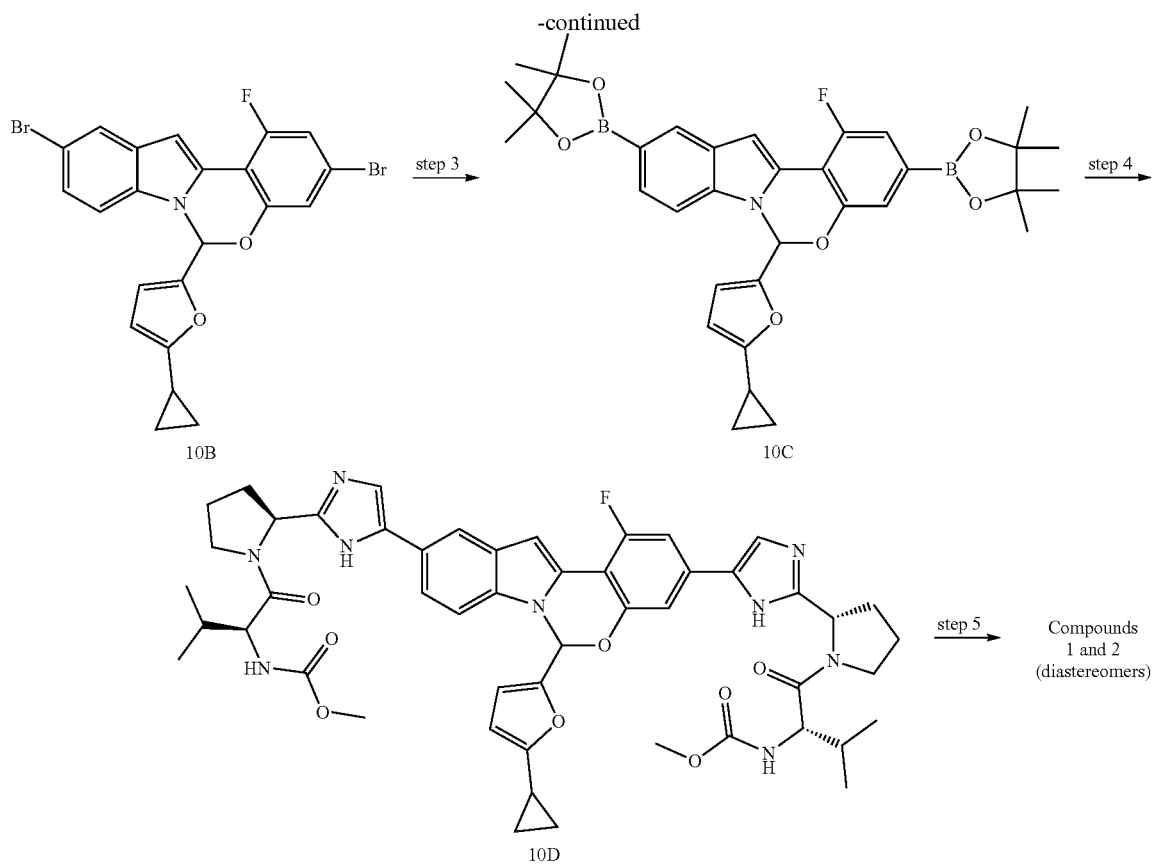

Step 1

To a solution of intermediate compound 8B (386 mg, 284 mmol) and 5-bromo-2-(5-bromoindolin-2-yl)-3-fluorophenol (1.0 g, 258 mmol) in THF (10 mL) was added methanesulfonic acid (5 mg, 0.052 mmol). The resulting mixture was allowed to stir for 2 h. THF was removed in vacuo to provide the residue. It was recrystallized by acetonitrile to provide compound 10A. MS (ESI) m/z (M+H)$^+$: 505.

Step 2

To a solution of compound 10A (900 mg, 1.8 mmol) in dry toluene (18 mL) was added DDQ (610 mg, 2.7 mmol). The reaction was heated to reflux and allowed to stir at this temperature for 3 hours, then the reaction mixture was concentrated in vacuo, and the resulting residue was diluted with EtOAc. The resulting solution was washed with saturated aqueous $NaS_2O_3$ and brine, dried over $Na_2SO_4$, filtered and concentrated in vacuo. The residue obtained was washed with MeOH (10 mL), filtered, and the collected solid was dried under vacuum to provide compound 10B. MS (ESI) m/z (M+H)$^+$: 503.

Step 3

To a solution of compound 10B (730 mg, 1.46 mmol) in 1,4-dioxane (20 mL) was added bis pinacol borate (810 mg, 3.25 mmol), Pd(dppf)$_2$Cl$_2$ (107 mg, 0.146 mmol) and KOAc (858 mg, 8.75 mmol). The reaction mixture was heated to 110° C. and allowed to stir under N$_2$ atmosphere at this temperature overnight. The reaction mixture was then cooled to room temperature, and concentrated in vacuo. The residue obtained was purified using flash column chromatography on silica gel (petroleum ether/ethyl acetate=20:1→8:1) to provide compound 10C. MS (ESI) m/z (M+H)$^+$: 598.

Step 4

A suspension of compound 10C (670 mg, 1.12 mmol), compound Br-imidazole-3 (878 mg, 2.35 mmol), Pd(dppf)$_2$Cl$_2$ (82 mg, 0.112 mmol), Na$_2$CO$_3$ (475 mg, 4.48 mmol) and in THF/H$_2$O (5:1, 24 mL) was heated to reflux and allowed to stir at this temperature overnight under N$_2$ atmosphere. The reaction mixture was cooled to room temperature, and filtered, and the filtrate was washed with water (50 mL) and extracted with ethyl acetate (100 mL). The organic extract was washed with brine, dried over anhydrous sodium sulfate, filtered and concentrated in vacuo, and the residue obtained was purified using flash column chromatography on silica gel (petroleum ether/ethyl acetate=1:5→1:8) to provide compound 10D as a mixture of diastereomers.

Step 5

400 mg of compound 10D was separated into its individual diastereomers (designated as compound 1 and compound 2) using SFC to provide compound 1 (Rt=3.52 min) and compound 2 (Rt=6.33 min). Column: Chiralpak AS-H 250×20 mm I.D., 5 μm Mobile phase: 40% of EtOH (0.05% DEA) in CO$_2$ Flow rate: 50 mL/min Wavelength: 340 nm.

1: $^1$H-NMR (MeOD, 400 MHz) δ: 7.98 (s, 1H), 7.89 (s, 1H), 7.73 (s, 1H), 7.48-7.46 (m, 2H), 7.34-7.28 (m, 3H), 7.15-7.14 (s, 1H), 5.87-5.84 (q, 2H), 5.24-5.17 (m, 2H), 4.22-4.19 (t, 2H), 4.08-4.07 (s, 2H), 3.87-3.83 (t, 2H), 3.63 (s, 6H), 2.55-2.51 (m, 2H), 2.26-2.01 (m, 8H), 1.80-1.77 (t, 1H), 0.97-0.87 (m, 12H), 0.79-0.77 (d, 2H), 0.57-0.53 (m, 2H). MS (ESI) m/z (M+H)$^+$: 930.

2: $^1$H-NMR (MeOD, 400 MHz) δ: 7.96 (s, 1H), 7.88 (s, 1H), 7.73 (s, 1H), 7.48-7.46 (m, 2H), 7.34-7.28 (m, 3H), 7.15-7.14 (s, 1H), 5.87-5.84 (q, 2H), 5.24-5.17 (m, 2H), 4.22-4.19 (t, 2H), 4.08-4.07 (s, 2H), 3.87-3.83 (t, 2H), 3.63 (s, 6H), 2.55-2.51 (m, 2H), 2.26-2.01 (m, 8H), 1.80-1.77 (t, 1H), 0.97-0.87 (m, 12H), 0.79-0.77 (d, 2H), 0.56-0.53 (m, 2H). MS (ESI) m/z (M+H)+: 930.

Example 11

Preparation of Compounds 3 and 4

Step 1

To a mixture of intermediate compound 9F (160 mg, 1.2 mmol) and compound core-1 (387 mg, 1 mmol) in anhydrous CH₃CN (8 mL) was added TFA (0.3 mmol). The reaction was agitated for 6 hours at room temperature, then the reaction mixture was filtered. The collected solid was washed with CH₃CN and dried under vacuum to provide compound 11A. MS (ESI) m/z (M+H)+: 507.

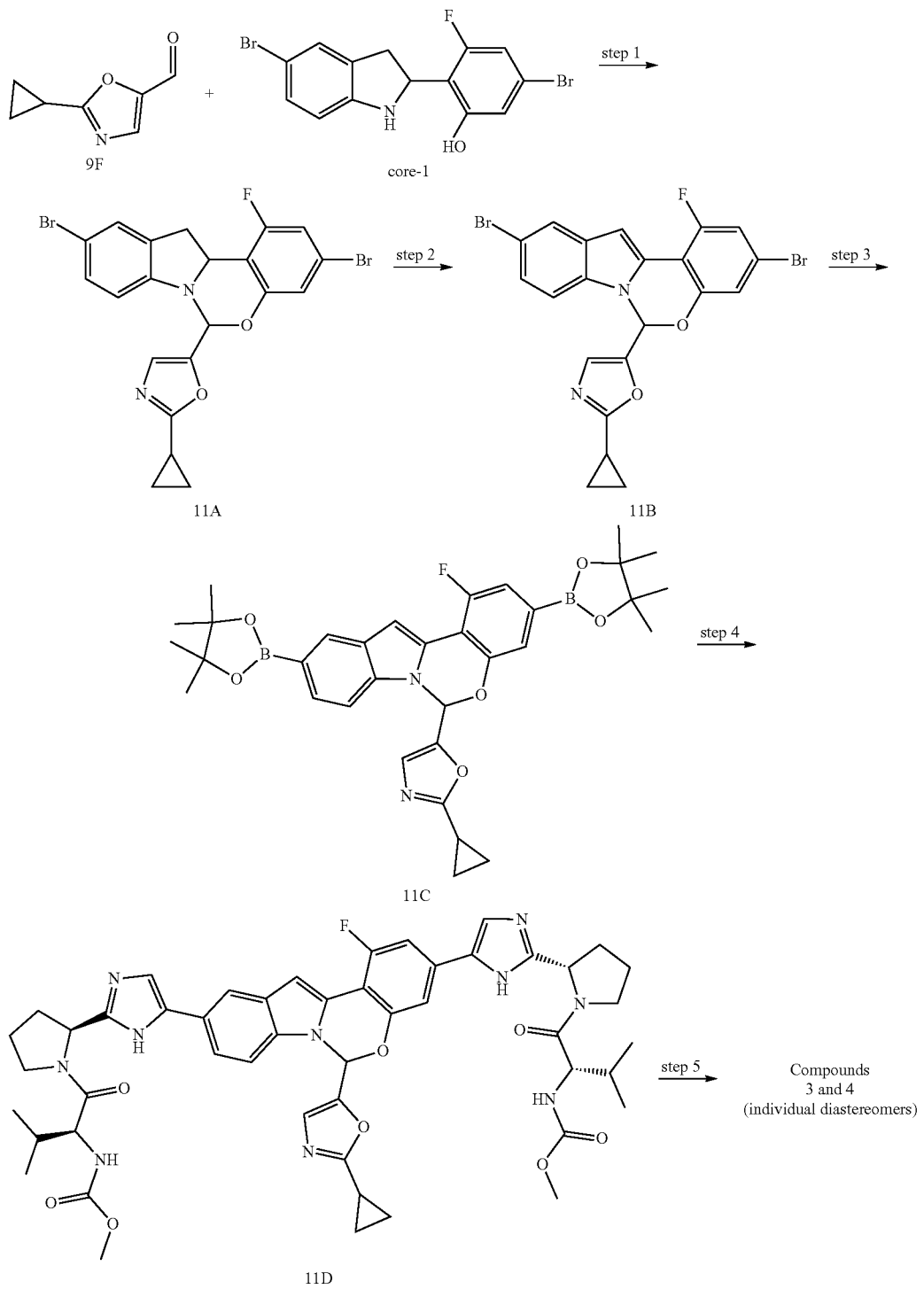

Step 2

To a solution of compound 11A (340 mg, 0.7 mmol) in toluene (20 mL) was added DDQ (227 mg, 1.0 mmol). The reaction was heated to reflux and allowed to stir at this temperature for 2 hours, then the reaction was cooled to room temperature. The reaction mixture was concentrated in vacuo, and the residue obtained was diluted with EtOAc. The organic layer was washed sequentiall with saturated $NaS_2O_3$ aqueous and brine, dried over $Na_2SO_4$, filtered and concentrated in vacuo. The residue obtained was washed with MeOH (10 mL), filtered and the collected solid was dried under vacuum to provide compound 11B. $^1$H-NMR ($CDCl_3$, 400 MHz): δ 7.86-7.79 (m, 1H), 7.37-7.30 (m, 1H), 7.21 (s, 1H), 7.08 (br, 2H), 7.05-6.97 (m, 2H), 6.31 (s, 1H), 2.06-1.92 (m, 1H), 1.02 (br. s., 4H). MS (ESI) m/z (M+H)$^+$: 505.

Step 3

To a solution of compound 11B (240 mg, 0.5 mmol) in 1,4-dioxane (20 mL) was added bis pinacol borate (280 mg, 1.1 mmol), Pd(dppf)Cl$_2$ (36 mg, 0.05 mmol) and KOAc (245 mg, 2.5 mmol). The reaction mixture was heated to 110° C. and allowed to stir under N$_2$ at this temperature overnight. The reaction was cooled to room temperature, concentrated in vacuo, and the residue obtained was purified using flash column chromatography on silica gel (petroleum ether:ethyl acetate=20:1 to 10:1) to provide compound 11C. MS (ESI) m/z (M+H)$^+$: 599.

Step 4

A suspension of compound 11C (220 mg, 0.37 mmol), compound Br-imidazole-3 (302 mg, 0.8 mmol), Pd(dppf)Cl$_2$ (29 mg, 0.04 mmol) and Na$_2$CO$_3$ (196 mg, 1.8 mmol) in a mixture of THF/H$_2$O (30/6 mL) was heated to 110° C. and allowed to stir at this temperature overnight under N$_2$ atmosphere. The reaction was cooled to room temperature, and filtered, and the filtrate was washed with water (50 mL) and extracted with ethyl acetate (100 mL) The organic extract was washed with brine, dried over anhydrous sodium sulfate, filtered and concentrated in vacuo. The residue obtained was purified using Preparative HPLC to provide compound 11D as a mixture of diastereomers. MS (ESI) m/z (M+H$^+$): 931.

Step 5

Compound 11D was separated into its individual diastereomers (designated as compound 3 and compound 4) using SFC. Column: Chiralpak AS-H 250×20 mm I.D., 5 μm, Mobile phase: 40% of iso-propanol (0.05% DEA) in CO$_2$, Flow rate: 50 mL/min. Wavelength: 340 nm.

3: $^1$H-NMR (CD$_3$OD, 400 MHz): δ 8.07 (s, 1H), 8.01 (s, 1H), 7.84 (s, 1H), 7.80 (s, 1H), 7.59 (s, 2H), 7.45 (d, J=10.6 Hz, 1H), 7.41-7.38 (m, 1H), 7.28-7.21 (m, 1H), 6.52 (s, 1H), 5.28-5.20 (m, 2H), 4.22 (s, 2H), 4.14-4.06 (m, 2H), 3.92-3.84 (m, 2H), 3.66 (s, 6H), 2.61-2.54 (m, 2H), 2.30-2.13 (m, 6H), 2.08-1.94 (m, 3H), 1.09-0.97 (m, 4H), 0.93-0.89 (m, 12H). MS (ESI) m/z (M/2+H$^+$): 466.

4: $^1$H-NMR (CD$_3$OD, 400 MHz): δ 8.04 (br. s., 1H), 7.99 (s, 1H), 7.82 (br. s., 1H), 7.78 (s, 1H), 7.58 (br. s., 2H), 7.47-7.43 (m, 1H), 7.37 (br. s., 1H), 7.25-7.20 (m, 1H), 6.51-6.46 (m, 1H), 5.27-5.16 (m, 2H), 4.21 (br. s., 2H), 4.13-4.03 (m, 2H), 3.92-3.83 (m, 2H), 3.64 (s, 6H), 2.58-2.50 (m, 2H), 2.30-2.13 (m, 6H), 2.08-2.01 (m, 2H), 1.98-1.93 (m, 1H), 1.05-0.96 (m, 4H), 0.91-0.81 (m, 12H). MS (ESI) m/z (M/2+H$^+$): 466.

The following compounds were made using the methods described above in Examples 10 and 11, and substituting the appropriate reactants and/or reagents:

| | Structure | isomers | Observed [M + H]$^+$ |
|---|---|---|---|
| 5 | 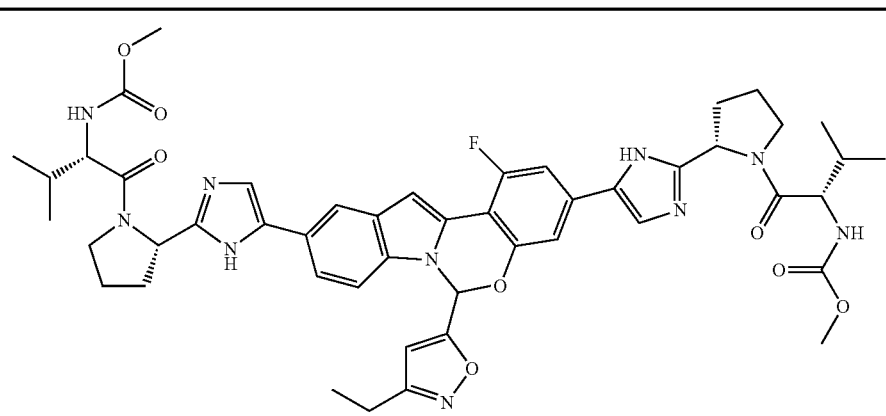 | mixture of diastereomers | 919.66 |

| | Structure | isomers | Observed [M + H]+ |
|---|---|---|---|
| 6 | | mixture of diastereomers | 933.66 |
| 7 8 | | isomer 1 isomer 2 | 919.66 919.66 |
| 9 10 | | isomer 1 isomer 2 | 933.66 933.66 |

| | Structure | isomers | Observed [M + H]+ |
|---|---|---|---|
| 11 | 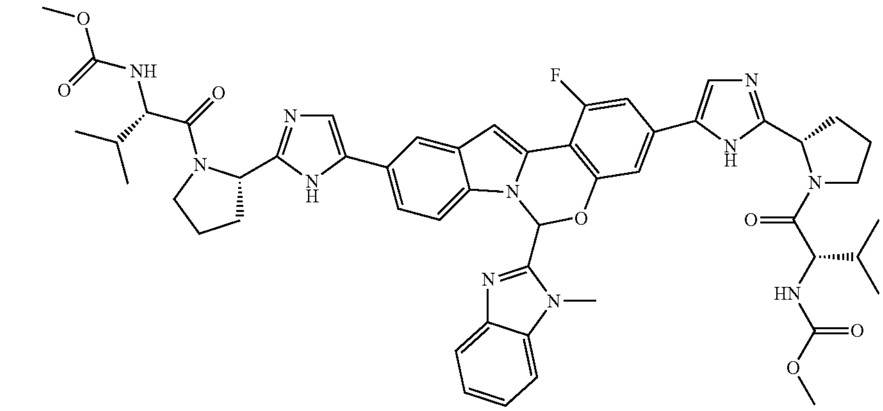 [SMILES: COC(=O)N[C@H](C(=O)N1CCC[C@H]1c1ncc(-c2cc(F)c3c(c2)OC(c2nc4ccccc4n2C)n2c-3cc3cc(-c4cnc([C@@H]5CCCN5C(=O)[C@@H](NC(=O)OC)C(C)C)[nH]4)ccc32)[nH]1)C(C)C] | mixture of diastereomers | 954.66 |
| 12 | 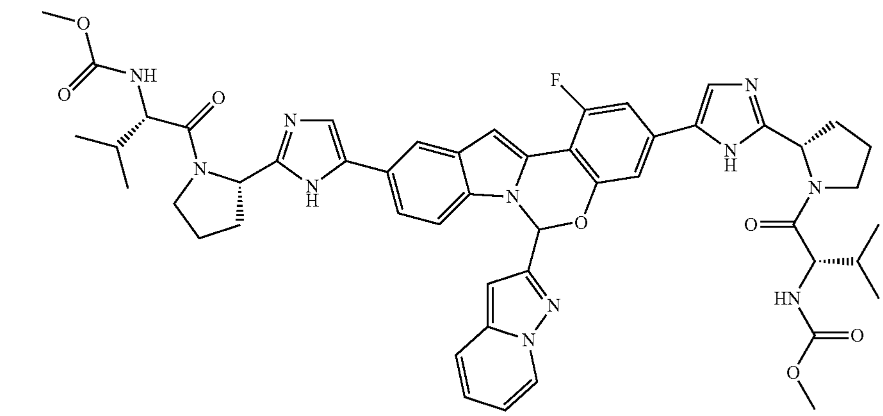 [SMILES: COC(=O)N[C@H](C(=O)N1CCC[C@H]1c1ncc(-c2cc(F)c3c(c2)OC(c2cc4ccccn4n2)n2c-3cc3cc(-c4cnc([C@@H]5CCCN5C(=O)[C@@H](NC(=O)OC)C(C)C)[nH]4)ccc32)[nH]1)C(C)C] | mixture of diastereomers | 940.66 |
| 13 | 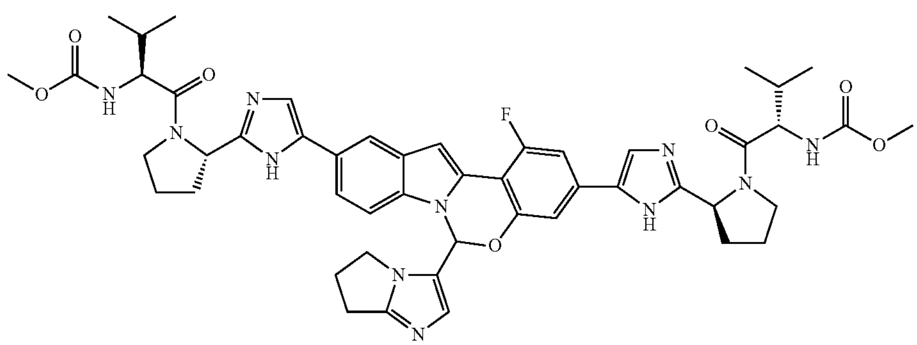 | mixture of diastereomers | 930.66 |
| 14 | 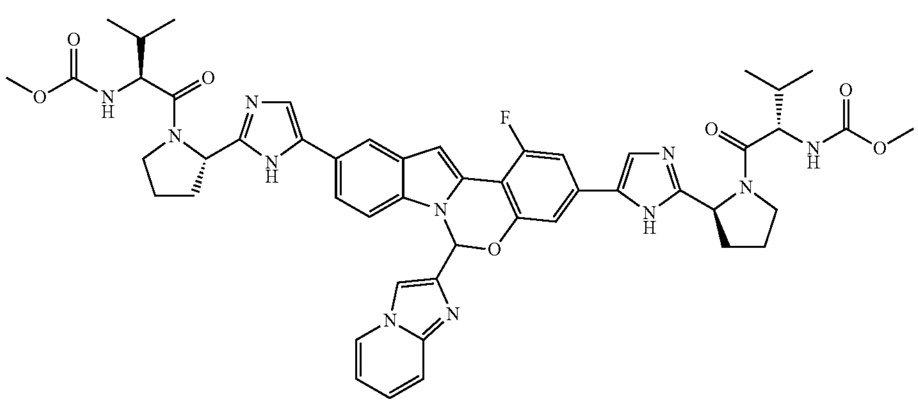 | mixture of diastereomers | 940.66 |

-continued

| Structure | isomers | Observed [M + H]+ |
|---|---|---|
| 15 16 | Isomer 1 Isomer 2 | 922.4 922.4 |
| 17 18 | Isomer 1 Isomer 2 | 891.4 891.4 |

-continued

| | Structure | isomers | Observed [M + H]+ |
|---|---|---|---|
| 19 20 | | Isomer 1 Isomer 2 | 941.4 941.4 |
| 21 22 | | Isomer 1 Isomer 2 | 908.3 908.3 |
| 23 | | Isomer 1 | 905.4 |

-continued

| | Structure | isomers | Observed [M + H]+ |
|---|---|---|---|
| 24 | | Isomer 2 | 905.4 |
| 25 | | Isomer 1 | 933.4 |
| 26 | | Isomer 2 | 933.4 |
| 27 | | Isomer 1 | 919.4 |
| 28 | | Isomer 2 | 919.4 |

-continued

| | Structure | isomers | Observed [M + H]+ |
|---|---|---|---|
| 29 30 | | Isomer 1 Isomer 2 | 931.5 931.5 |
| 31 32 | | Isomer 1 Isomer 2 | 950.4 950.4 |
| 33 34 | | Isomer 1 Isomer 2 | 936.4 936.4 |

-continued
| Structure | isomers | Observed [M + H]+ |
|---|---|---|
| 35 36 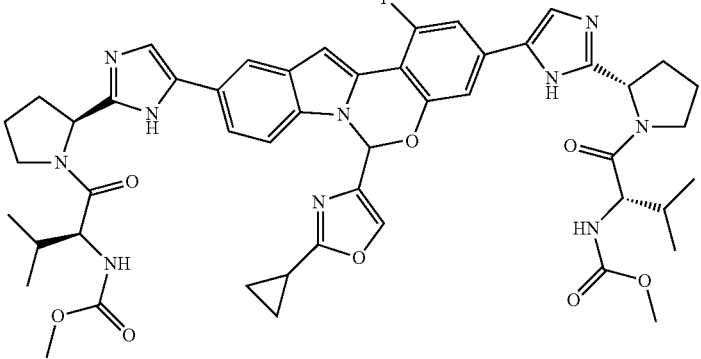 | Isomer 1 Isomer 2 | 931.4 931.4 |
| 37 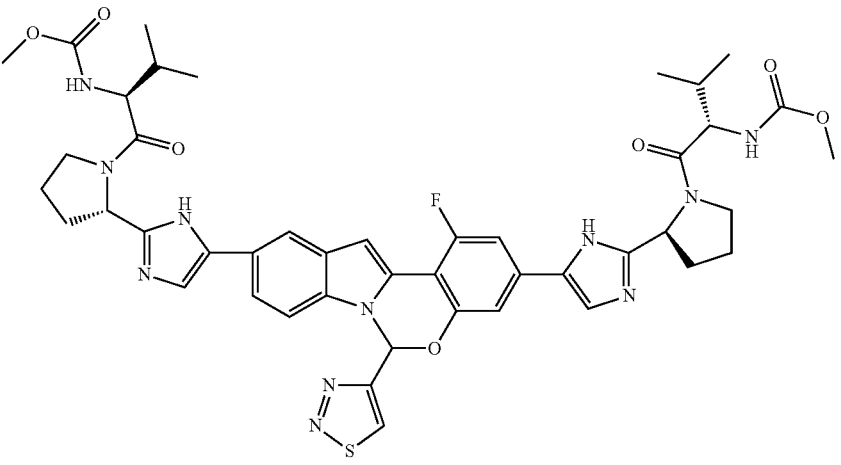 | Mixture of diastereomers | 908.3 |
| 38 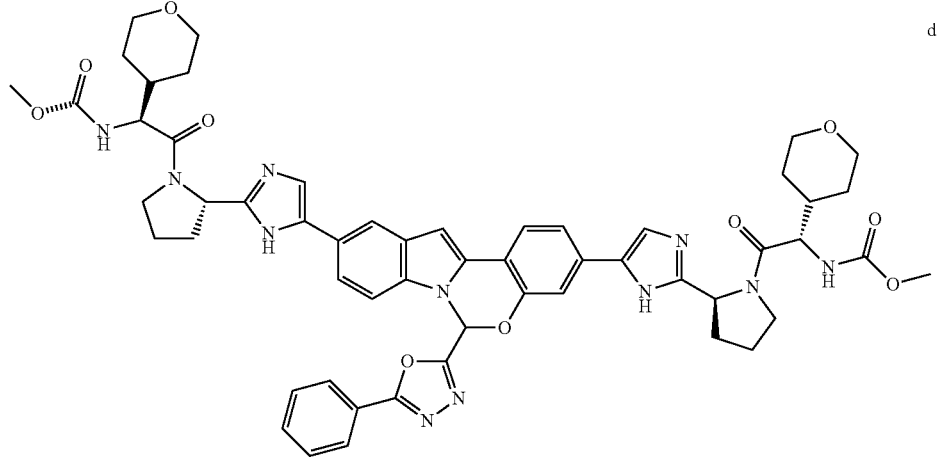 | Mixture of diastereomers | 1034.4 |

-continued
| | Structure | isomers | Observed [M + H]+ |
|---|---|---|---|
| 39 | 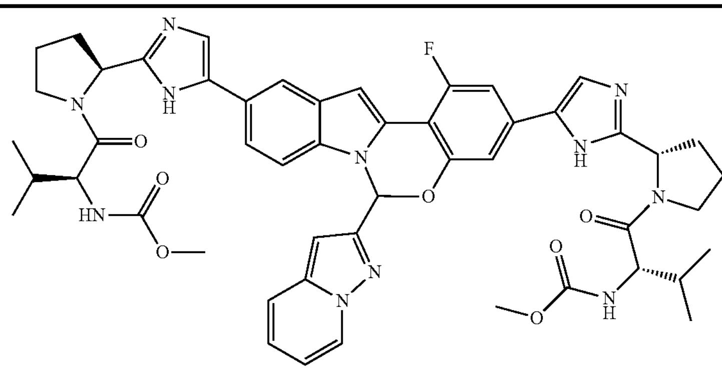 | Mixture of diastereomers | 940.4 |
| 40 | | Isomer 1 | 940.3 |
| 41 | | Isomer 2 | 940.3 |
Example 12
Preparation of Compound 42
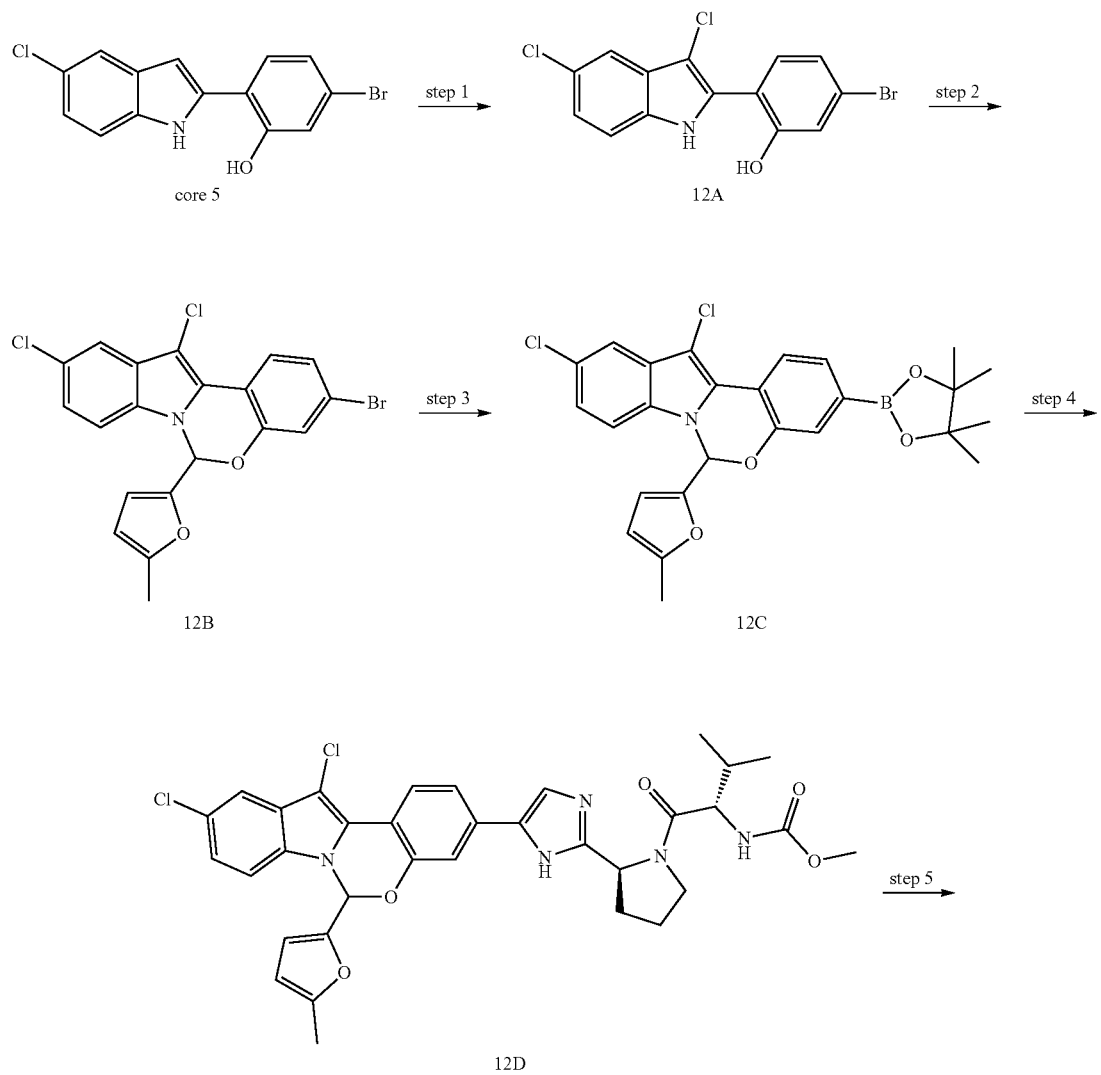

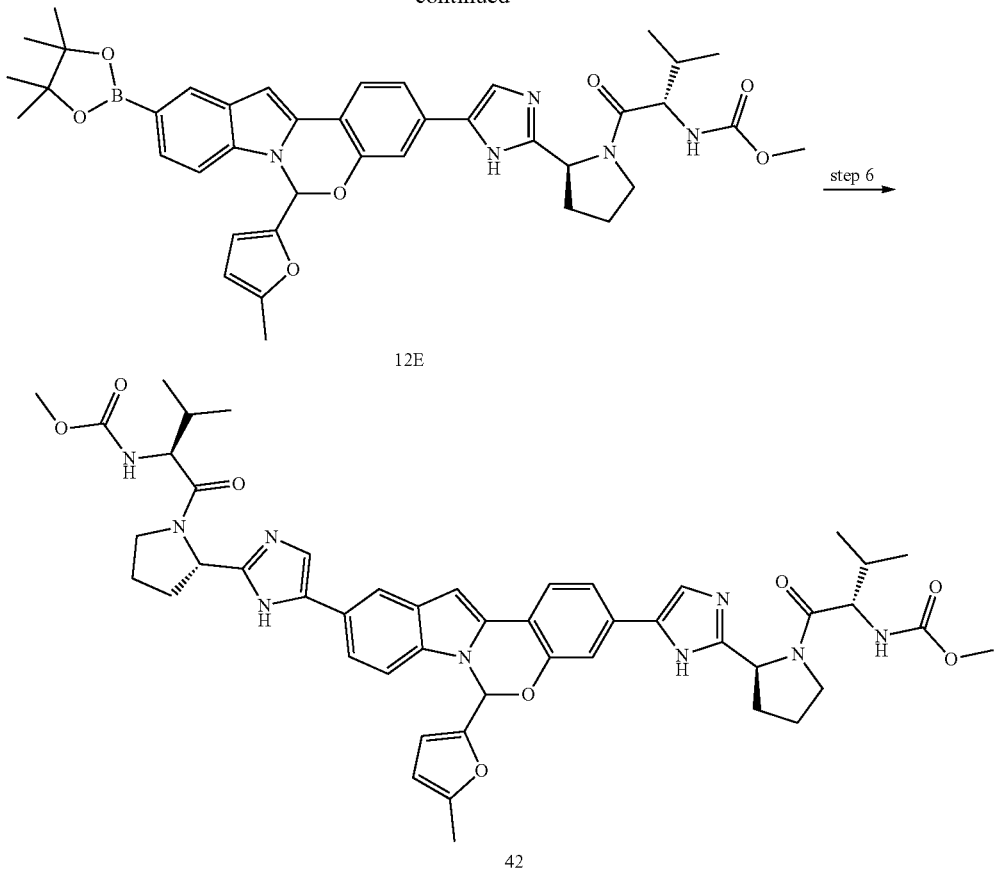

Step 1

A solution of Core-5 (10.0 g, 31.0 mmol) in DCM (200 mL) and anhydrous THF (200 mL) was cooled to 0° C. and N-chlorosuccinimide (4.35 g, 32.6 mmol) was added in portions. The reaction was allowed to stir at 0° C. for 30 minutes, then the reaction was was warmed up to room temperature, and allowed to stir at room temperature for 3 hours. The reaction mixture was concentrated in vacuo, and the residue obtained was dissolved in EtOAc (250 mL), washed with water (2×70 mL), dried over anhydrous MgSO$_4$, filtered, and concentrated in vacuo. The residue obtained was purified using flash column chromatography on silica gel (220 g, 0% to 50% of EtOAc in Hexane) to provide compound 12A. MS (ESI) m/e (M+H$^+$): 357.11.

Step 2

To a 20 mL microwave tube was added compound 12A (1.0 g, 2.80 mmol), 5-methylfuran-2-carbaldehyde (1.542 g, 14.00 mmol), p-Toluenesulfonyl chloride (0.053 g, 0.280 mmol) and toluene (9 mL). The tube was capped and placed in a microwave oven. The solution was allowed to stir at 170° C. for 12 hours. The reaction was then cooled down to room temperature, and concentrated in vacuo. The residue obtained was redissolved in DCM/EtOAc/MeOH, preabsorbed on silica gel (60 ml) and purified using flash column chromatography on silica gel (120 g, 0% to 35% of EtOAc in Hexane) to provide compound 12B. MS (ESI) m/e (M+H$^+$): 451.0.

Step 3

To a 40 mL microwave tube was added compound 12B (0.397 g, 0.883 mmol), 4,4,4',4',5,5,5',5'-octamethyl-2,2'-bi (1,3,2-dioxaborolane) (0.247 g, 0.971 mmol), [1,1'-Bis(diphenylphosphino)ferrocene]dichloropalladium(II) (0.065 g, 0.088 mmol), potassium acetate (0.26 g, 2.65 mmol), and anhydrous dioxane (8.8 mL). The tube was capped and degassed. Anhydrous dioxane (8.8 mL) was added. The solution was allowed to stir at 90° C. in a heating block for 2 hours. The reaction mixture was diluted with EtOAc (20 mL), washed with water (10 mL), dried over anhydrous MgSO$_4$, filtered and concentrated in vacuo. The residue obtained was purified using flash column chromatography on silica gel (24 g, 0% to 50% of EtOAc in Hexane) to provide compound 12C. MS (ESI) m/e (M+H$^+$): 496.1.

Step 4

To a 20 mL microwave tube was added compound 12C (0.496 g, 1.0 mmol), bromo-imidazole-3 (0.411 g, 1.1 mmol), and [1,1'-Bis(diphenylphosphino) ferrocene]dichloropalladium(II) (0.073 g, 0.1 mmol). The tube was capped and degassed. Anhydrous dioxane (10 mL) was added followed by potassium acetate (1M in water, 3.0 mL, 3.0 mmol). The solution was allowed to stir at 80° C. in a heating block for 4 hours. After it was cooled to RT, the aqueous phase was separated and extracted with EtOAc (2×20 mL). Combined organic phase was dried over anhydrous MgSO$_4$, filtered and concentrated in vacuo. The residue obtained was purified using flash column chromatography on silica gel (40 g, 0% to 90% of EtOAc in Hexane) to provide compound 12D (0.450 g). MS (ESI) m/e (M+H$^+$): 662.2.

Step 5

To a 20 mL microwave tube was added compound 12D (0.446 g, 0.673 mmol), 4,4,4',4',5,5,5',5'-octamethyl-2,2'-bi (1,3,2-dioxaborolane) (0.376 g, 1.48 mmol), Tris(dibenzylideneacetone)dipalladium(0)-chloroform adduct (0.07 g, 0.067 mmol), Xphos (0.064 g, 0.135 mmol), potassium acetate (0.198 g, 2.02 mmol), and anhydrous dioxane (6.7 mL). The solution was allowed to stir at 120° C. in a heating block for 1 hour. The reaction mixture was diluted with EtOAc (20 mL), washed with water (10 mL), dried over anhydrous MgSO$_4$, filtered and concentrated in vacuo. The residue obtained was purified using flash column chromatography on silica gel (40 g, 0% to 80% of EtOAc in Hexane) to provide compound 12E. MS (ESI) m/e (M+H$^+$): 720.3.

Step 6

To a 10 mL microwave tube was added compound 12E (0.041 g, 0.057 mmol), bromo-imidazole-3 (0.023 g, 0.062 mmol), and [1,1'-Bis(diphenylphosphino) ferrocene]dichloropalladium(II) (0.004 g, 0.006 mmol). The tube was capped and degassed. Anhydrous dioxane (0.6 mL) was added followed by potassium acetate (1M in water, 0.17 mL, 0.17 mmol). The solution was allowed to stir at 80° C. in a heating block for 4 hours. After it was cooled to RT, the aqueous phase was separated and extracted with EtOAc (2×5 mL). Combined organic phase was dried over anhydrous MgSO$_4$, filtered and concentrated in vacuo. The residue obtained was purified using reversed phase C-18 silica gel chromatography (30 g, 10% to 90% of CH$_3$CN with 0.5% TFA in water with 0.5% TFA) to provide compound 42. MS (ESI) m/e (M+H$^+$): 886.5.

Example 13

Preparation of Compound 43

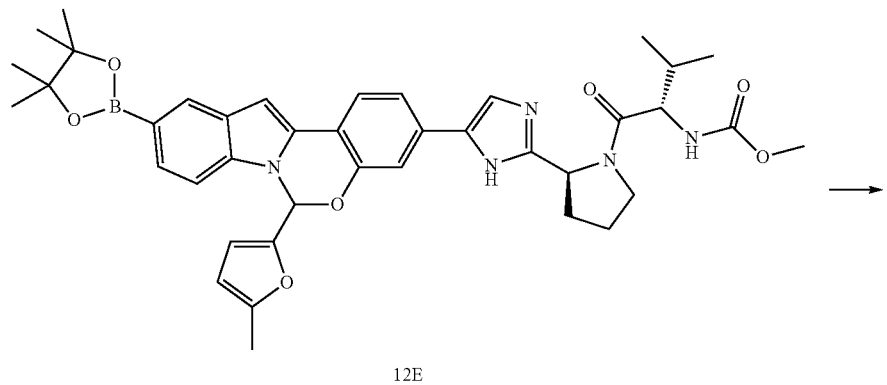

12E

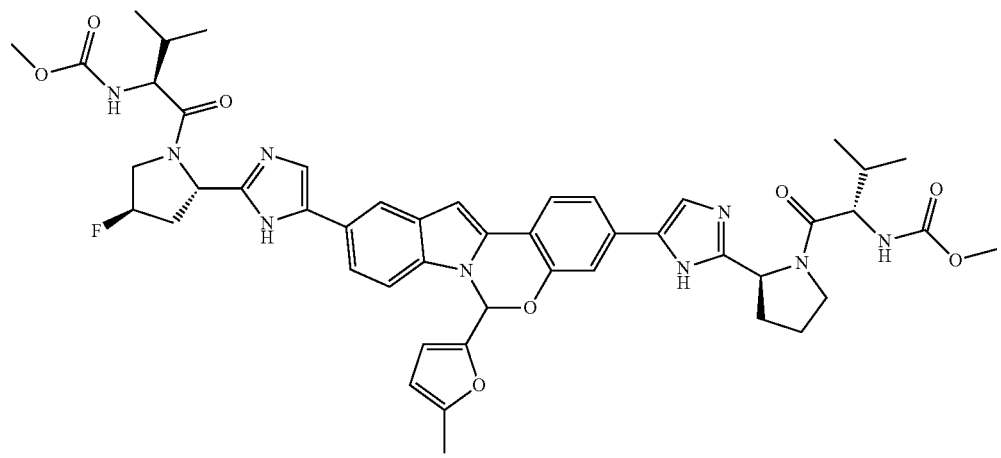

43

To a 10 mL microwave tube was added compound 12E (0.041 g, 0.056 mmol), bromo-imidazole-7 (0.024 g, 0.062 mmol) and [1,1'-bis(diphenylphosphino) ferrocene]dichloropalladium(II) (0.004 g, 0.006 mmol). The tube was capped and degassed. Anhydrous dioxane (1.0 mL) was added followed by potassium acetate (1M in water, 0.17 mL, 0.17 mmol). The reaction was allowed to stir at 80° C. in a heating block for 4 hours, then allowed to cool to room temperature. The aqueous phase was separated and extracted with EtOAc (2×5 mL). The combined organic extracts were dried over anhydrous MgSO$_4$, filtered and concentrated in vacuo. The residue obtained was purified using reverse-phase C-18 silica gel chromatography (30 g, 10% to 90% of CH$_3$CN with 0.5% TFA in water with 0.5% TFA) to provide compound 43. MS (ESI) m/e (M+H$^+$): 904.4.

Example 14

Preparation of Compound 44

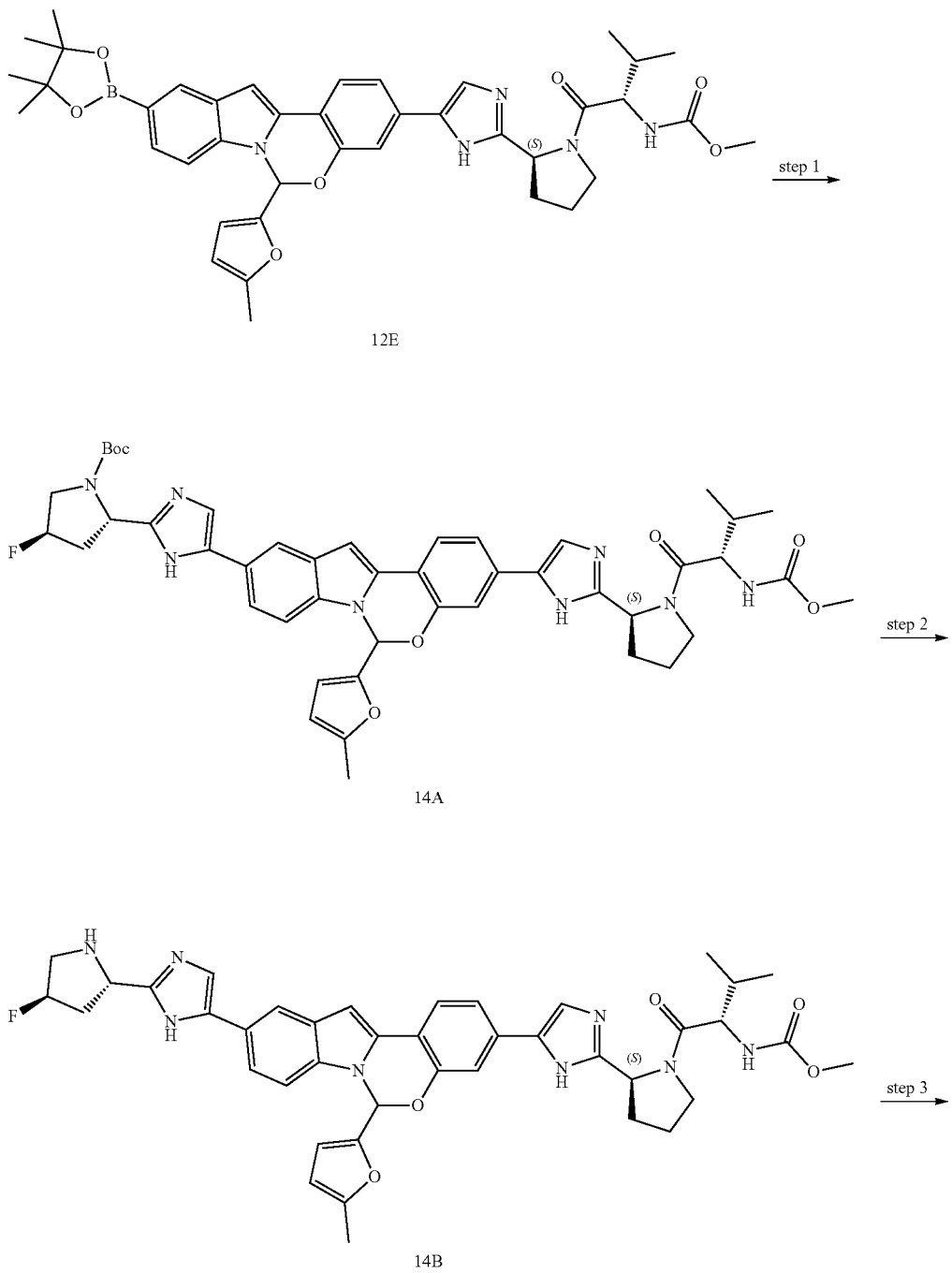

-continued

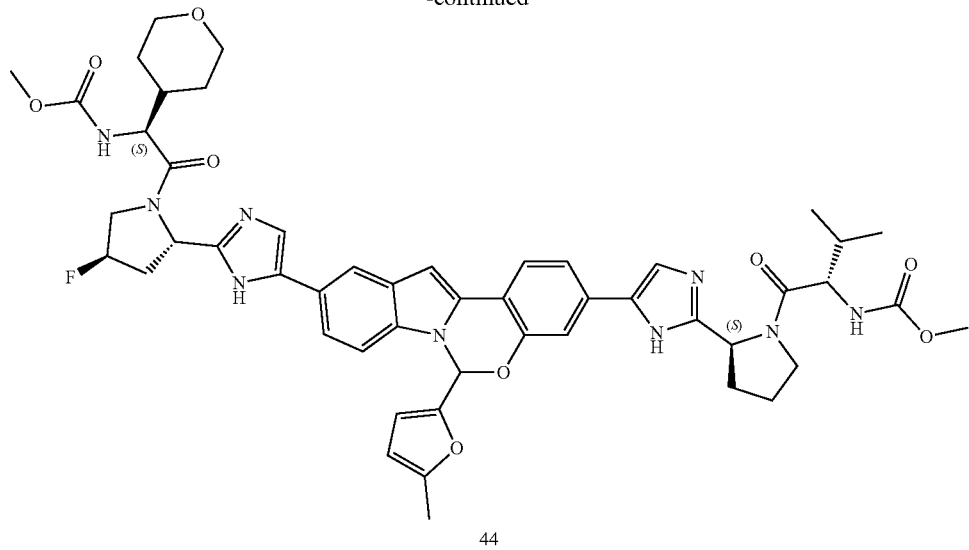

44

Step 1

To a 10 mL microwave tube was added compound 12E (0.050 g, 0.069 mmol), compound Br-imidazole-6 (0.025 g, 0.076 mmol), and [1,1'-Bis(diphenylphosphino)ferrocene] dichloropalladium(II) (0.005 g, 0.007 mmol). The tube was capped and degassed. Anhydrous dioxane (0.7 mL) was added followed by potassium acetate (1M in water, 0.206 mL, 0.206 mmol). The solution was allowed to stir at 80° C. in a heating block for 4 hours. The reaction was cooled to room temperature, and the aqueous phase was separated and extracted with EtOAc (2×5 mL). The combined organic extracts were dried over anhydrous MgSO$_4$, filtered and concentrated in vacuo. The residue obtained was purified using reversed phase C-18 silica gel chromatography (30 g, 10% to 90% of CH$_3$CN with 0.5% TFA in water with 0.5% TFA) to provide compound 14A. MS (ESI) m/e (M+Na$^+$): 869.3.

Step 2

To a 25 mL flask was added compound 14A (0.031 g, 0.036 mmol), anhydrous MeOH (1.0 mL), and HCl (2M in ether, 0.362 mL, 0.725 mmol). The solution was allowed to stir at room temperature overnight. The reaction mixture was concentrated in vacuo to provide compound 14B. MS (ESI) m/e (M+H$^+$): 747.5.

Step 3

To a 25 mL flask was added compound 14B (0.029 g, 0.032 mmol), compound cap-4 (0.008 g, 0.038 mmol), dry DMF (1.0 mL), DIPEA (0.038 mL, 0.224 mmol). The reaction was allowed to stir to 0° C. for 10 minutes and HATU (0.012 g, 0.032 mmol) was added at 0° C. The reaction was then allowed to stir at 0° C. for 30 minutes, then at room temperature for 2 hours. The reaction was quenched with water (0.5 mL), treated with TFA (0.04 mL) for 15 minutes, and EtOAc (20 mL) was added. The collected aqueous phase was separated, basified with saturated NaHCO$_3$ to pH ~9, then extracted with EtOAc (20 mL). The organic extract was washed with water (10 mL), dried over anhydrous MgSO$_4$, filtered and concentrated in vacuo. The residue obtained was purified using reversed phase C-18 silica gel chromatography (30 g, 10% to 90% of CH3CN with 0.5% TFA in water with 0.5% TFA) to provide compound 44. MS (ESI) m/e (M+H$^+$): 946.8.

Example 15

Preparation of Compound 45

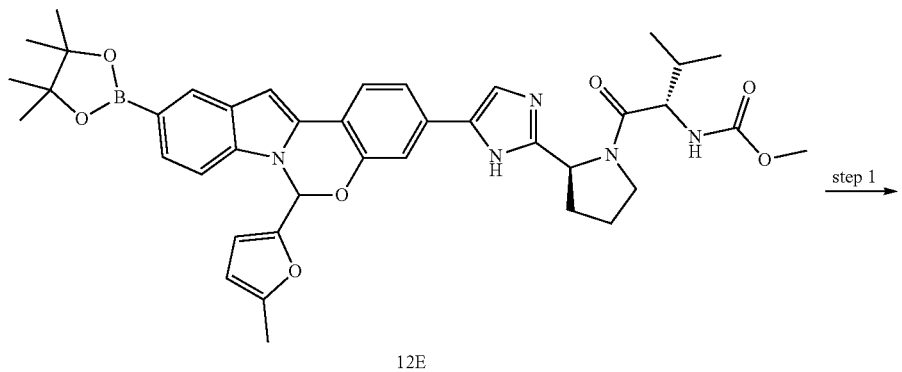

12E step 1

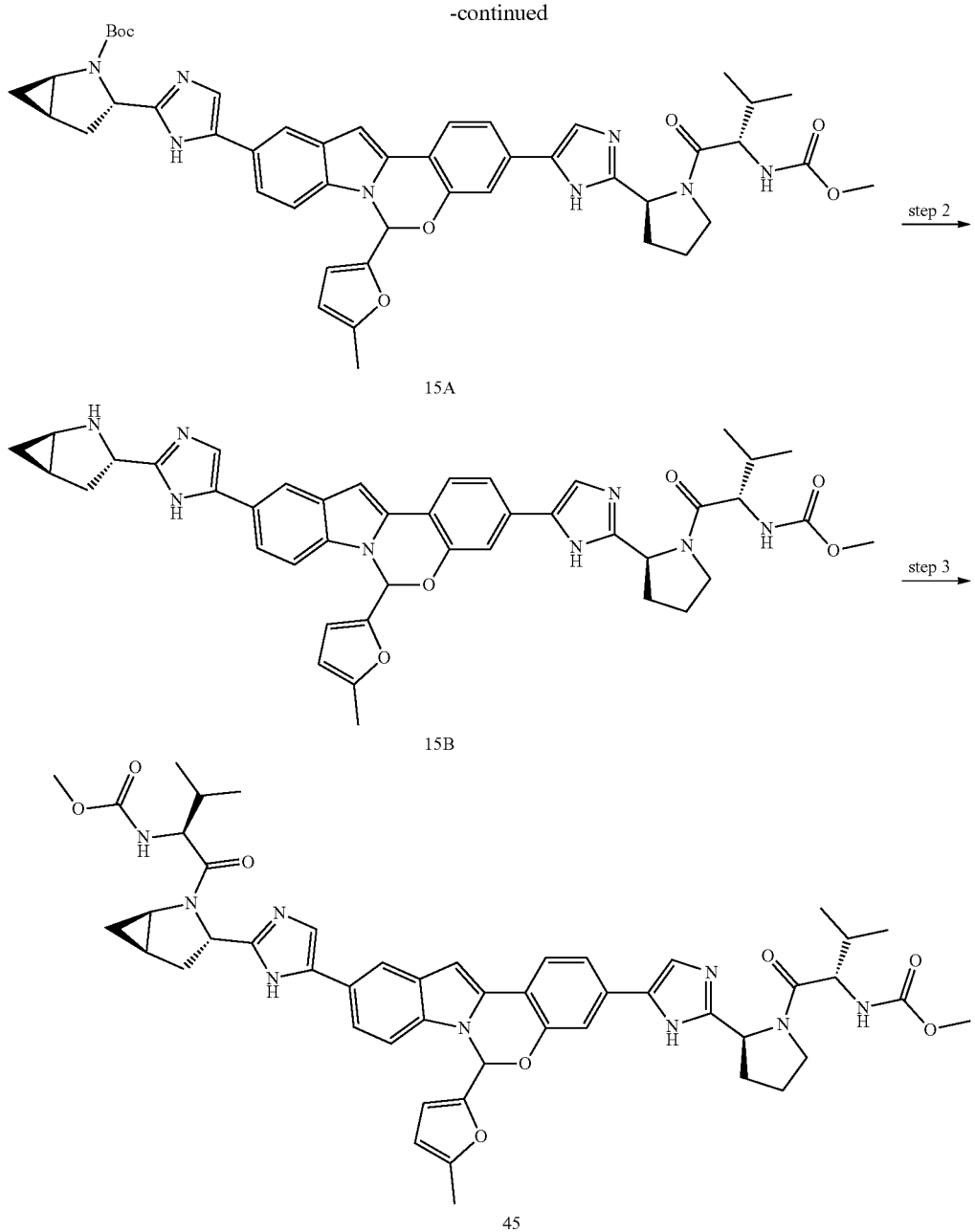

Step 1

To a 10 mL microwave tube was added compound 12E (0.144 g, 0.200 mmol), compound Br-imidazole-2 (0.072 g, 0.220 mmol), and [1,1'-Bis(diphenylphosphino)ferrocene]dichloropalladium(II) (0.015 g, 0.020 mmol). The tube was capped and degassed. Anhydrous dioxane (2.0 mL) was added followed by potassium acetate (1M in water, 0.599 mL, 0.599 mmol). The solution was allowed to stir at 80° C. in a heating block for 4 hours. The reaction was cooled to room temperature, and the collected aqueous phase was separated and extracted with EtOAc (2×5 mL). The combined organic extracts were dried over anhydrous MgSO$_4$, filtered and concentrated in vacuo. The residue obtained was purified using reversed phase C-18 silica gel chromatography (50 g, 10% to 90% of CH3CN with 0.5% TFA in water with 0.5% TFA) to provide compound 15A (0.036 g, 21%). MS (ESI) m/e (M+H$^+$): 841.4.

Step 2

To a 25 mL flask was added compound 15A (0.034 g, 0.04 mmol), anhydrous MeOH (1.0 mL), and HCl (2M in ether, 0.403 mL, 0.403 mmol). The reaction was allowed to stir at room temperature overnight, then the reaction mixture was concentrated in vacuo to provide compound 15B. MS (ESI) m/e (M+H$^+$): 741.5.

Step 3

To a 25 mL flask was added compound 15B (0.031 g, 0.042 mmol), compound cap-1 (0.009 g, 0.05 mmol), and dry DMF (1.0 mL), and DIPEA (0.050 mL, 0.297 mmol). The reaction was allowed to stir to 0° C. for 10 minutes and HATU (0.016 g, 0.042 mmol) was added at 0° C. The reaction was allowed to stir at 0° C. for 30 minutes, then at room temperature for 2 hours. The reaction was quenched with water (0.5 mL) and TFA (0.05 mL) was added, and the resulting solution was allowed to stir for 15 minutes. EtOAc (20 mL) was added, and the aqueous layer was separated, basified with saturated $NaHCO_3$ to pH-9, and then extracted with EtOAc (20 mL). The combined organic phases were washed with water (10 mL), dried over anhydrous $MgSO_4$, filtered and concentrated in vacuo, and the residue obtained was purified using reversed phase C-18 silica gel chromatography (30 g, 10% to 90% of $CH_3CN$ with 0.5% TFA in water with 0.5% TFA) to provide compound 45. MS (ESI) m/e $(M+H^+)$: 898.2.

Example 16

Cell-Based HCV Replicon Assays

To measure cell-based anti-HCV activity of compounds of the present invention, two complimentary assays were employed using various replicons. In the first assay ("Replicon Assay A"), replicon cells were seeded at 2000 cells/well in 384-well 384-well flat bottom tissue culture treated clear bottom plate (Corning 3707) in the presence of the test compound. Various concentrations of test compound, typically in 10 serial dilutions, were added to the assay mixture, with the starting concentration ranging from 333.3 nM to 1.667 nM. The final concentration of DMSO was 0.5%. Fetal bovine serum was 5%, in the assay media. Cells were harvested on day 3 by removing media and washing the cells with a suitable wash buffer. The cells are lysed with the addition of 1× Qiagen lysis buffer (Cat #1062731). The replicon RNA level was measured using real time PCR (TaqMan® EZ RT-PCR, Applied Biosystems 403028) with the following primers and probes:

```
Neo Forward:
CCG GCT ACC TGC CCA TTC

Neo Reverse:
CCA GAT CAT CCT GAT CGA CAA G

Neo Probe:
FAM-ACA TCG CAT CGA GCG AGC ACG TAC-Tamra

Cyc probe:
5'-JOE-CGCGTCTCCTTTGAGCTGTTTGCA-Tamra-3'

Cyc Forward Primer:
ACGGCGAGCCCTTGG

Cyc Reverse Primer:
TTTCTGCTGTCTTTGGGACCT
```

Cyclophilin RNA was used as endogenous control and was amplified in the same reaction as NS5B (multiplex PCR). The real-time RT-PCR reactions were run on ABI PRISM 7900HT Sequence Detection System using the following program: 50° C. for 2 minutes, 60° C. for 30 minutes, 95° C. for 5 minutes, 40 cycles of 94° C. for 20 sec, 55° C. for 1 minutes.

The amount of HCV replicon RNA per cell is quantified using a linear regression curve for a known nanogram (ng) amount of HCV replicon total RNA. This is established by plotting the Cycle Threshold values (Ct) from the Neo probe and primer set versus the log (ng) for each HCV replicon total RNA standard. The amount of HCV RNA for each replicon sample is calculated by taking the sample's Ct value, minus the line intercept, divided by the slope of the line. Similarly, the amount of Cyclophilin mRNA per cell is also quantified using a linear regression curve for a known nanogram (ng) amount of HCV replicon total RNA. Again, this is established by plotting the Cycle Threshold values (Ct) from the Cyclophilin probe and primer set versus the log (ng) for each HCV replicon total RNA standard.

In an alternate assay ("Replicon Assay B"), 1000 cells were seeded per well in a 384-well collagen coated black plate from Greiner bio-one (Cat #781946) in 5% FBS. Inhibitors of this invention were added at 24 h post-seeding, and the plates were incubated for 3 days. Cells were subsequently lysed with Qiagen lysis buffer (Cat #1062731) to extract the RNA. HCV replicon RNA level was measured by real-time PCR using the RNA-to-CT kit from Applied Biosystem (Cat #4392656) and genotype-specific primers and probes. The amplicon was located within NS5B. The sequence of the PCR primers are as follows: 5B.2F, ATGGACAGGCGCCCTGA (SEQ. ID NO. 1); 5B.2R, TTGATGGGCAGCTTGGTTTC (SEQ. ID NO. 2); the probe sequence was FAM-labeled CACGCCATGCGCTGCGG (SEQ. ID NO. 3). To detect genotype 1A the primer 1A F, TGCGGAACCGGTGAGTACA and 1A R, GCGGGTTTATCCAAGAAAGGA were used; the probe sequence was FAM-CGGAATTGCCAGGACGACCGG.

The real-time RT-PCR reactions were run on ABI PRISM 7900HT or Viia7 Sequence Detection System using the following program: 48° C. for 30 minutes, 95° C. for 10 minutes, 40 cycles of 95° C. for 15 sec, 60° C. for 1 minutes. The 50% effective concentration ($EC_{50}$) was the drug concentration necessary to achieve an increase in the cycle threshold ($C_T$) of 1 over the projected baseline $C_T$. The $EC_{90}$ was the drug concentration necessary to achieve an increase in $C_T$ of 3.2 over the projected baseline $C_T$.

Data was obtained for various compounds of the present invention using the methods described in the Example above, and is presented in the table immediately below. Data for replicons 1A, 1AY93H and 2B were obtained using Replicon Assay A and data for replicons 1B were obtained using Replicon Assay B.

| | Replicon $EC_{50}$ (nM) | | | |
|---|---|---|---|---|
| Compounds | 1A | 1B | 2B | 1A Y93H |
| 1 | 0.0015 | | 5.36 | 2.324 |
| 2 | 0.0014 | 0.0023 | 0.72 | 0.034 |
| 3 | 0.0015 | 0.0032 | | |
| 4 | 0.0042 | 0.0099 | 0.48 | 0.444 |
| 5 | 0.0009 | | 4.17 | 0.708 |
| 6 | 0.0017 | 0.0018 | 0.36 | 0.088 |
| 7 | 0.0073 | | 10.49 | 49.740 |
| 8 | 0.0040 | | 1.23 | 0.603 |
| 9 | 0.0036 | | 0.27 | 0.050 |
| 10 | 0.0027 | | 1.05 | 1.430 |
| 11 | 0.0081 | | 8.23 | 21.610 |
| 12 | 0.0202 | | 33.33 | |
| 13 | 0.1467 | | | |
| 14 | 0.0057 | 0.0078 | | |
| 15 | | | 3.06 | |
| 16 | | | 1.75 | |
| 17 | 0.0327 | | 3.96 | 0.716 |
| 18 | 0.0023 | | 3.54 | 18.450 |
| 19 | 0.0016 | | 2.67 | 4.359 |
| 20 | 0.0023 | 0.0026 | 0.32 | 0.075 |
| 21 | 0.0009 | | 0.98 | 1.394 |
| 22 | 0.0015 | 0.0024 | 0.14 | 0.048 |
| 23 | 0.0031 | | 6.16 | 12.740 |
| 24 | 0.0021 | | 2.62 | 0.266 |
| 25 | 0.0012 | 0.0011 | 0.30 | 0.026 |
| 26 | 0.0009 | | 0.80 | 0.816 |
| 27 | 0.0027 | | 5.50 | |

-continued

| Compounds | Replicon EC$_{50}$ (nM) | | | |
|---|---|---|---|---|
| | 1A | 1B | 2B | 1A Y93H |
| 28 | 0.0021 | | 2.09 | 0.310 |
| 29 | 0.0009 | | 0.46 | 3.246 |
| 30 | 0.0012 | 0.0017 | 0.06 | 0.026 |
| 31 | 0.0013 | | 1.64 | 5.652 |
| 32 | 0.0022 | | 0.90 | 0.185 |
| 33 | 0.0028 | 0.0026 | | |
| 34 | 0.0084 | | | 0.793 |
| 35 | 0.0034 | 0.0030 | | |
| 36 | 0.0023 | 0.0029 | 0.11 | 0.102 |
| 37 | 0.0040 | 0.0036 | 1.32 | 0.857 |
| 38 | 0.2230 | | | 0.737 |
| 39 | 0.0068 | | 0.33 | 1.655 |
| 40 | 0.0084 | | 1.54 | 0.536 |
| 41 | 0.0019 | | 0.57 | 0.317 |
| 42 | 0.0309 | | 6.16 | 5.010 |
| 43 | 0.0281 | | 0.06 | 1.020 |
| 44 | 0.0679 | | | 0.434 |
| 45 | 0.0484 | | | 4.220 |

NOTE:
Blank entries denote that data was not available.

Uses of the Heterocycle-Substituted Tetracyclic Compounds

The Heterocycle-Substituted Tetracyclic Compounds are useful in human and veterinary medicine for treating or preventing a viral infection in a patient. In one embodiment, the Heterocycle-Substituted Tetracyclic Compounds can be inhibitors of viral replication. In another embodiment, the Heterocycle-Substituted Tetracyclic Compounds can be inhibitors of HCV replication. Accordingly, the Heterocycle-Substituted Tetracyclic Compounds are useful for treating viral infections, such as HCV. In accordance with the invention, the Heterocycle-Substituted Tetracyclic Compounds can be administered to a patient in need of treatment or prevention of a viral infection.

Accordingly, in one embodiment, the invention provides methods for treating a viral infection in a patient comprising administering to the patient an effective amount of at least one Heterocycle-Substituted Tetracyclic Compound or a pharmaceutically acceptable salt thereof.

Treatment or Prevention of a Flaviviridae Virus

The Heterocycle-Substituted Tetracyclic Compounds can be useful for treating or preventing a viral infection caused by the Flaviviridae family of viruses.

Examples of Flaviviridae infections that can be treated or prevented using the present methods include but are not limited to, dengue fever, Japanese encephalitis, Kyasanur Forest disease, Murray Valley encephalitis, St. Louis encephalitis, Tick-borne encephalitis, West Nile encephalitis, yellow fever and Hepatitis C Virus (HCV) infection.

In one embodiment, the Flaviviridae infection being treated is hepatitis C virus infection.

Treatment or Prevention of HCV Infection

The Heterocycle-Substituted Tetracyclic Compounds are useful in the inhibition of HCV replication, the treatment of HCV infection and/or reduction of the likelihood or severity of symptoms of HCV infection and the inhibition of HCV viral replication and/or HCV viral production in a cell-based system. For example, the Heterocycle-Substituted Tetracyclic Compounds are useful in treating infection by HCV after suspected past exposure to HCV by such means as blood transfusion, exchange of body fluids, bites, accidental needle stick, or exposure to patient blood during surgery or other medical procedures.

In one embodiment, the hepatitis C infection is acute hepatitis C. In another embodiment, the hepatitis C infection is chronic hepatitis C.

Accordingly, in one embodiment, the invention provides methods for treating HCV infection in a patient, the methods comprising administering to the patient an effective amount of at least one Heterocycle-Substituted Tetracyclic Compound or a pharmaceutically acceptable salt thereof. In a specific embodiment, the amount administered is effective to treat or prevent infection by HCV in the patient. In another specific embodiment, the amount administered is effective to inhibit HCV viral replication and/or viral production in the patient.

The Heterocycle-Substituted Tetracyclic Compounds are also useful in the preparation and execution of screening assays for antiviral compounds. For example the Heterocycle-Substituted Tetracyclic Compounds are useful for identifying resistant HCV replicon cell lines harboring mutations within NS5A, which are excellent screening tools for more powerful antiviral compounds. Furthermore, the Heterocycle-Substituted Tetracyclic Compounds are useful in establishing or determining the binding site of other antivirals to the HCV replicase.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a and 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al., *J Gen Virol*, 78(Pt1):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol*, 75(Pt 5):1053-1061 (1994)).

Combination Therapy

In another embodiment, the present methods for treating or preventing HCV infection can further comprise the administration of one or more additional therapeutic agents which are not Heterocycle-Substituted Tetracyclic Compounds.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one Heterocycle-Substituted Tetracyclic Compound, or a pharmaceutically acceptable salt thereof, and (ii) at least one additional therapeutic agent that is other than a Heterocycle-Substituted Tetracyclic Compound, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Heterocycle-Substituted Tetracyclic Compound and an additional therapeutic agent may be present in fixed amounts (dosage amounts) in a single dosage unit (e.g., a capsule, a tablet and the like).

In one embodiment, the at least one Heterocycle-Substituted Tetracyclic Compound is administered during a time when the additional therapeutic agent(s) exert their prophylactic or therapeutic effect, or vice versa.

In another embodiment, the at least one Heterocycle-Substituted Tetracyclic Compound and the additional therapeutic agent(s) are administered in doses commonly employed when such agents are used as monotherapy for treating a viral infection.

In another embodiment, the at least one Heterocycle-Substituted Tetracyclic Compound and the additional therapeutic agent(s) are administered in doses lower than the doses commonly employed when such agents are used as monotherapy for treating a viral infection.

In still another embodiment, the at least one Heterocycle-Substituted Tetracyclic Compound and the additional therapeutic agent(s) act synergistically and are administered in doses lower than the doses commonly employed when such agents are used as monotherapy for treating a viral infection.

In one embodiment, the at least one Heterocycle-Substituted Tetracyclic Compound and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HCV infection.

The at least one Heterocycle-Substituted Tetracyclic Compound and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Heterocycle-Substituted Tetracyclic Compound and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In still another embodiment, the additional therapeutic agent is an HCV NS5B polymerase inhibitor.

In another embodiment, the additional therapeutic agent is a nucleoside inhibitor.

In another embodiment, the additional therapeutic agent is an interferon.

In yet another embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In still another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor In yet another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In a further embodiment, the additional therapeutic agent is an HCV entry inhibitor.

In another embodiment, the additional therapeutic agent is an HCV assembly inhibitor.

In one embodiment, the additional therapeutic agents comprise a viral protease inhibitor and a viral polymerase inhibitor.

In still another embodiment, the additional therapeutic agents comprise a viral protease inhibitor and an immunomodulatory agent.

In yet another embodiment, the additional therapeutic agents comprise a polymerase inhibitor and an immunomodulatory agent.

In another embodiment, the additional therapeutic agents comprise a viral protease inhibitor and a nucleoside.

In another embodiment, the additional therapeutic agents comprise an immunomodulatory agent and a nucleoside.

In one embodiment, the additional therapeutic agents comprise an HCV protease inhibitor and an HCV polymerase inhibitor.

In another embodiment, the additional therapeutic agents comprise a nucleoside and an HCV NS5A inhibitor.

In another embodiment, the additional therapeutic agents comprise a viral protease inhibitor, an immunomodulatory agent and a nucleoside.

In a further embodiment, the additional therapeutic agents comprise a viral protease inhibitor, a viral polymerase inhibitor and an immunomodulatory agent.

In another embodiment, the additional therapeutic agent is ribavirin.

HCV polymerase inhibitors useful in the present compositions and methods include, but are not limited to, VP-19744 (Wyeth/ViroPharma), PSI-7851 (Pharmasset), GS-7977 (sofosbuvir, Gilead), R7128 (Roche/Pharmasset), PF-868554/filibuvir (Pfizer), VCH-759 (ViroChem Pharma), HCV-796 (Wyeth/ViroPharma), IDX-184 (Idenix), IDX-375 (Idenix), NM-283 (Idenix/Novartis), R-1626 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH222 (ViroChem), VCH916 (ViroChem), VCH716(ViroChem), GSK-71185 (Glaxo SmithKline), ANA598 (Anadys), GSK-625433 (Glaxo SmithKline) and XTL-2125 (XTL Biopharmaceuticals), and pharmaceutically acceptable salts thereof, and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004), and pharmaceutically acceptable salts thereof.

Other HCV polymerase inhibitors useful in the present compositions and methods include, but are not limited to, those disclosed in International Publication Nos. WO 08/082484, WO 08/082488, WO 08/083351, WO 08/136815, WO 09/032116, WO 09/032123, WO 09/032124 and WO 09/032125, and pharmaceutically acceptable salts thereof.

Interferons useful in the present compositions and methods include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™ from Schering-Plough Corporation), interferon alpha-2b-XL (e.g., as sold under the trade name PEG-Intron™), interferon alpha-2c (Berofor Alpha™, Boehringer Ingelheim, Ingelheim, Germany), PEG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus) and IFN—α-2b-XL (Flamel Technologies), and consensus interferon as defined by determination of a consensus sequence of naturally occurring interferon alphas (Infergen™, Amgen, Thousand Oaks, Calif.).

Antibody therapy agents useful in the present compositions and methods include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like).

Examples of viral protease inhbitors useful in the present compositions and methods include, but are not limited to, an HCV protease inhibitor.

HCV protease inhibitors useful in the present compositions and methods include, but are not limited to, those disclosed in U.S. Pat. Nos. 7,494,988, 7,485,625, 7,449,447, 7,442,695, 7,425,576, 7,342,041, 7,253,160, 7,244,721, 7,205,330, 7,192,957, 7,186,747, 7,173,057, 7,169,760, 7,012,066, 6,914,122, 6,911,428, 6,894,072, 6,846,802, 6,838,475, 6,800,434, 6,767,991, 5,017,380, 4,933,443, 4,812,561 and 4,634,697; U.S. Patent Publication Nos. US20020068702, US20020160962, US20050119168, US20050176648, US20050209164, US20050249702 and US20070042968; and International Publication Nos. WO 03/006490, WO 03/087092, WO 04/092161 and WO 08/124148.

Additional HCV protease inhibitors useful in the present compositions and methods include, but are not limited to, SCH503034 (Boceprevir, Schering-Plough), SCH900518 (Schering-Plough), VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott), TMC-435350 (Medivir), ITMN—191/R7227 (InterMune/Roche), EA-058 (Abbott/Enanta), EA-063 (Abbott/Enanta), GS-9132 (Gilead/Achillion), ACH-1095 (Gilead/Achillon), IDX-136 (Idenix), IDX-316 (Idenix), ITMN—8356 (InterMune), ITMN—8347 (InterMune), ITMN—8096 (InterMune), ITMN—7587 (InterMune), BMS-650032 (Bristol-Myers Squibb), VX-985 (Vertex) and PHX1766 (Phenomix), and pharmaceutically acceptable salts thereof.

Further examples of HCV protease inhbitors useful in the present compositions and methods include, but are not limited to, those disclosed in Landro et al., *Biochemistry*, 36(31):9340-9348 (1997); Ingallinella et al., *Biochemistry*, 37(25):8906-8914 (1998); Llinàs-Brunet et al., *Bioorg Med Chem Lett*, 8(13):1713-1718 (1998); Martin et al., *Biochemistry*, 37(33):11459-11468 (1998); Dimasi et al., *J Virol*, 71(10):7461-7469 (1997); Martin et al., *Protein Eng*, 10(5): 607-614 (1997); Elzouki et al., *J Hepat*, 27(1):42-48 (1997); *BioWorld Today*, 9(217):4 (Nov. 10, 1998); U.S. Patent Publication Nos. US2005/0249702 and US 2007/0274951; and International Publication Nos. WO 98/14181, WO 98/17679, WO 98/17679, WO 98/22496 and WO 99/07734 and WO 05/087731.

Further examples of HCV protease inhibitors useful in the present compositions and methods include, but are not limited to, Grazoprevir (Merck), which has the following structure:
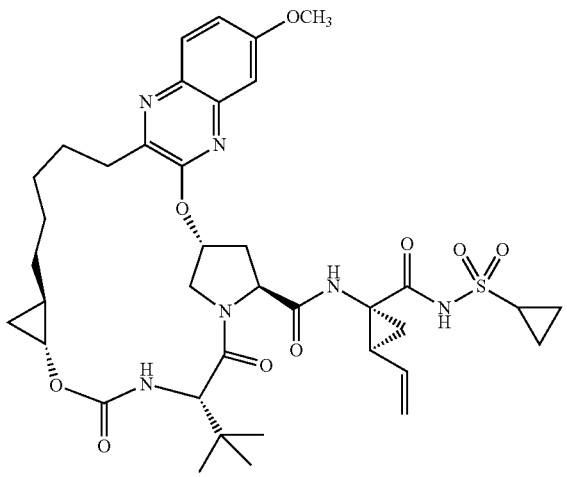 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1nc3ccc(OC)cc3nc1O2)C(=O)NS(=O)(=O)C1CC1]
and the following compounds:
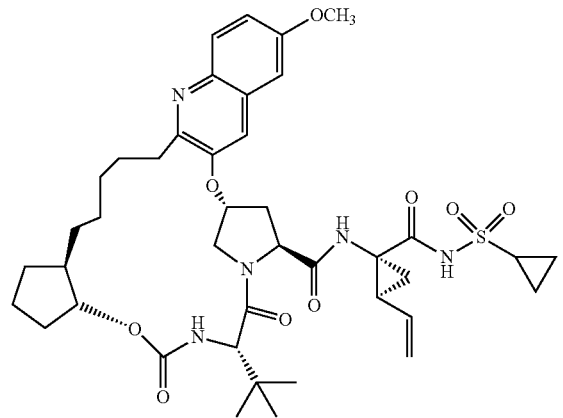
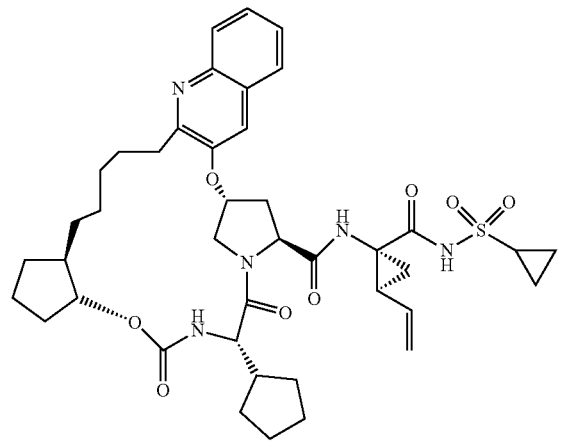
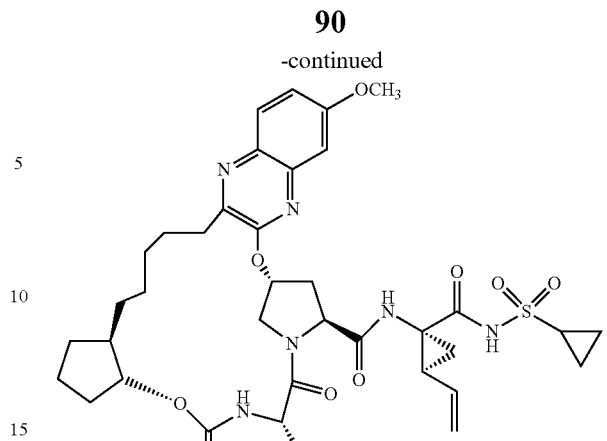
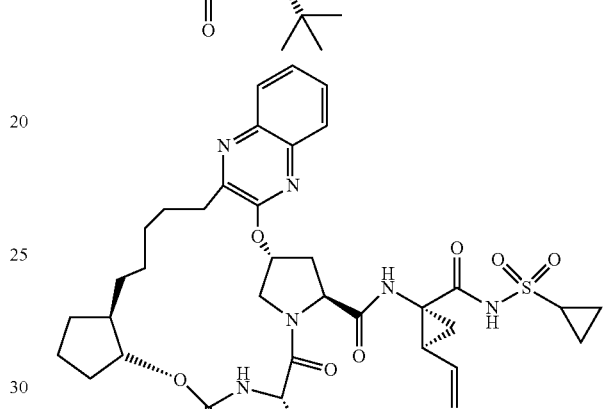
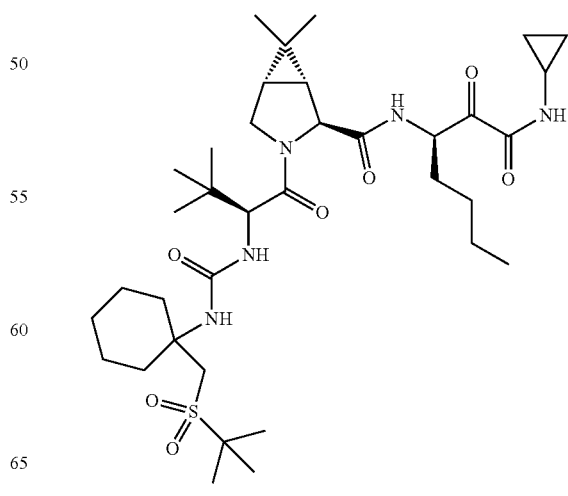

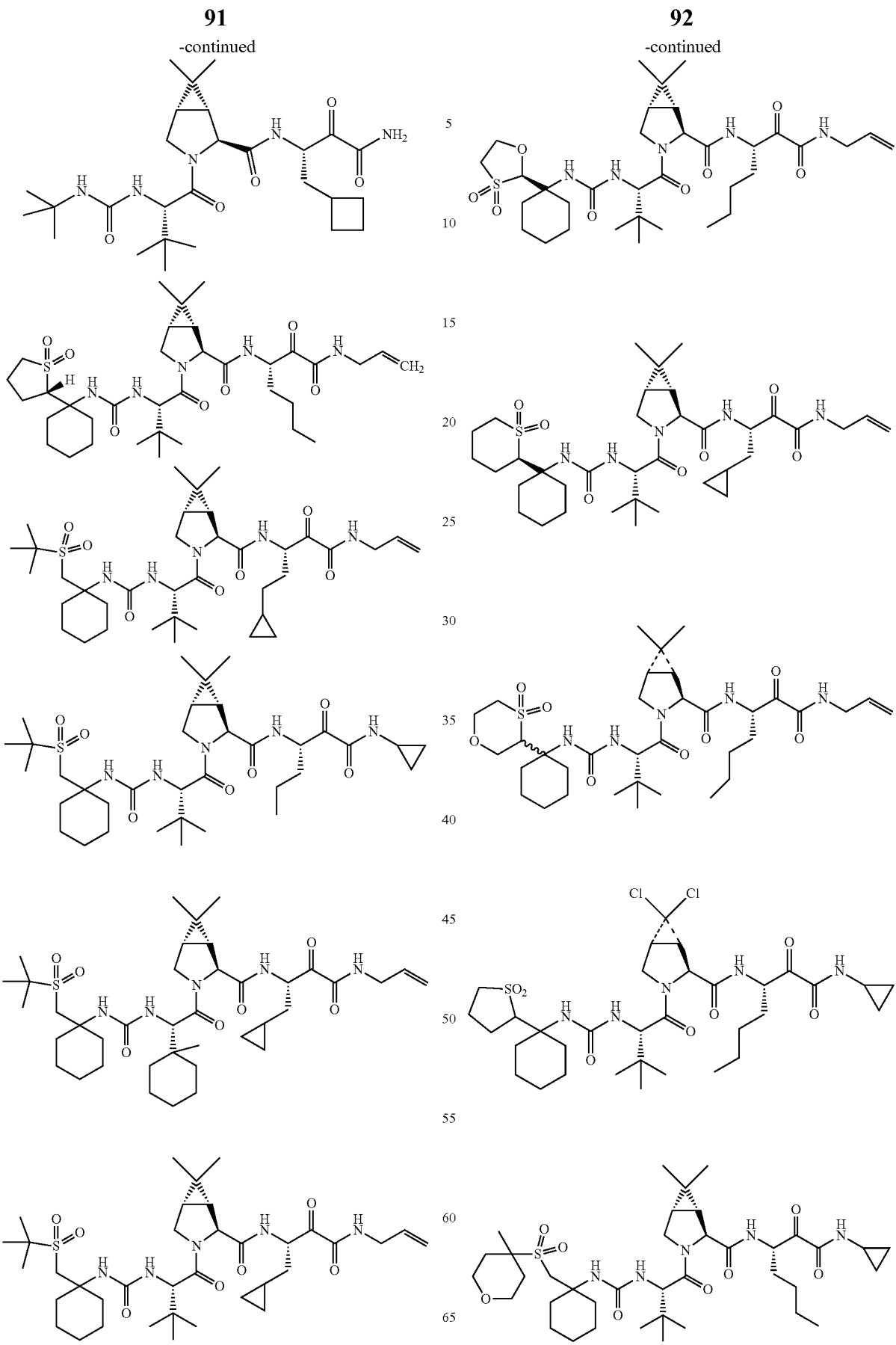

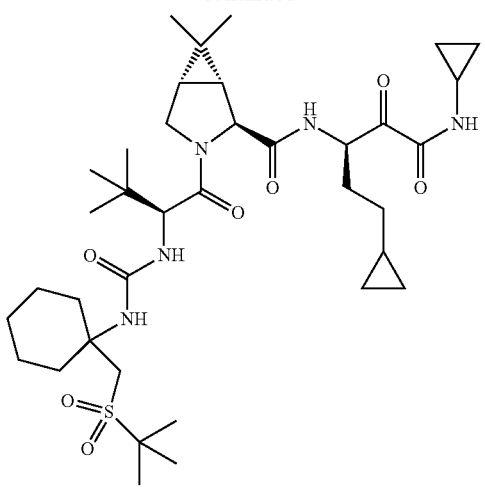

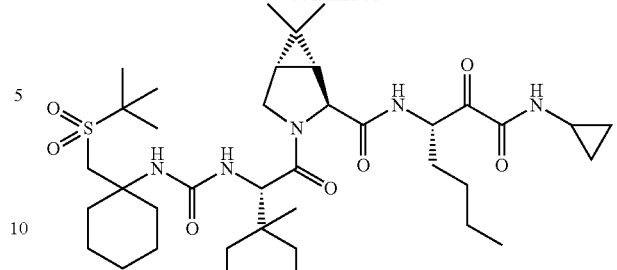

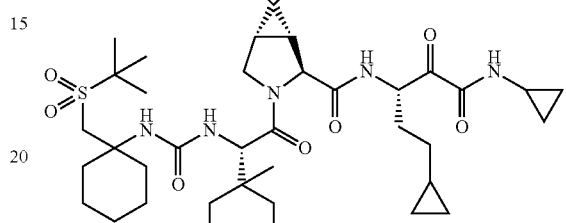

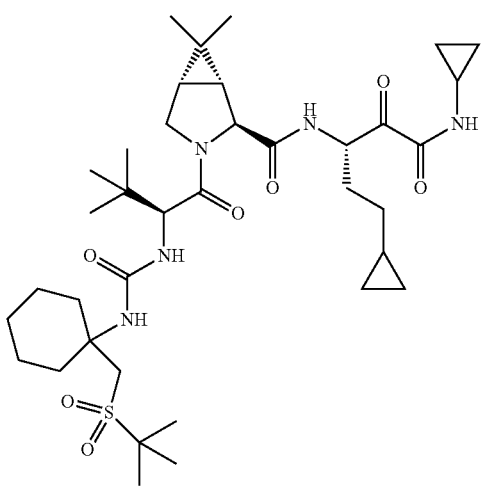

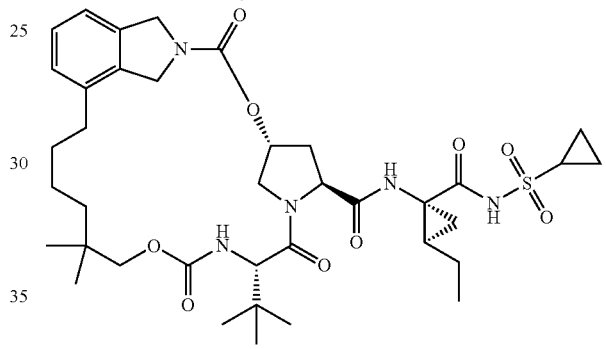

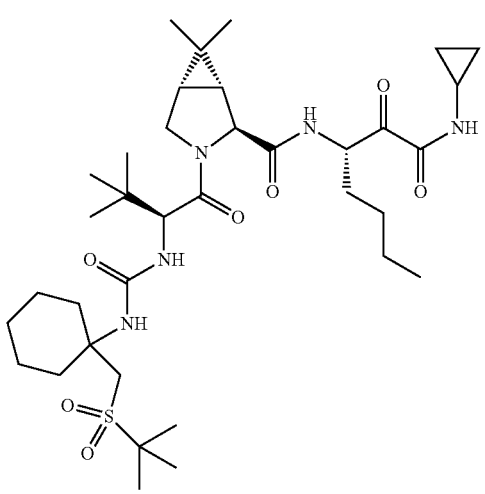

and pharmaceutically acceptable salts thereof.

HCV viral replication inhibitors useful in the present compositions and methods include, but are not limited to, HCV replicase inhibitors, IRES inhibitors, NS4A inhibitors, NS3 helicase inhibitors, NS3 protease inhibitors, NS5A inhibitors, NS5B inhibitors, ribavirin, AZD-2836 (Astra Zeneca), BMS-790052 (Bristol-Myers Squibb, see Gao et al., Nature, 465:96-100 (2010)), viramidine and A-831 (Arrow Therapeutics), an antisense agent or a therapeutic vaccine.

HCV NS4A inhibitors useful in the useful in the present compositions and methods include, but are not limited to, those disclosed in U.S. Pat. Nos. 7,476,686 and 7,273,885; U.S. Patent Publication No. US20090022688; and International Publication Nos. WO 2006/019831 and WO 2006/019832. Additional HCV NS4A inhibitors useful in the useful in the present compositions and methods include, but are not limited to, AZD2836 (Astra Zeneca) and ACH-806 (Achillon Pharmaceuticals, New Haven, Conn.).

HCV replicase inhibitors useful in the useful in the present compositions and methods include, but are not limited to, those disclosed in U.S. Patent Publication No. US20090081636.

Therapeutic vaccines useful in the present compositions and methods include, but are not limited to, IC41 (Intercell Novartis), CSL123 (Chiron/CSL), GI 5005 (Globeimmune), TG-4040 (Transgene), GNI-103 (GENimmune), Hepavaxx C (ViRex Medical), ChronVac-C (Inovio/Tripep), PeviPRO™ (Pevion Biotect), HCV/MF59 (Chiron/Novartis) and Civacir (NABI).

Examples of further additional therapeutic agents useful in the present compositions and methods include, but are not limited to, Ritonavir (Abbott), TT033 (Benitec/Tacere Bio/Pfizer), Sirna-034 (Sirna Therapeutics), GNI-104 (GENimmune), GI-5005 (Globelmmune), IDX-102 (Idenix), Levovirin™ (ICN Pharmaceuticals, Costa Mesa, Calif.); Humax (Genmab), ITX-2155 (Ithrex/Novartis), PRO 206 (Progenics), HepaCide-I (NanoVirocides), MX3235 (Migenix), SCY-635 (Scynexis); KPE02003002 (Kemin Pharma), Lenocta (VioQuest Pharmaceuticals), IET—Interferon Enhancing Therapy (Transition Therapeutics), Zadaxin (SciClone Pharma), VP 50406™ (Viropharma, Incorporated, Exton, Pennsylvania); Taribavirin (Valeant Pharmaceuticals); Nitazoxanide (Romark); Debio 025 (Debiopharm); GS-9450 (Gilead); PF-4878691 (Pfizer); ANA773 (Anadys); SCV-07 (SciClone Pharmaceuticals); NIM-881 (Novartis); ISIS 14803™ (ISIS Pharmaceuticals, Carlsbad, Calif.); Heptazyme™ (Ribozyme Pharmaceuticals, Boulder, Colorado); Thymosin™ (SciClone Pharmaceuticals, San Mateo, Calif.); Maxamine™ (Maxim Pharmaceuticals, San Diego, Calif.); NKB-122 (JenKen Bioscience Inc., N.C.); Alinia (Romark Laboratories), INFORM-1 (a combination of R7128 and ITMN—191); and mycophenolate mofetil (Hoffman-LaRoche, Nutley, N.J.), and pharmaceutically acceptable salts thereof.

The doses and dosage regimen of the other agents used in the combination therapies of the present invention for the treatment or prevention of HCV infection can be determined by the attending clinician, taking into consideration the approved doses and dosage regimen in the package insert; the age, sex and general health of the patient; and the type and severity of the viral infection or related disease or disorder. When administered in combination, the Heterocycle-Substituted Tetracyclic Compound(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

In a further embodiment, when the additional therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

In one embodiment, one or more compounds of the present invention are administered with one or more additional therapeutic agents selected from: an immunomodulator, a viral replication inhibitor, an antisense agent, a therapeutic vaccine, a viral polymerase inhibitor, a nucleoside inhibitor, a viral protease inhibitor, a viral helicase inhibitor, a viral polymerase inhibitor a virion production inhibitor, a viral entry inhibitor, a viral assembly inhibitor, an antibody therapy (monoclonal or polyclonal), and any agent useful for treating an RNA-dependent polymerase-related disorder.

In another embodiment, one or more compounds of the present invention are administered with one or more additional therapeutic agents selected from an HCV protease inhibitor, an HCV polymerase inhibitor, an HCV replication inhibitor, a nucleoside and ribavirin. The combination therapies can include any combination of these additional therapeutic agents.

In another embodiment, one or more compounds of the present invention are administered with one additional therapeutic agent selected from an HCV protease inhibitor and ribavirin.

In still another embodiment, one or more compounds of the present invention are administered with two additional therapeutic agents selected from an HCV protease inhibitor, an HCV replication inhibitor, a nucleoside and ribavirin.

In another embodiment, one or more compounds of the present invention are administered with an HCV protease inhibitor and ribavirin. In another specific embodiment, one or more compounds of the present invention are administered with ribavirin.

In another embodiment, one or more compounds of the present invention are administered with three additional therapeutic agents selected from an HCV protease inhibitor, an HCV replication inhibitor, a nucleoside, a pegylated interferon and ribavirin.

In one embodiment, one or more compounds of the present invention are administered with one or more additional therapeutic agents selected from an HCV polymerase inhibitor, a viral protease inhibitor, and a viral replication inhibitor. In another embodiment, one or more compounds of the present invention are administered with one or more additional therapeutic agents selected from an HCV polymerase inhibitor, a viral protease inhibitor, and a viral replication inhibitor. In another embodiment, one or more compounds of the present invention are administered with one or more additional therapeutic agents selected from an HCV polymerase inhibitor, a viral protease inhibitor, and ribavirin.

In one embodiment, one or more compounds of the present invention are administered with one additional therapeutic agent selected from an HCV polymerase inhibitor, a viral protease inhibitor, and a viral replication inhibitor. In another embodiment, one or more compounds of the present invention are administered with ribavirin.

In one embodiment, one or more compounds of the present invention are administered with two additional therapeutic agents selected from an HCV polymerase inhibitor, a viral protease inhibitor, and a viral replication inhibitor.

In another embodiment, one or more compounds of the present invention are administered with ribavirin and another therapeutic agent.

In another embodiment, one or more compounds of the present invention are administered with ribavirin and another therapeutic agent, wherein the additional therapeutic agent is selected from an HCV polymerase inhibitor, a viral protease inhibitor, and a viral replication inhibitor.

In still another embodiment, one or more compounds of the present invention are administered with ribavirin and a viral protease inhibitor.

In another embodiment, one or more compounds of the present invention are administered with ribavirin and an HCV protease inhibitor.

In another embodiment, one or more compounds of the present invention are administered with ribavirin and either boceprevir or telaprevir.

In a further embodiment, one or more compounds of the present invention are administered with ribavirin and an HCV polymerase inhibitor.

In another embodiment, one or more compounds of the present invention are administered with ribavirin.

In one embodiment, one or more compounds of the present invention are administered with Grazoprevir.

In one embodiment, one or more compounds of the present invention are administered with sofosbuvir.

Compositions and Administration

Due to their activity, the Heterocycle-Substituted Tetracyclic Compounds are useful in veterinary and human medicine. As described above, the Heterocycle-Substituted Tetracyclic Compounds are useful for treating or preventing HCV infection in a patient in need thereof.

When administered to a patient, the Heterocycle-Substituted Tetracyclic Compounds can be administered as a component of a composition that comprises a pharmaceutically acceptable carrier or vehicle. The present invention provides pharmaceutical compositions comprising an effective amount of at least one Heterocycle-Substituted Tetracyclic Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Heterocycle-Substituted Tetracyclic Compounds are administered orally.

In another embodiment, the one or more Heterocycle-Substituted Tetracyclic Compounds are administered intravenously.

In still another embodiment, the one or more Heterocycle-Substituted Tetracyclic Compounds are administered sublingually.

In one embodiment, a pharmaceutical preparation comprising at least one Heterocycle-Substituted Tetracyclic Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Heterocycle-Substituted Tetracyclic Compound(s) by weight or volume. In various embodiments, the present compositions can contain, in one embodiment, from about 1% to about 70% or from about 5% to about 60% of the Heterocycle-Substituted Tetracyclic Compound(s) by weight or volume.

The amount and frequency of administration of the Heterocycle-Substituted Tetracyclic Compounds will be regulated according to the judgment of the attending clinician considering such factors as age, condition and size of the patient as well as severity of the symptoms being treated. Generally, a total daily dosage of the at least one Heterocycle-Substituted Tetracyclic Compound(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Heterocycle-Substituted Tetracyclic Compound or a pharmaceutically acceptable salt thereof; (ii) one or more additional therapeutic agents that are not a Heterocycle-Substituted Tetracyclic Compound; and (iii) a pharmaceutically acceptable carrier, wherein the amounts in the composition are together effective to treat HCV infection.

In one embodiment, the present invention provides compositions comprising a Compound of Formula (I) and a pharmaceutically acceptable carrier.

In another embodiment, the present invention provides compositions comprising a Compound of Formula (I), a pharmaceutically acceptable carrier, and a second therapeutic agent selected from the group consisting of HCV antiviral agents, immunomodulators, and anti-infective agents.

In another embodiment, the present invention provides compositions comprising a Compound of Formula (I), a pharmaceutically acceptable carrier, and wto additional therapeutic agents, each of which are independently selected from the group consisting of HCV antiviral agents, immunomodulators, and anti-infective agents.

Kits

In one aspect, the present invention provides a kit comprising a therapeutically effective amount of at least one Heterocycle-Substituted Tetracyclic Compound, or a pharmaceutically acceptable salt, solvate, ester or prodrug of said compound and a pharmaceutically acceptable carrier, vehicle or diluent.

In another aspect the present invention provides a kit comprising an amount of at least one Heterocycle-Substituted Tetracyclic Compound, or a pharmaceutically acceptable salt, solvate, ester or prodrug of said compound and an amount of at least one additional therapeutic agent listed above, wherein the amounts of the two or more active ingredients result in a desired therapeutic effect. In one embodiment, the one or more Heterocycle-Substituted Tetracyclic Compounds and the one or more additional therapeutic agents are provided in the same container. In one embodiment, the one or more Heterocycle-Substituted Tetracyclic Compounds and the one or more additional therapeutic agents are provided in separate containers.

What is claimed is:

1. A compound having the formula (I):

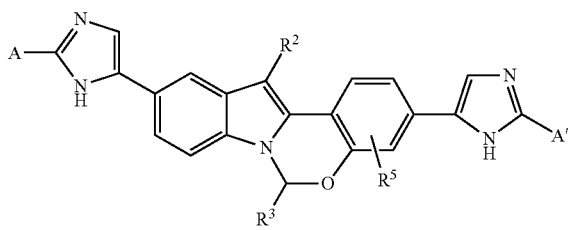

(I)

or a pharmaceutically acceptable salt thereof, wherein:

A is:

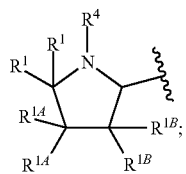

A' is:

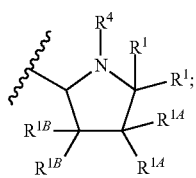

each occurrence of $R^1$ is independently selected from H, $C_1$-$C_6$ alkyl, $C_3$-$C_7$ cycloalkyl, $C_1$-$C_6$ haloalkyl, —O—$C_1$-$C_6$ alkyl, —N($R^9$)$_2$, —O—($C_1$-$C_6$ haloalkyl), and halo;

each occurrence of $R^{1A}$ is independently selected from H, $C_1$-$C_6$ alkyl, $C_3$-$C_7$ cycloalkyl, $C_1$-$C_6$ haloalkyl, —O—$C_1$-$C_6$ alkyl, —N($R^9$)$_2$, —O—($C_1$-$C_6$ haloalkyl), and halo, or one $R^{1A}$ group and an $R^1$ group that are attached to same ring, together with the ring carbon atoms to which they are attached, can combine to form a fused $C_3$-$C_7$ cycloalkyl group, or two $R^{1A}$ groups that are attached to the same carbon atom, and the common carbon atom to which they are attached, can combine to form a spirocyclic $C_3$-$C_7$ cycloalkyl group;

each occurrence of $R^{1B}$ is independently H, $C_1$-$C_6$ alkyl, $C_3$-$C_7$ cycloalkyl, $C_1$-$C_6$ haloalkyl, —O—$C_1$-$C_6$ alkyl, —N($R^9$)$_2$, —O—($C_1$-$C_6$ haloalkyl), or halo, or an $R^{1B}$ group and an $R^{1A}$ group that are attached to the same ring, together with the carbon atoms to which they are attached, can combine to form a fused $C_3$-$C_7$ cycloalkyl group, or an $R^{1B}$ group and an $R^1$ group that are attached to the same ring, can combine to form a bridging group having the formula —CH$_2$— or —CH$_2$CH$_2$—;

$R^2$ is H, $C_1$-$C_6$ alkyl, $C_3$-$C_7$ cycloalkyl, phenyl or halo, wherein said phenyl group and said $C_3$-$C_7$ cycloalkyl can be optionally substituted with up to 4 groups, which can be the same or different and are selected from $C_1$-$C_6$ alkyl, halo, —O—$C_1$-$C_6$ alkyl and —N($R^9$)$_2$;

$R^3$ is selected from furanyl, oxazolyl, oxadiazolyl, isoxazolyl, imidazolyl, benzoxazolyl, benzisoxazolyl, benzimidazolyl, pyrazolo[1,5-a]pyridinyl, imidazo[1,2-a]pyridinyl, and 6,7-dihydro-5H-pyrrolo[1,2-a]imidazolyl, wherein said furanyl, oxazolyl, oxadiazolyl, isoxazolyl, imidazolyl, benzoxazolyl, benzisoxazolyl, benzimidazolyl, pyrazolo[1,5-a]pyridinyl, imidazo[1,2-a]pyridinyl, and 6,7-dihydro-5H-pyrrolo[1,2-a]imidazolyl, groups can be optionally substituted on one or more ring carbon atoms with $R^6$, and optionally substituted on a ring nitrogen atom with $C_1$-$C_6$ alkyl;

each occurrence of $R^4$ is independently selected from —C(O)—C($R^7$)$_2$NHC(O)O—$R^8$;

$R^5$ represents up to 3 substituents, each independently selected from halo, —CN, $C_1$-$C_6$ alkyl, $C_1$-$C_6$ haloalkyl, $C_3$-$C_7$ cycloalkyl, 4 to 6-membered monocyclic heterocycloalkyl, 5 or 6-membered monocyclic heteroaryl, $C_6$-$C_{10}$ aryl, benzyl and —O—($C_1$-$C_6$ alkyl), wherein said $C_3$-$C_7$ cycloalkyl group, said 4 to 6-membered monocyclic heterocycloalkyl group, said 5 or 6-membered monocyclic heteroaryl group, said $C_6$-$C_{10}$ aryl group, or the phenyl moiety of said benzyl group can be optionally substituted with up to 3 groups, which can be the same or different, and are selected from halo, —CN, $C_1$-$C_6$ alkyl, $C_1$-$C_6$ haloalkyl, —O—$C_1$-$C_6$ alkyl, —($C_1$-$C_6$ alkylene)-O—$C_1$-$C_6$ alkyl and —O—($C_1$-$C_6$ haloalkyl);

$R^6$ represents up to 3 optional substituents, each independently selected from halo, —CN, $C_1$-$C_6$ alkyl, $C_1$-$C_6$ haloalkyl, $C_3$-$C_7$ cycloalkyl, $C_6$-$C_{10}$ aryl, benzyl, —O—($C_1$-$C_6$ alkyl), $C_2$-$C_6$ alkenyl, $C_1$-$C_6$ hydroxyalkyl, —N($R^9$)$_2$, —($C_1$-$C_6$ alkylene)$_m$-($C_6$-$C_{10}$ aryl), —($C_1$-$C_6$ alkylene)$_m$-($C_3$-$C_7$ cycloalkyl), 5 or 6-membered monocyclic heteroaryl, and 9 or 10-membered bicyclic heteroaryl, wherein said 5 or 6-membered monocyclic heteroaryl group can be optionally substituted on a ring carbon atom with $C_1$-$C_6$ alkyl, $C_3$-$C_7$ cycloalkyl or phenyl, and optionally substituted on a ring nitrogen atom with $C_1$-$C_6$ alkyl; said $C_1$-$C_6$ alkyl, $C_3$-$C_7$ cycloalkyl or phenyl can be optionally substituted a ring carbon atom with halo, $C_1$-$C_6$ alkyl or $C_3$-$C_7$ cycloalkyl;

each occurrence of $R^7$ is independently selected from H, $C_1$-$C_6$ alkyl, $C_1$-$C_6$ haloalkyl, phenyl, 4 to 8-membered monocyclic heterocycloalkyl, 6 to 10-membered bicyclic heterocycloalkyl and $C_3$-$C_7$ cycloalkyl, wherein said 4 to 8-membered monocyclic heterocycloalkyl group, said 6 to 10-membered bicyclic heterocycloalkyl group and said $C_3$-$C_7$ cycloalkyl group can be optionally substituted with up to 5 groups, each independently selected from halo, —CN, $C_1$-$C_6$ alkyl, $C_1$-$C_6$ haloalkyl, $C_3$-$C_7$ cycloalkyl, —O—$C_1$-$C_6$ alkyl, —N($R^9$)$_2$ and —O—($C_1$-$C_6$ haloalkyl), and wherein said $C_3$-$C_7$ cycloalkyl group can be optionally fused to a 4 to 6-membered monocyclic heterocycloalkyl group, and wherein said 4 to 8-membered monocyclic heterocycloalkyl group and said $C_3$-$C_7$ cycloalkyl group can be substituted on a ring carbon atom with a spirocyclic $C_3$-$C_6$ cycloalkyl group; and wherein said $C_3$-$C_7$ cycloalkyl group can be substituted on a ring carbon atom with a spirocyclic 3 to 6-membered monocyclic heterocycloalkyl group, and wherein two $R^7$ groups, that are attached to a common carbon atom, together with the common carbon atom to which they are attached, join to form a $C_3$-$C_7$ cycloalkyl group;

each occurrence of $R^8$ is independently $C_1$-$C_6$ alkyl, $C_3$-$C_7$ cycloalkyl and $C_6$-$C_{10}$ aryl;

each occurrence of $R^9$ is independently selected from H, $C_1$-$C_6$ alkyl, $C_3$-$C_7$ cycloalkyl and $C_6$-$C_{10}$ aryl; and each occurrence of m is independently 0 or 1.

2. The compound of claim 1, wherein each occurrence of $R^4$ is independently —C(O)CH($R^7$)NHC(O)OCH$_3$, or a pharmaceutically acceptable salt thereof.

3. The compound of claim 1, wherein each occurrence of $R^4$ is independently —C(O)CH($R^7$)—NHC(O)OCH$_3$ and $R^7$ is $C_1$-$C_6$ alkyl, $C_1$-$C_6$ haloalkyl or 4 to 6-membered monocyclic heterocycloalkyl, wherein said 4 to 6-membered monocyclic heterocycloalkyl group can be optionally substituted with up to five $C_1$-$C_6$ alkyl groups or said 4 to 6-membered monocyclic heterocycloalkyl group can be optionally substituted on a ring carbon atom with a spirocyclic $C_3$-$C_6$ cycloalkyl group, or a pharmaceutically acceptable salt thereof.

4. The compound of claim 1 having the formula:

or a pharmaceutically acceptable salt thereof,
wherein:

each $R^1$ is H;

each $R^{1A}$ is independently H or F, or an $R^{1A}$ group and an $R^1$ group that are attached to same ring, together with the ring carbon atoms to which they are attached, can combine to form a fused cyclopropyl group;

$R^3$ is selected from furanyl, oxazolyl, oxadiazolyl, isoxazolyl, imidazolyl, benzoxazolyl, benzisoxazolyl, benzimidazolyl, pyrazolo[1,5-a]pyridinyl, imidazo[1,2-a]pyridinyl, and 6,7-dihydro-5H-pyrrolo[1,2-a]imidazolyl, wherein said furanyl, oxazolyl, oxadiazolyl, isoxazolyl, imidazolyl, benzoxazolyl, benzisoxazolyl, benzimidazolyl, pyrazolo[1,5-a]pyridinyl, imidazo[1,2-a]pyridinyl, and 6,7-dihydro-5H-pyrrolo[1,2-a]imidazolyl, groups can be optionally substituted on a ring carbon atom with $C_1$-$C_6$ alkyl, $C_3$-$C_7$ cycloalkyl or phenyl, and optionally substituted on a ring nitrogen atom with $C_1$-$C_6$ alkyl; said $C_1$-$C_6$ alkyl, $C_3$-$C_7$ cycloalkyl or phenyl can be optionally substituted a ring carbon atom with halo, $C_1$-$C_6$ alkyl or $C_3$-$C_7$ cycloalkyl;

$R^5$ is H or F; and each occurrence of $R^7$ is independently selected from $C_1$-$C_6$ alkyl, $C_1$-$C_6$ haloalkyl, and 4 to 6-membered monocyclic heterocycloalkyl, wherein said 4 to 6-membered monocyclic heterocycloalkyl group can be optionally substituted with up to 5 groups, each independently selected from halo, $C_1$-$C_6$ alkyl and $C_3$-$C_7$ cycloalkyl.

5. The compound of claim 1, wherein A and A' are each independently selected from:

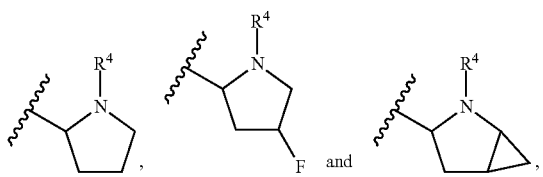

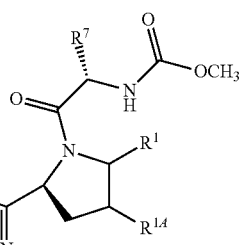

or a pharmaceutically acceptable salt thereof.

(Ia)

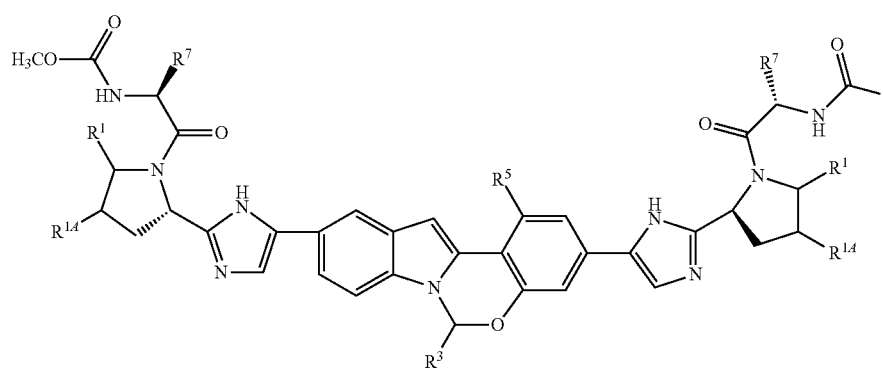

6. The compound of claim 1, wherein $R^3$ is:

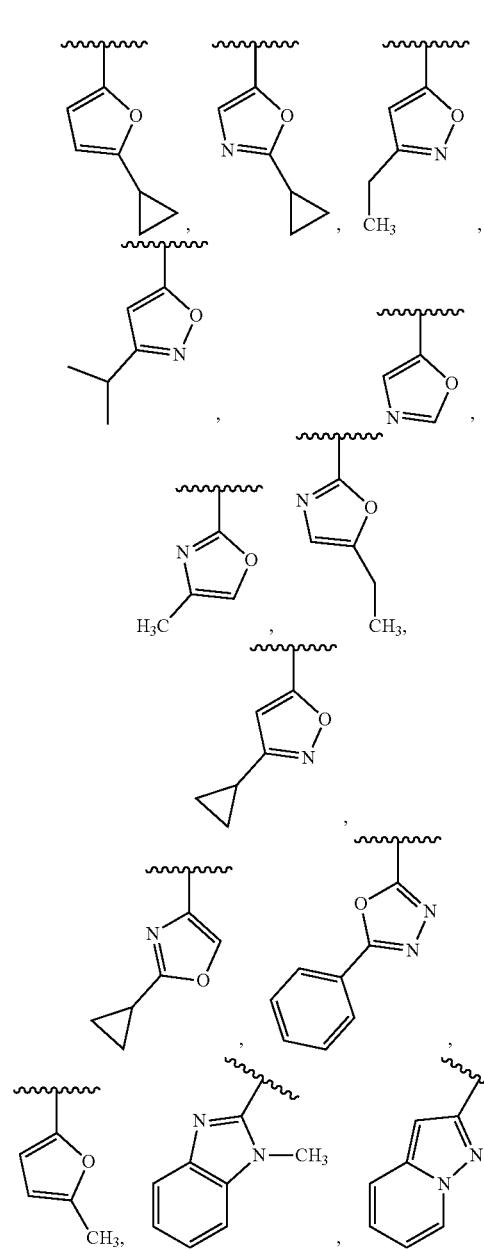

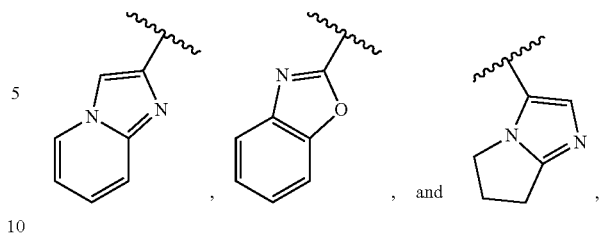

or a pharmaceutically acceptable salt thereof.

7. The compound of claim 1, wherein each occurrence of $R^7$ is independently selected from isopropyl,

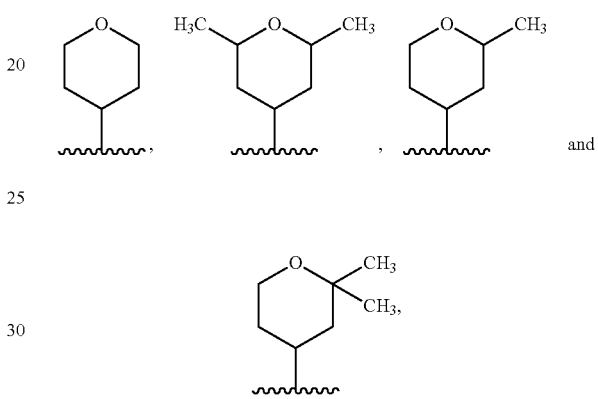

or a pharmaceutically acceptable salt thereof.

8. The compound of claim 1, wherein, R is F and each occurrence of $R^7$ is independently selected from isopropyl or:

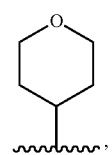

or a pharmaceutically acceptable salt thereof.

9. A compound selected from:

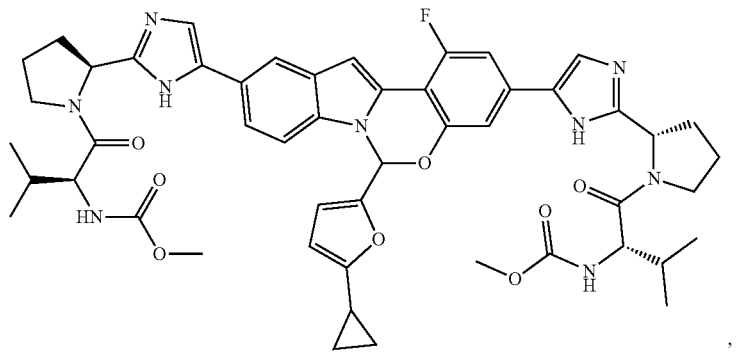

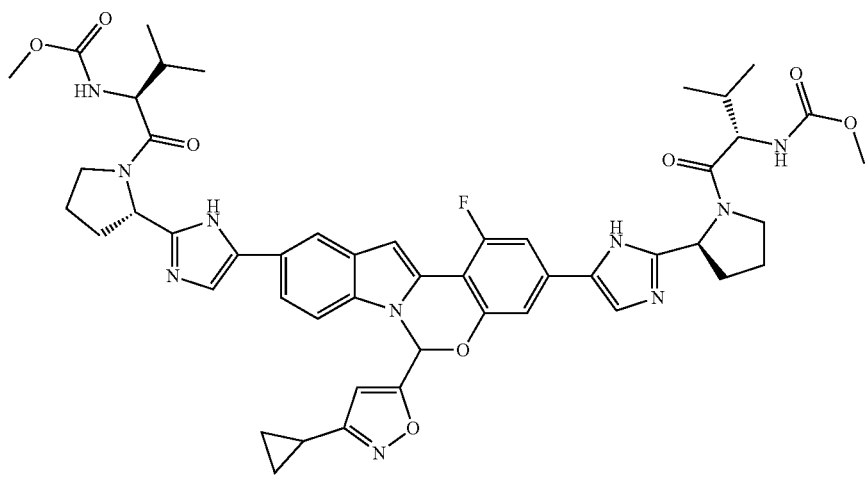
,
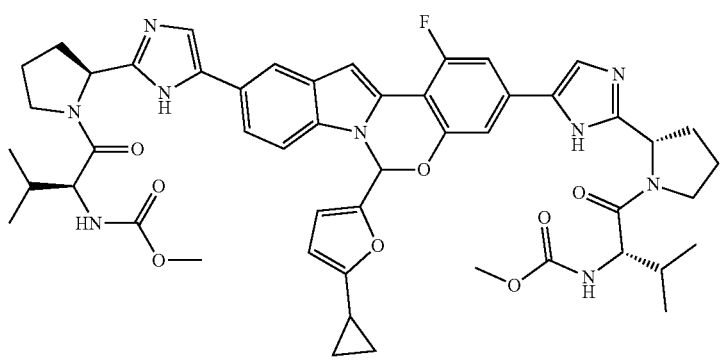
,
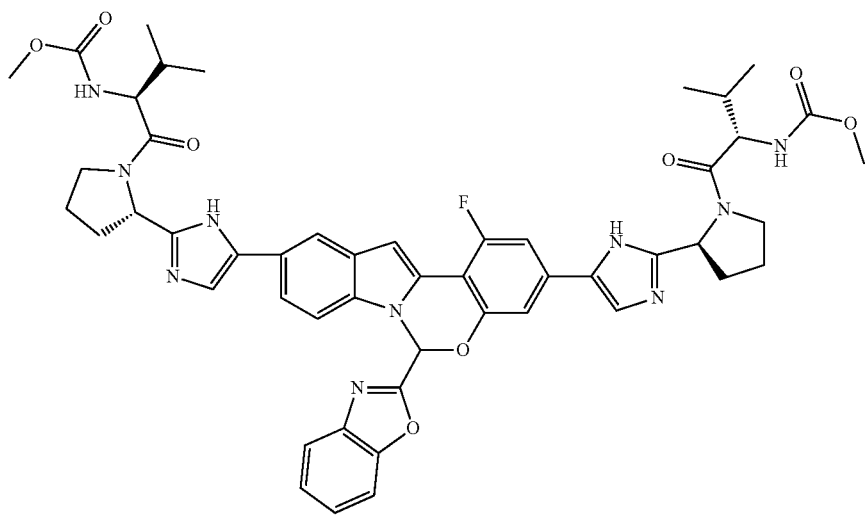
,

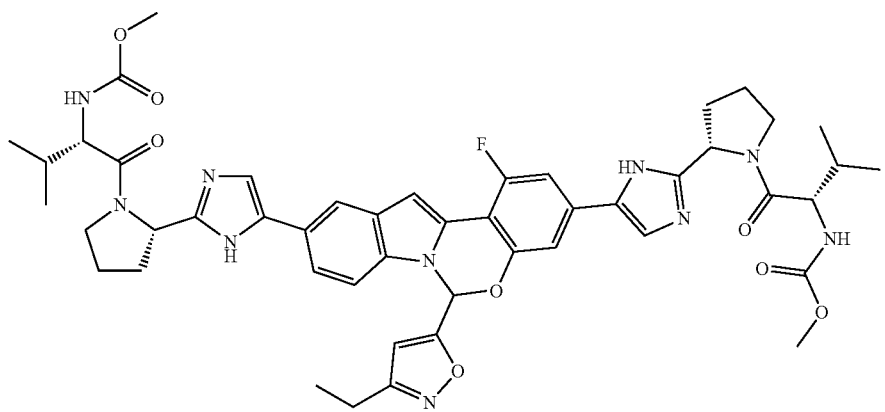
,
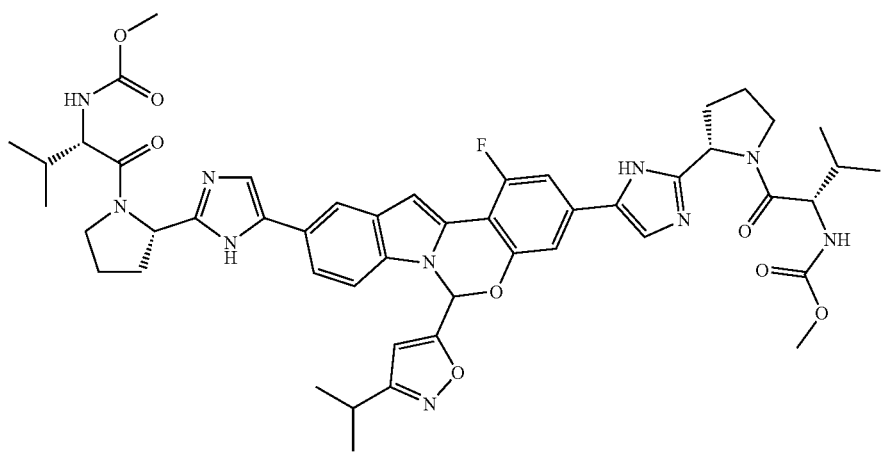
,
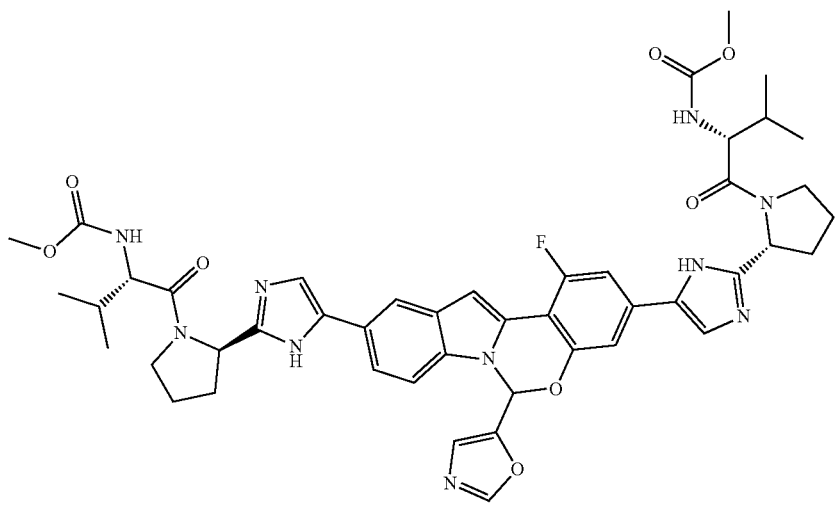
,

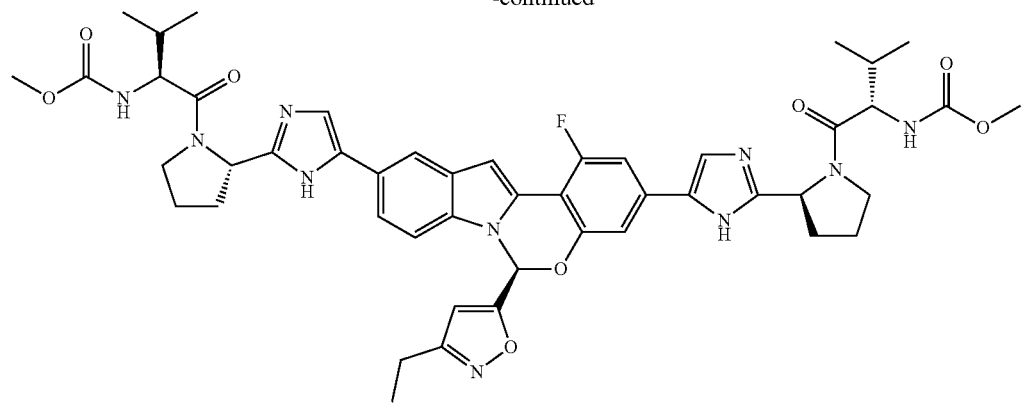
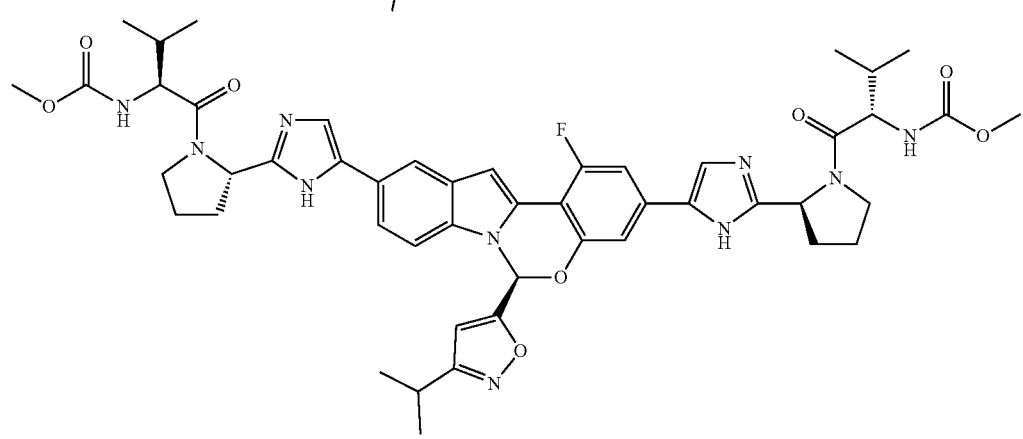
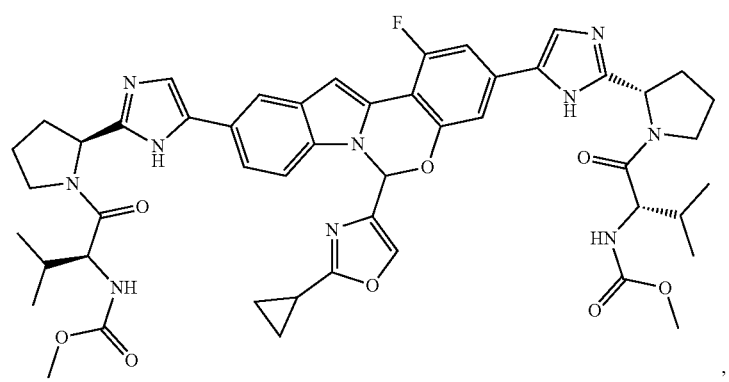
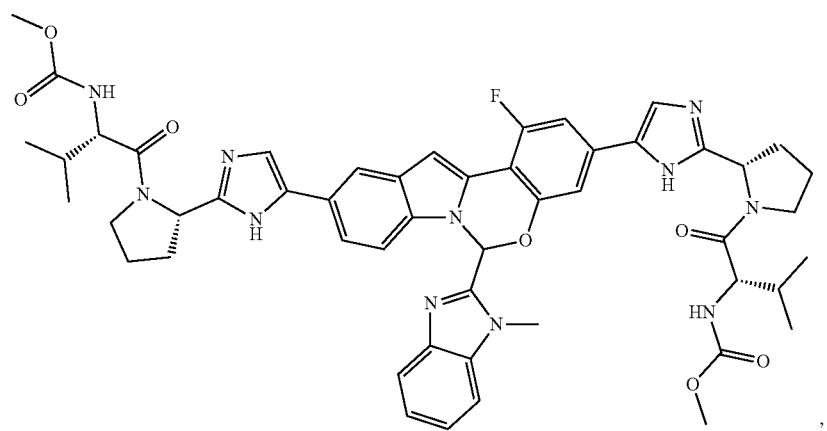

-continued
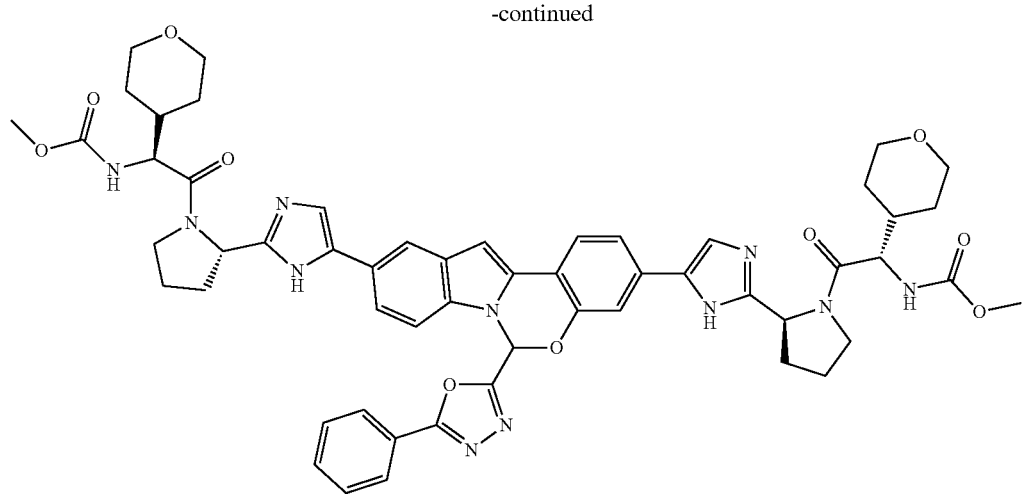
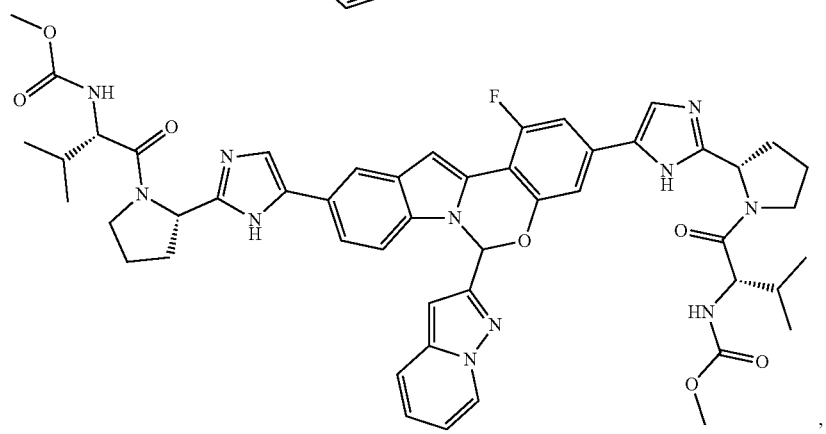
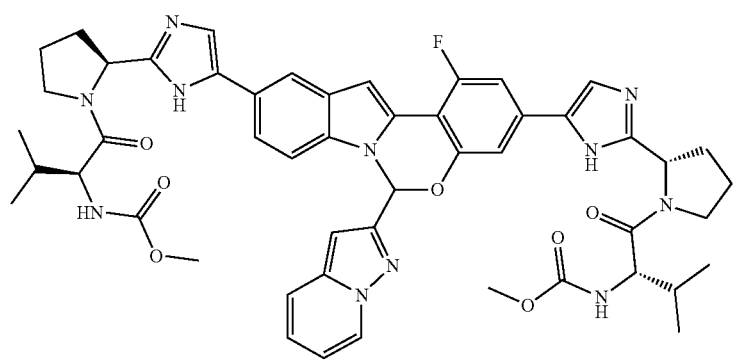
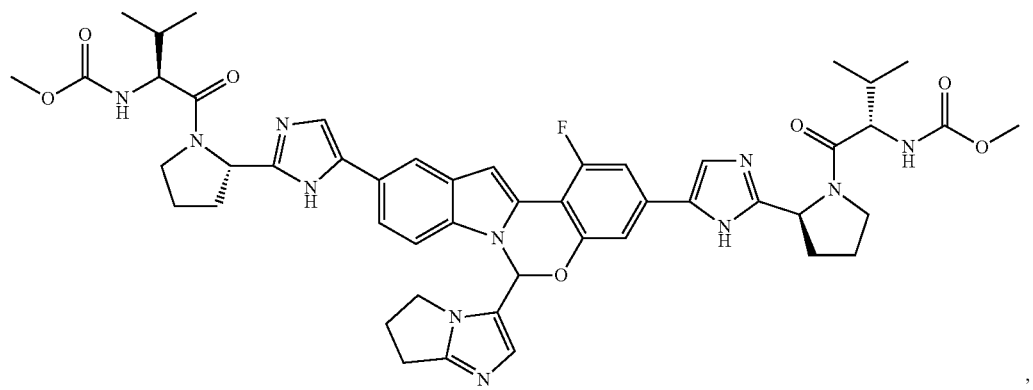

-continued
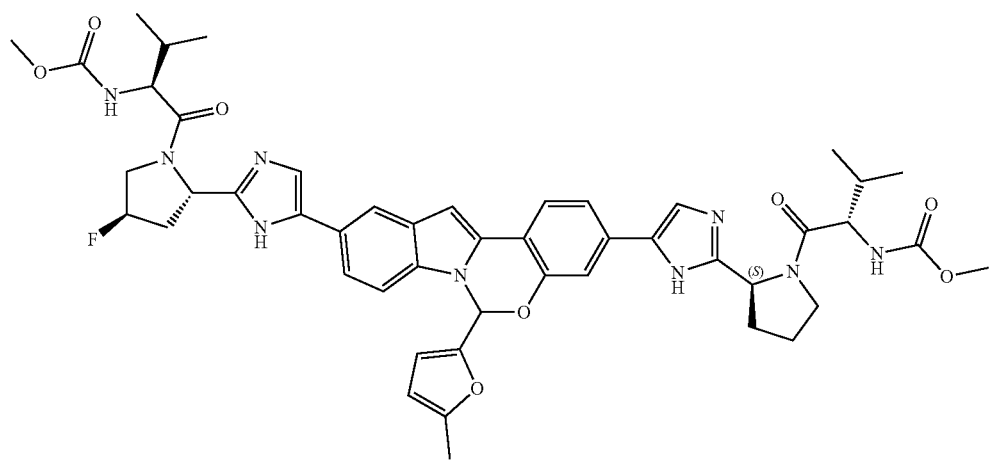
,
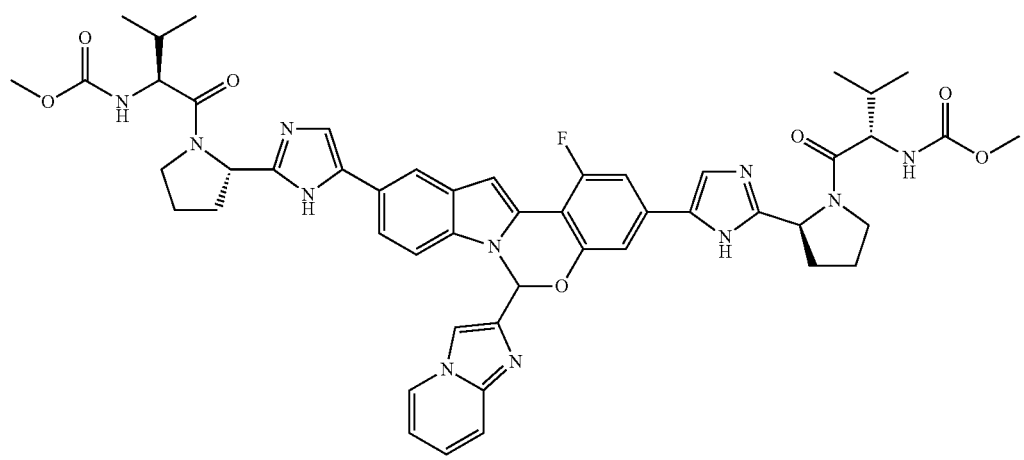
,
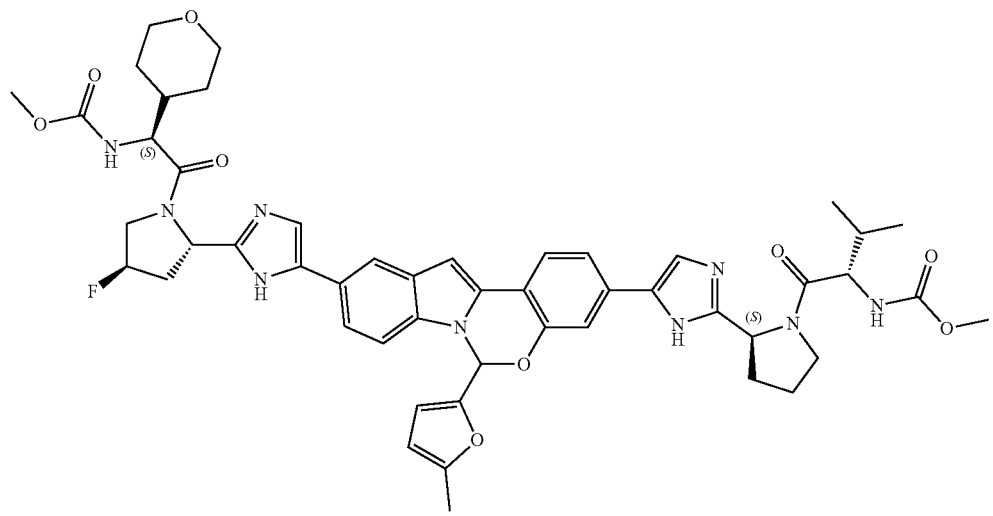
, and

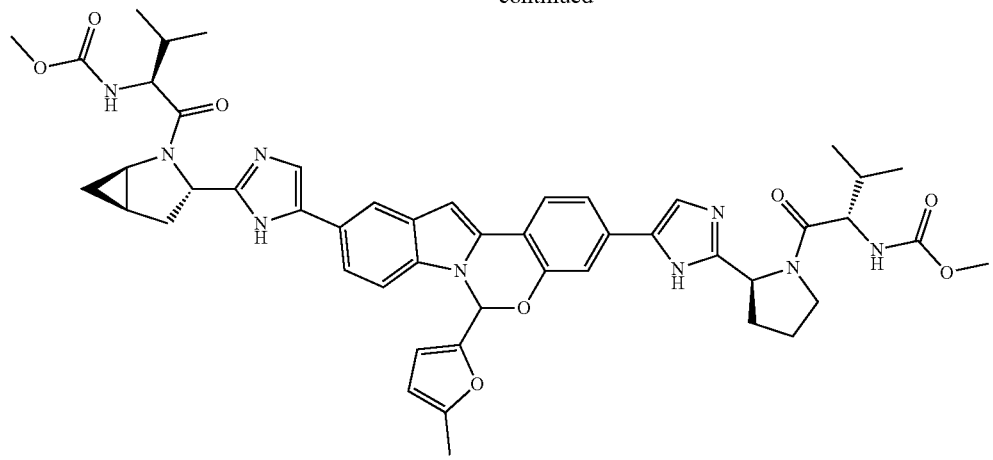

or a pharmaceutically acceptable salt thereof.

10. A pharmaceutical composition comprising an effective amount of the compound of claim 1, or a pharmaceutically acceptable salt thereof, and a pharmaceutically acceptable carrier.

11. The pharmaceutical composition of claim 10, further comprising a second therapeutic agent selected from the group consisting of HCV antiviral agents, immunomodulators, and anti-infective agents.

12. The pharmaceutical composition of claim 11, further comprising a third therapeutic agent selected from the group consisting of HCV protease inhibitors, HCV NS5A inhibitors and HCV NS5B polymerase inhibitors.

13. A method of treating a patient infected with HCV comprising the step of administering an amount of the compound according to claim 1, or a pharmaceutically acceptable salt thereof, effective to treat infection by HCV in said patient.

14. The method of claim 13, further comprising administering a second additional therapeutic agent to said patient, wherein said second additional therapeutic agent is independently selected from HCV protease inhibitors, HCV NS5A inhibitors and HCV NS5B polymerase inhibitors.

15. The method of claim 14, further comprising administering a third additional therapeutic agent to said patient, wherein said third additional therapeutic agent is independently selected from HCV protease inhibitors, HCV NS5A inhibitors and HCV NS5B polymerase inhibitors.

16. The method of claim 14, wherein said second additional therapeutic agent is grazoprevir.

* * * * *